United States Patent
Vesely et al.

(10) Patent No.: US 6,246,898 B1
(45) Date of Patent: *Jun. 12, 2001

(54) METHOD FOR CARRYING OUT A MEDICAL PROCEDURE USING A THREE-DIMENSIONAL TRACKING AND IMAGING SYSTEM

(75) Inventors: Ivan Vesely, Cleveland Heights, OH (US); Wayne Smith; George Klein, both of London (CA); Daniel Burkhoff, Tenafly, NJ (US)

(73) Assignee: Sonometrics Corporation, Ontario (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/074,860

(22) Filed: May 8, 1998

Related U.S. Application Data

(63) Continuation-in-part of application No. 08/812,518, filed on Mar. 7, 1997, now Pat. No. 5,797,849, which is a continuation-in-part of application No. PCT/CA96/00194, filed on Mar. 26, 1996, which is a continuation-in-part of application No. 08/411,959, filed on Mar. 28, 1995, now Pat. No. 5,515,853.

(51) Int. Cl.[7] .................................................. A61B 5/05
(52) U.S. Cl. ......................... 600/424; 606/130; 600/429; 600/439
(58) Field of Search ..................................... 600/407, 411, 600/424, 437, 439, 471, 425, 426, 427, 461, 462, 464; 606/130

(56) References Cited

U.S. PATENT DOCUMENTS

| 4,173,228 | 11/1979 | VanSteenwyk et al. . |
| 4,304,239 | 12/1981 | Perlin . |

(List continued on next page.)

FOREIGN PATENT DOCUMENTS

| 3904914 | 8/1990 | (DE) . |
| 41 19 150 | 12/1992 | (DE) . |

(List continued on next page.)

OTHER PUBLICATIONS

Davis J.W., Improved Arrival Time Detection for Cardiac Pulse Transit Sonomicrometry, *Computers in Cardiology 1996*, pp. 145–159, 1996.

Morse, Wayne, Medical Electronics, *IEEE Spectrum*, pp. 99–102, Jan. 1997.

Josephson et al., Comparison of Endocardial Catheter Mapping with Intraoperative Mapping of Ventricular Tachycardia, *Circulation*, vol. 61, No. 2, pp. 395–404, 1980.

(List continued on next page.)

*Primary Examiner*—Brian L. Casler
(74) *Attorney, Agent, or Firm*—Arter & Hadden LLP

(57) ABSTRACT

A method for carrying out a medical procedure using a 3-D tracking and imaging system (1600). A surgical instrument, such as a catheter, probe, sensor, pacemaker lead, needle, or the like is inserted into a living being, and the position of the surgical instrument is tracked as it moves through a medium in a bodily structure. The location of the surgical instrument relative to its immediate surroundings is displayed to improve a physician's ability to precisely position the surgical instrument. The medical procedures including targeted drug delivery, sewing sutures, removal of an obstruction from the circulatory system, a biopsy, amniocentesis, brain surgery, measurement of cervical dilation, evaluation of knee stability, assessment of myocardial contractibility, eye surgery, prostate surgery, trans-myocardial revascularization (TMR), robotic surgery, and evaluation of RF transmissions.

6 Claims, 75 Drawing Sheets

U.S. PATENT DOCUMENTS

| | | |
|---|---|---|
| 4,431,005 | 2/1984 | McCormick . |
| 4,444,195 | 4/1984 | Gold . |
| 4,499,493 | 2/1985 | Nishimura . |
| 4,522,212 | 6/1985 | Gelinas et al. . |
| 4,573,473 | 3/1986 | Hess . |
| 4,613,866 | 9/1986 | Blood . |
| 4,628,937 | 12/1986 | Hess et al. . |
| 4,649,924 | 3/1987 | Taccardi . |
| 4,697,595 | 10/1987 | Breyer et al. . |
| 4,699,147 | 10/1987 | Chilson et al. . |
| 4,777,955 | 10/1988 | Brayton et al. . |
| 4,812,976 | 3/1989 | Lundy . |
| 4,821,731 | 4/1989 | Martinelli et al. . |
| 4,899,750 | 2/1990 | Ekwall . |
| 4,922,912 | 5/1990 | Watanabe . |
| 4,932,414 | 6/1990 | Coleman et al. ............... 128/600.09 |
| 4,940,064 | 7/1990 | Desai . |
| 4,945,305 | 7/1990 | Blood . |
| 5,000,190 | 3/1991 | Petre . |
| 5,012,814 | 5/1991 | Mills et al. . |
| 5,016,173 | 5/1991 | Kenet et al. ........................ 382/128 |
| 5,025,786 | 6/1991 | Siegel . |
| 5,041,973 | 8/1991 | Lebron et al. . |
| 5,042,486 | 8/1991 | Pfeiler et al. . |
| 5,054,492 | 10/1991 | Scribner et al. . |
| 5,054,496 | 10/1991 | Wen et al. . |
| 5,056,517 | 10/1991 | Fenici . |
| 5,081,993 | 1/1992 | Kitney et al. . |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. . |
| 5,172,699 | 12/1992 | Svenson et al. . |
| 5,220,924 | 6/1993 | Frazin . |
| 5,222,501 | 6/1993 | Ideker et al. . |
| 5,246,016 | 9/1993 | Lieber et al. . |
| 5,295,484 | 3/1994 | Marcus et al. . |
| 5,297,549 | 3/1994 | Beatty et al. . |
| 5,318,025 | 6/1994 | Dumoulin et al. ................. 128/653.2 |
| 5,341,807 | 8/1994 | Nardella . |
| 5,357,956 | 10/1994 | Nardella . |
| 5,391,199 | 2/1995 | Ben-Haim . |
| 5,398,691 | 3/1995 | Martin et al. .................... 128/662.06 |
| 5,443,489 | * 8/1995 | Ben-Haim ............................ 607/115 |
| 5,480,422 | 1/1996 | Ben-Haim . |
| 5,515,853 | 5/1996 | Smith et al. . |
| 5,517,990 | 5/1996 | Kalfas et al. . |
| 5,546,951 | 8/1996 | Ben-Haim . |
| 5,588,430 | * 12/1996 | Bova et al. .......................... 606/130 |
| 5,622,170 | * 4/1997 | Schulz .................................. 606/130 |
| 5,638,819 | * 6/1997 | Manwaring et al. ................ 600/407 |
| 5,776,064 | * 7/1998 | Kalfas et al. ........................ 600/414 |
| 5,782,765 | * 7/1998 | Jonkman .............................. 600/424 |
| 5,797,849 | 8/1998 | Vesely et al. ........................ 600/461 |
| 5,851,183 | * 12/1998 | Bucholz ............................... 600/425 |
| 5,868,673 | * 2/1999 | Vesely .................................. 600/407 |
| 5,868,675 | 2/1999 | Henrion et al. ...................... 600/424 |
| 5,891,034 | * 4/1999 | Bucholz .............................. 600/426 |
| 5,967,980 | * 10/1999 | Ferre et al. ........................... 600/424 |
| 5,971,997 | * 10/1999 | Guthrie et al. ....................... 606/130 |
| 6,128,958 | * 10/2000 | Cain ....................................... 73/626 |

FOREIGN PATENT DOCUMENTS

| | | |
|---|---|---|
| 0 152 905 | 8/1985 | (EP) . |
| 92301264 | 2/1992 | (EP) . |
| 0 591 899 | 10/1993 | (EP) . |
| 2 709 392 | 3/1995 | (FR) . |
| US94/08352 | 7/1994 | (WO) . |
| US94/11298 | 10/1994 | (WO) . |
| US95/01103 | 1/1995 | (WO) . |
| PCT/CA96/00194 | 8/1996 | (WO) . |

OTHER PUBLICATIONS

Josephson et al., Ventricular Tachycardia during Endocardial Pacing. II. Role of Pace–Mapping to Localize Origin of Ventricular Tachycardia, *The American Journal of Cardiology*, vol. 50, pp. 11–22, Jul. 1982.

Witkowski et al., An Automated Simultaneous Transmural Cardiac Mapping System, *American Journal of Physiology*, vol. 247, pp. H661–H668, 1984.

Fann et al., Endocardial Activation Mapping and Endocardial Pace–Mapping Using a Balloon Apparatus, *American Journal of Cardiology*, vol. 55, pp. 1076–1083, Apr. 1, 1985.

Tweddell et al., Potential Mapping in Septal Tachycardia: Evaluation of a New Intraoperative Mapping Technique; *Circulation*, vol. 80 (Supplement I), No. 3, pp. I–97–I–108, Sep. 1989.

Hauer et al., Endocardial Catheter Mapping: Wire Skeleton Techniques for Representation of Computed Arrhythmogenic Sites Compared with Intraoperative Mapping, *Circulation*, vol. 74. No. 6. pp. 1346–1354, Dec. 1986.

Pogwizd et al., Reentrant and Nonreentrant Mechanisms Contribute to Arrhythmogenesis During Early Myocardial Ischemia: Results Using Three–Dimensional Mapping, *Circulation Research*, vol. 61, No. 3, pp. 352–371, Sep. 1987.

Huang et al., Radiofrequency Catheter Ablation of the Left and Right Ventricles: Anatomic and Electrophysiologic Observations, *Pace*, vol. II, pp. 449–459, Apr. 1988.

Jackman et al., New Catheter Techniques for Recording Left Free–Wall Accessory Atrioventricular Pathway Activation, *Circulation*, vol. 78, No. 3, pp. 598–611, Sep. 1988.

Shenasa et al., Cardia Mapping, Part I: Wolff–Parkinson–White Syndrome, *Pace*, vol. 13, pp. 223–230, Feb. 1990.

Scheinman et al., Current Role of Catheter Ablative Procedures in Patients with Cardiac Arrhythmias, *Circulation*, vol. 83, No. 6, pp. 2146–2153, Jun. 1991.

Buckles et al., Computer–Enhanced Mapping of Activation Sequences in the Surgical Treatment of Supraventricular Arrhythmias, *Pace*, vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome, *Journal of American College of Cardiologists*, vol. 17, No. 2, pp. 403–408, Feb. 1991.

Masse et al., A Three–Dimensional Display for Cardiac Activation Mapping, *Pace*, vol. 14, Pt. 1, pp. 538–545, Apr. 1991.

Desai et al., Orthogonal Electrode Catheter Array for Mapping of Endocardial Focal Site of Ventricular Activation, *Pace*, vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System, *Pace*, vol. 15, pp. 854–858, Jun. 1992.

Chen et al., Reappraisal of Electrical Cure of Atrioventricular Nodal Reentrant Tachycardia—Lesions from a Modified Catheter Albation Technique, *International Journal of Cardiology*, vol. 37, pp. 51–60, 1992.

Chen et al., Radiofrequency Catheter Albaltion For Treadment of Wolff–Parkinson–White Syndrome–Short–and Long–Term Follow–up, *International Journal of Cardiology*, vol. 37, pp. 199–207, 1992.

Scheinman, North American Society of Pacing and Electrophysiology (NASPE) Survey on Radiofrequency Catheter Ablation: Implications for Clinicians, Third Party Insurers, and Government Regulatory Agencies, *Pace*, vol. 15, pp. 2228–2231, Dec. 1992.

Silka et al., Phase Image Analysis of Anomalour Ventricular Activation in Petiatric Patients with Pre–excitation Syndromes or Ventricular Tachycardia, *American Heart Journal*, vol. 125, No. 2, Pt. 1, pp. 372–380, Feb. 1993.

Josephson, Clinical Cardiac Electrophysiology: Techniques and Interpretations, 2nd Ed., pp. 566–580, 608–615, 770–783, *Lea & Febiger*, Malvern, Pa., 1993.

Meyer et al., Application of Sonomicrometry and Multidimensional Scaling to Cardiac Catheter Tracking, *Transactions on BioMedical Engineering*, vol. 44, No. 11 pp. 1061–1067, Nov. 1997.

Holt et al., Ventricular Arrhythmias—A Guide to Their Localization, *British Heart Journal*, vol. 53, pp. 417–430, 1985.

Joseph et al., Role of Catheter Mapping in the Preoperative Evaluation of Ventricular Tachycardia, *American Journal of Cardiology*, vol. 40, pp. 207–220, Jan. 1982.

Kucher et al., Electrocardiographic Localization of the Site of Ventricular Tachycardia in Patients with Prior Myocardial Infarction, *JACC*, vol. 13, No. 4 pp. 893–900.

Page, Surgical Treatment of Ventricular Tachycardia: Regional Cryoablation Guided by Computerized Epicardial and Endocardial Mapping, *Circulation*, vol. 80, (Supplement I), No. 3, pp. I124–I–134, Sep. 1989.

* cited by examiner

|           |           |
|-----------|-----------|
| FIG.2A.   | FIG.2C.   |
| FIG.2B.   | FIG.2D.   |

FIG.2.

|         |         |         |         |
|---------|---------|---------|---------|
|         | FIG.3A. | FIG.3B. | FIG.3C. |
| FIG.3D. | FIG.3E. | FIG.3F. | FIG.3G. |
| FIG.3H. | FIG.3I. | FIG.3J. | FIG.3K. |
| FIG.3L. | FIG.3M. | FIG.3N. |         |
| FIG.3O. | FIG.3P. | FIG.3Q. |         |

FIG.3.

| FIG.4A. | FIG.4B. | FIG.4C. | FIG.4D. |
|---------|---------|---------|---------|
| FIG.4E. | FIG.4F. | FIG.4G. | FIG.4H. |
| FIG.4I. | FIG.4J. | FIG.4K. | FIG.4L. |
| FIG.4M. | FIG.4N. | FIG.4O. | FIG.4P. |

FIG.4.

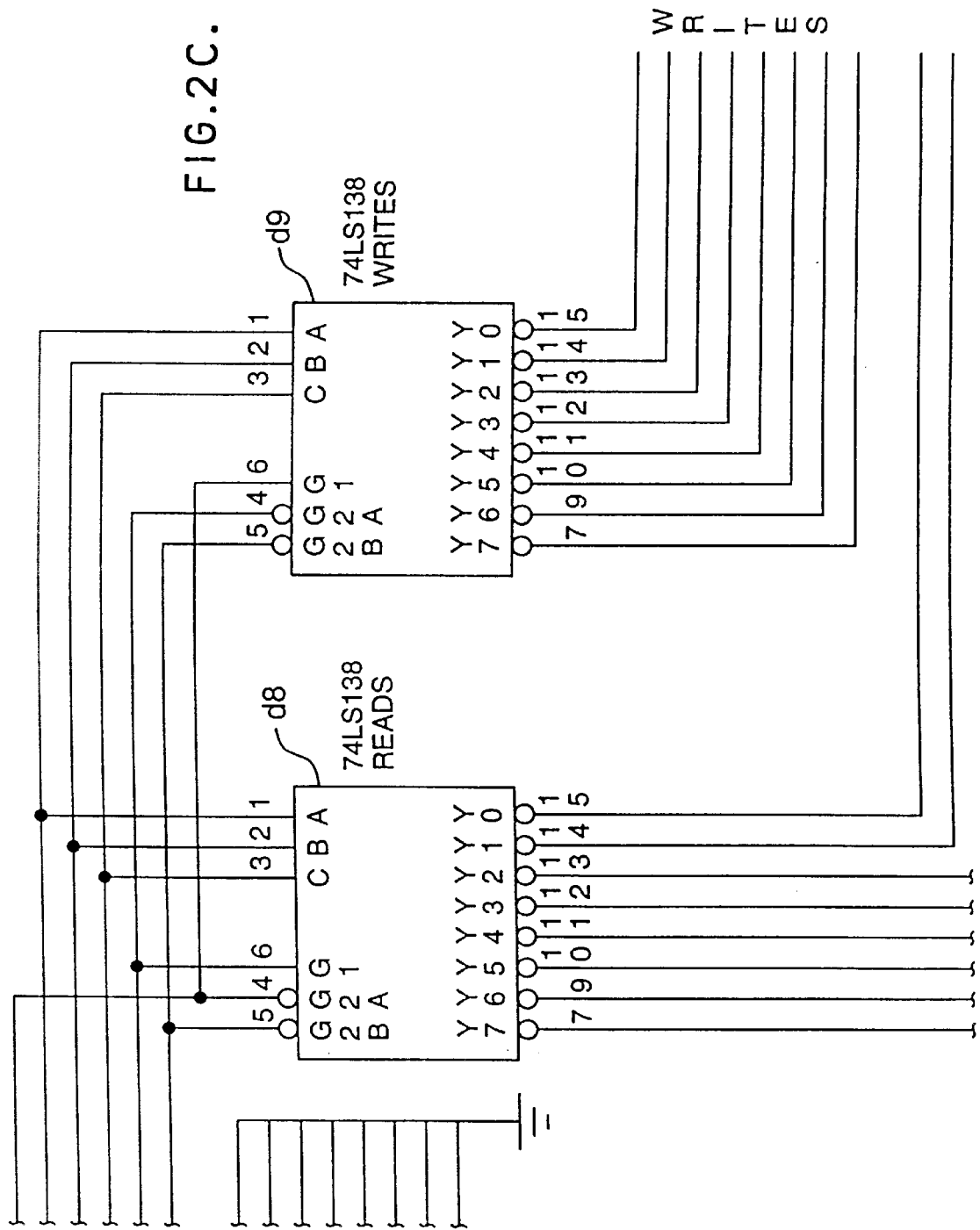

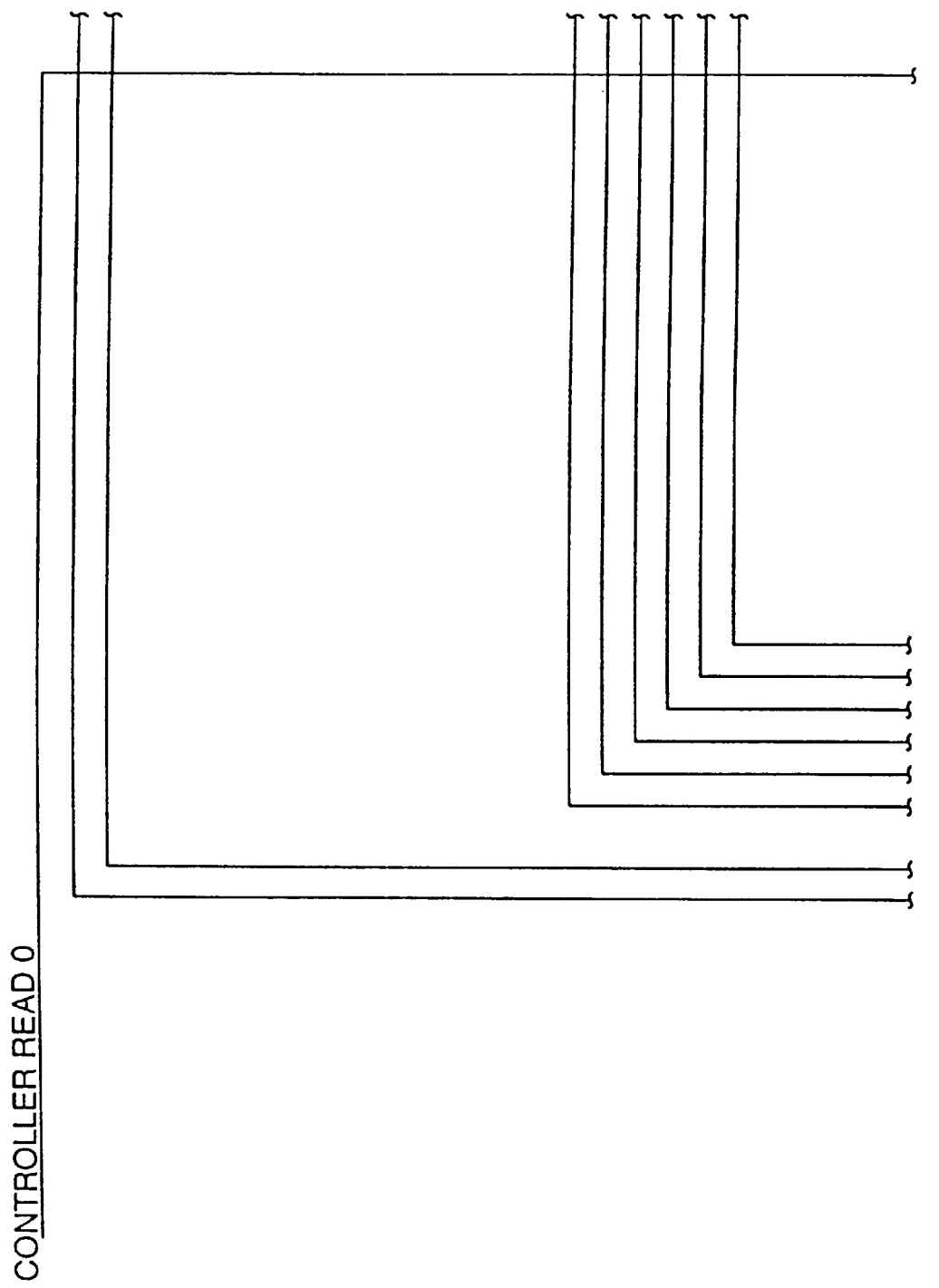

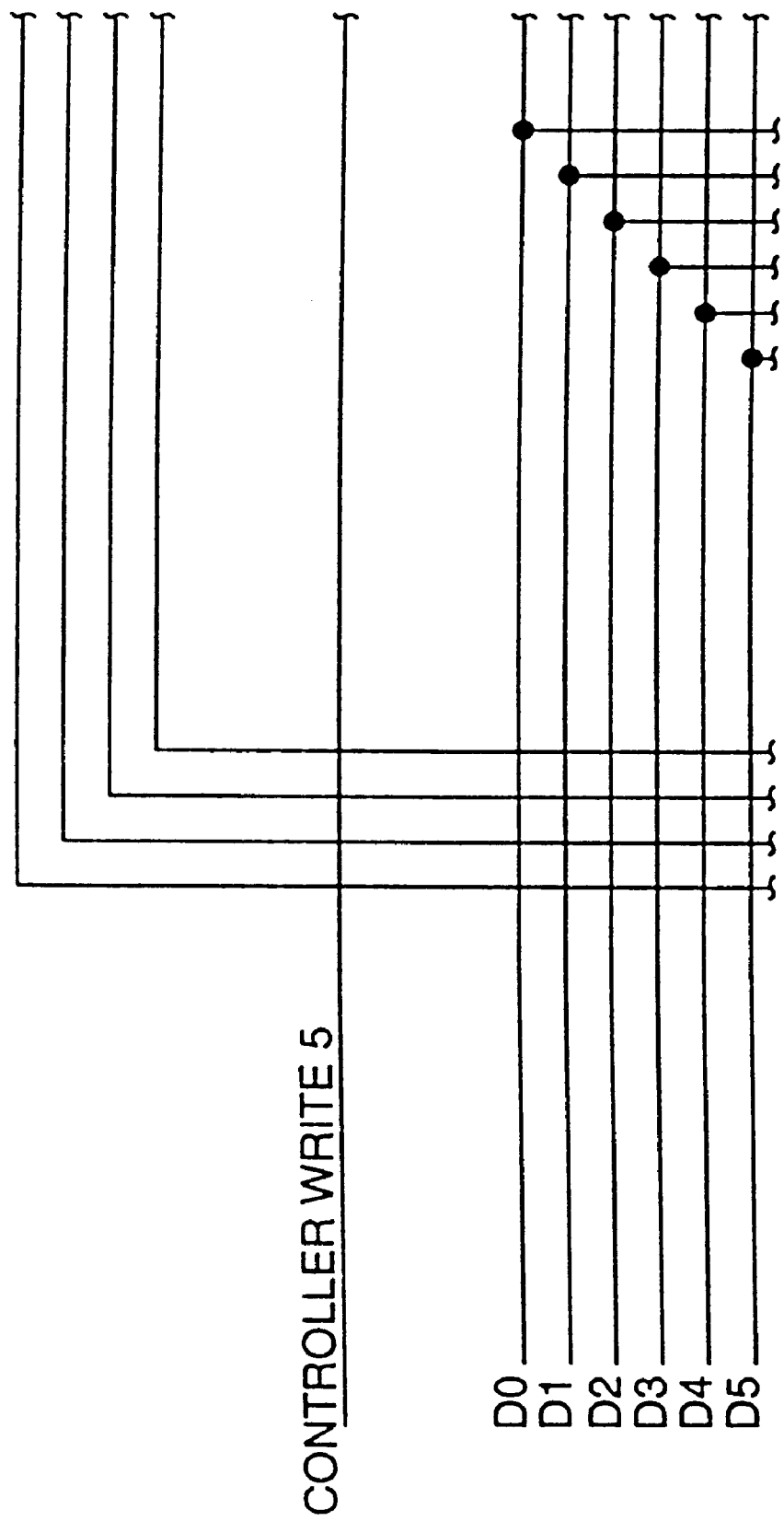

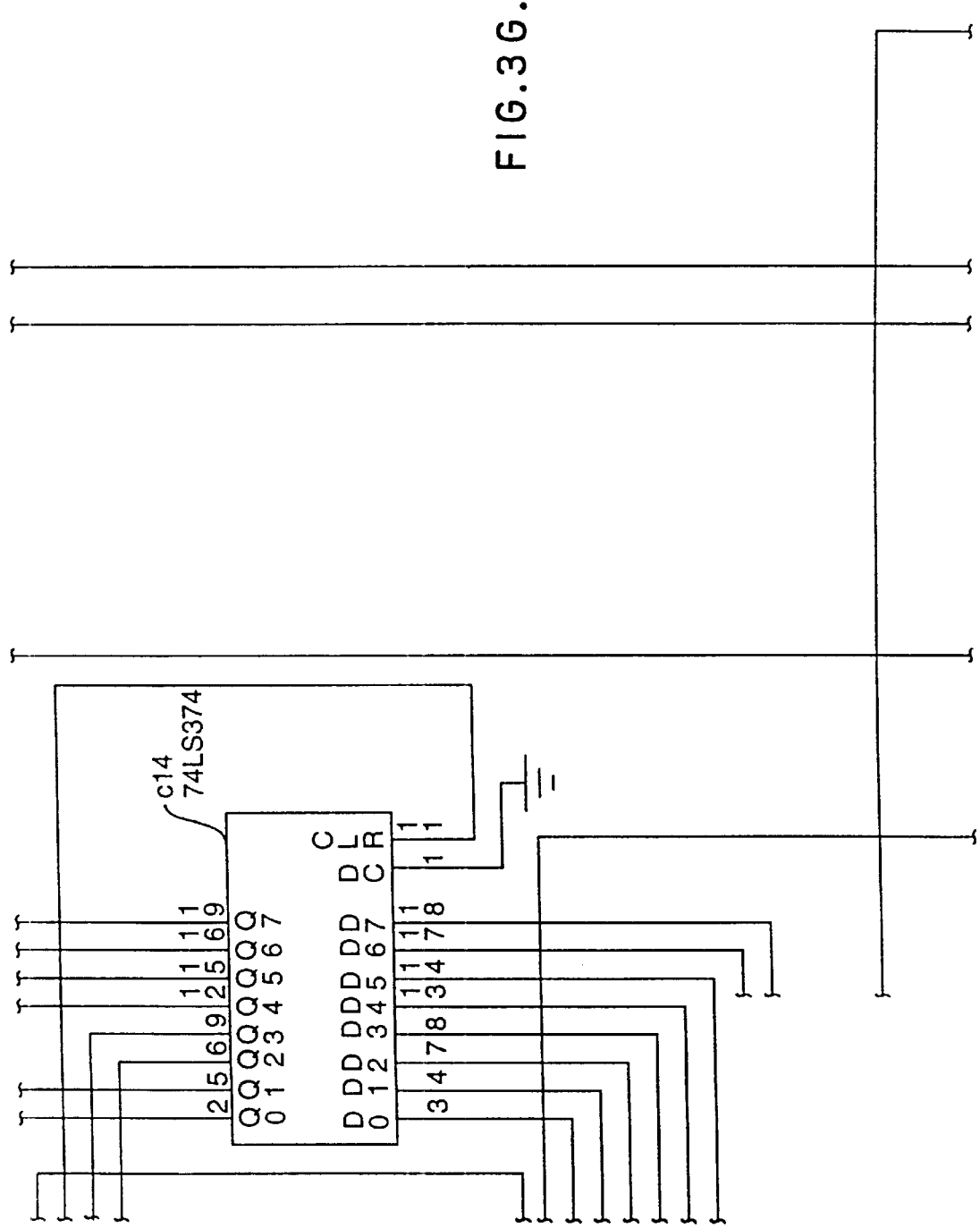

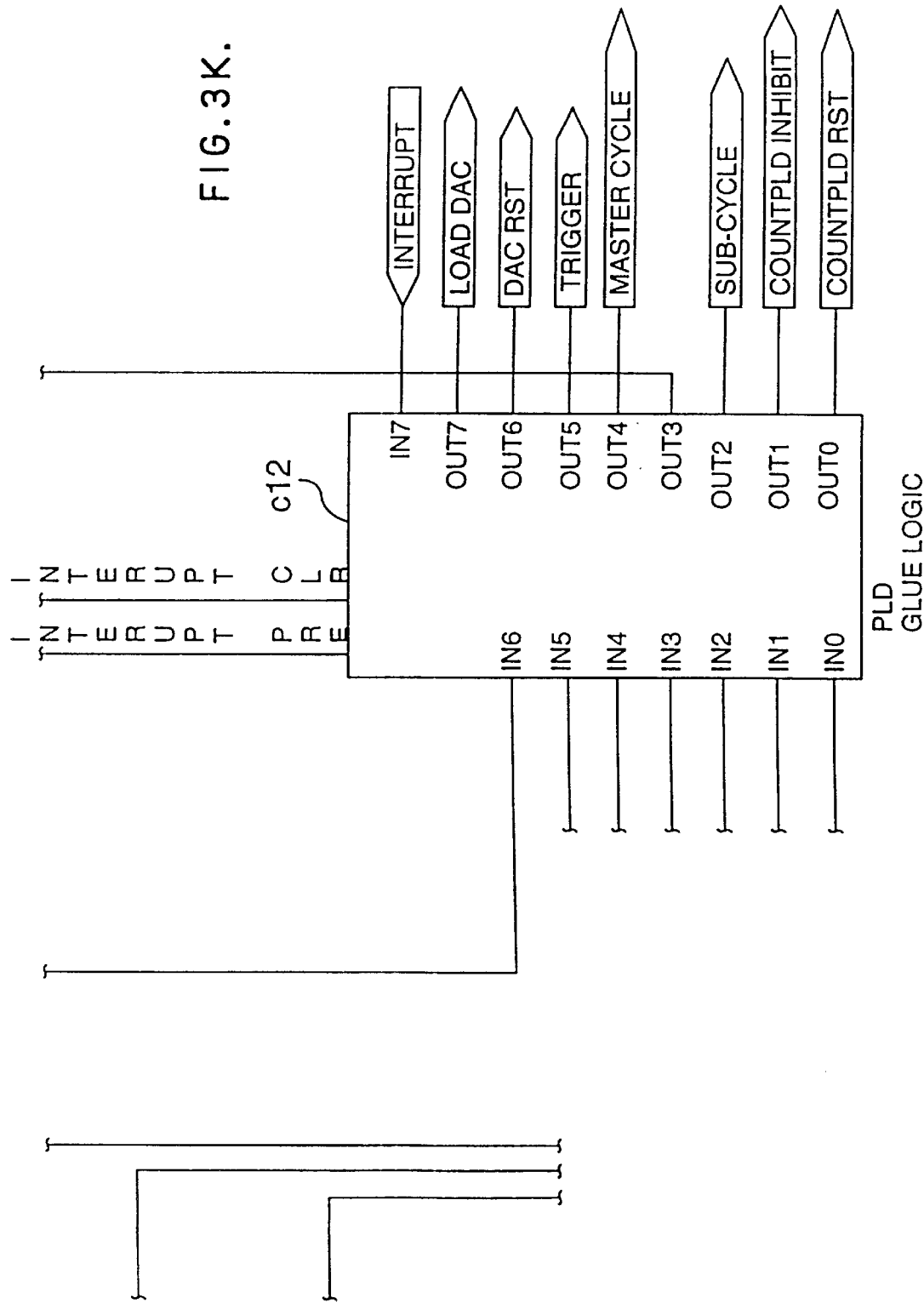

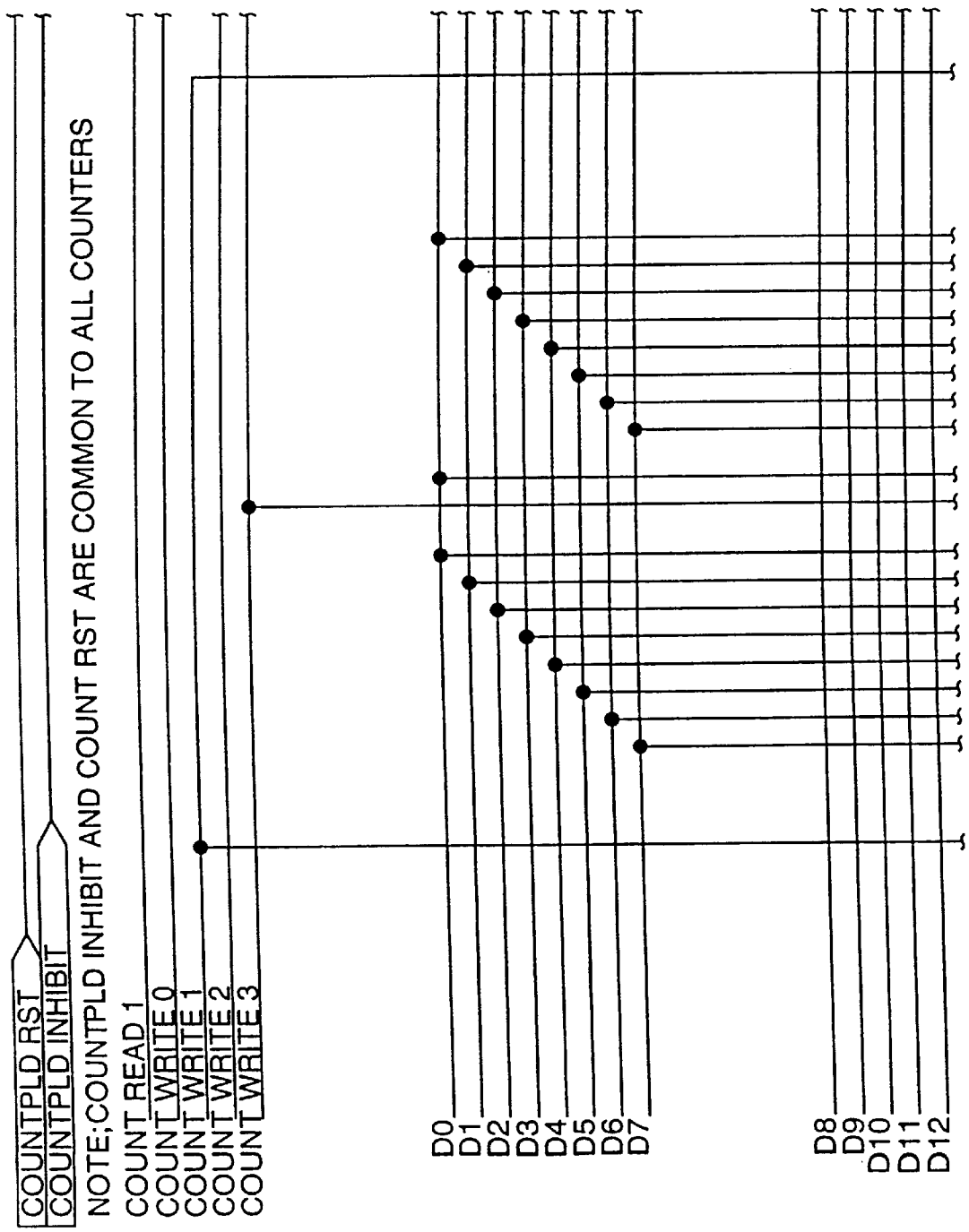

|FIG.5A.|FIG.5B.|FIG.5C.|
|---|---|---|
|FIG.5D.|FIG.5E.|FIG.5F.|
| FIG.5G.|FIG.5H.|FIG.5I.|FIG.5J.|
|---|---|---|---|
|FIG.5K.|FIG.5L.|FIG.5M.|FIG.5N.|
FIG.5.
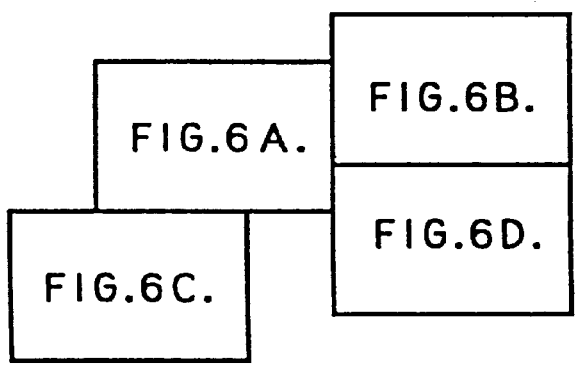
FIG.6.
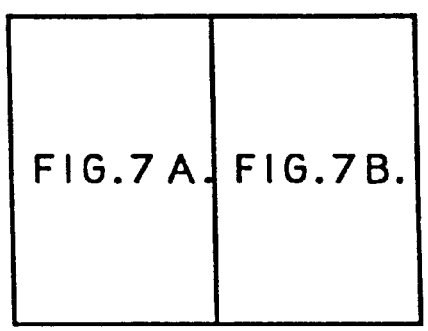
FIG.7.
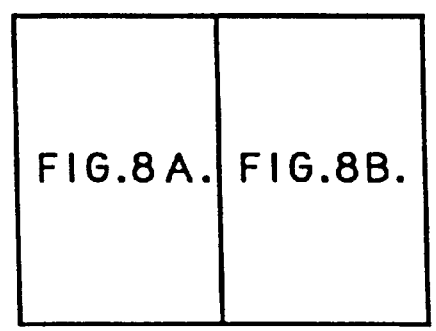
FIG.8.

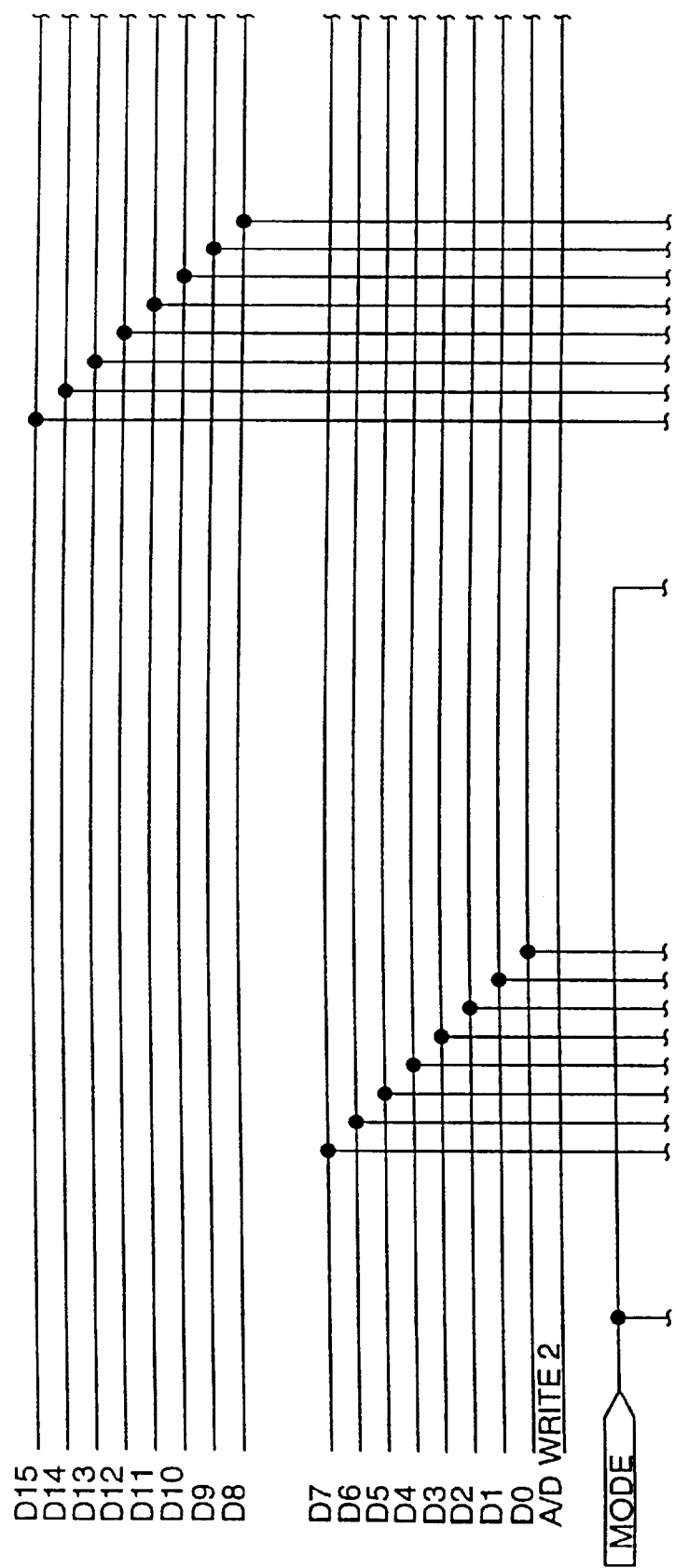

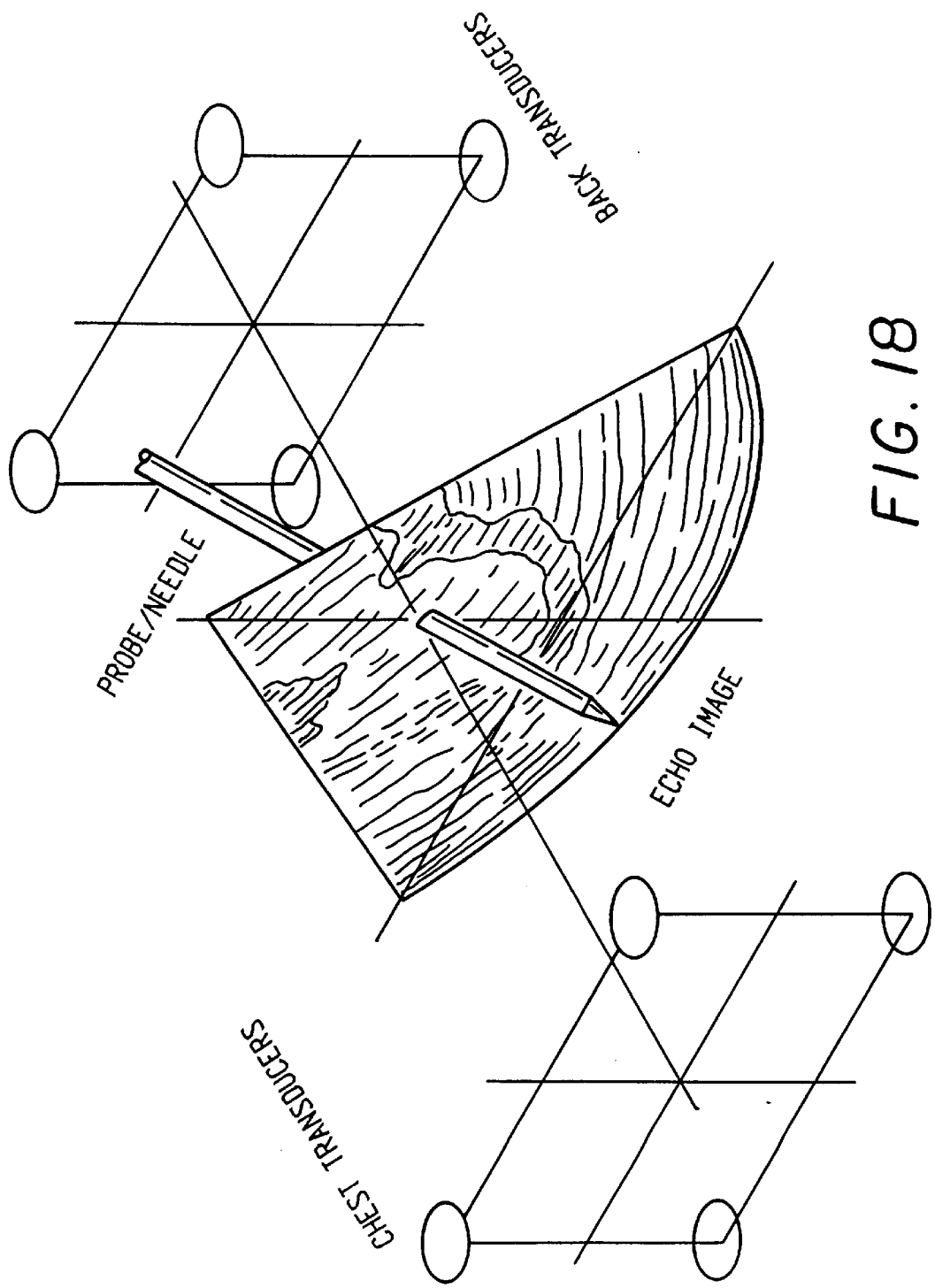

METHOD FOR CARRYING OUT A MEDICAL PROCEDURE USING A THREE-DIMENSIONAL TRACKING AND IMAGING SYSTEM

RELATED APPLICATIONS

The present application is a continuation-in-part (CIP) of U.S. application Ser. No. 08/812,518 filed Mar. 7, 1997, now U.S. Pat. No. 5,797,849, which is a continuation-in-part (CIP) of International Application No. PCT/CA96/00194, filed Mar. 26, 1996, which is a continuation-in-part (CIP) of U.S. application Ser. No. 08/411,959 filed Mar. 28, 1995, now U.S. Pat. No. 5,515,853.

FIELD OF THE INVENTION

This invention relates in general to a method for carrying out medical procedures, and more particularly to a method for carrying out medical procedures using a 3-D locating and imaging system.

BACKGROUND OF THE INVENTION

Using the time-of-flight principle of high frequency sound waves, it is possible to accurately measure distances within an aqueous medium, such as inside the body of a living being during a surgical procedure. High frequency sound, or ultrasound, is defined as vibrational energy that ranges in frequency from 100 kHz to 10 MHz. The device used to obtain three-dimensional measurements using sound waves is known as a sonomicrometer. Typically, a sonomicrometer consists of a pair of piezoelectric transducers (i.e., one transducer acts as a transmitter while the other transducer acts as a receiver). The transducers are implanted into a medium, and connected to electronic circuitry. To measure the distance between the transducers, the transmitter is electrically energized to produce ultrasound. The resulting sound wave then propagates through the medium until it is detected by the receiver.

The transmitter typically takes the form of a piezoelectric crystal that is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver also typically takes the form of a piezoelectric crystal (with similar characteristics to the transmitter piezoelectric crystal), that detects the sound energy produced by the transmitter and begins to vibrate in response thereto. This vibration produces an electronic signal in the order of millivolts, that can be amplified by appropriate receiver circuitry.

The propagation velocity of ultrasound in an aqueous medium is well documented. The distance traveled by a pulse of ultrasound can therefore be measured simply by recording the time delay between the instant the sound is transmitted and when it is received.

Prior art ultrasound measurement systems suffer from a number of shortcomings which limit their utility. Firstly, conventional sonomicrometers use analog circuitry to transmit and receive signals (e.g., phase capacitative charging circuits). The voltage representing the measured distance is then output to a strip chart recorder in analog form. This data must then be digitized for computer analysis.

Secondly, conventional ultrasound measurement systems use analog potentiometers to adjust the inhibit time and the threshold voltage that triggers the receiver circuits. This often requires the use of an oscilloscope. Each time the sonomicrometer is used, these settings must be manually set and adjusted in order to tune the system. This can be time consuming and annoying. As a whole, the function of the tracking system cannot be changed. The repetition frequency is fixed, regardless of the number of channels used, and the tracking system is therefore very limited in terms both of the distances that can be measured, and the temporal precision with which the sonomicrometer system operates.

Thirdly, conventional sonomicrometers feature pairs of transmitter and receiver crystals that are energized sequentially at fixed repetition rates. As such, prior art tracking systems lack experimental flexibility. For example, before a pair of crystals is implanted in the medium (e.g., a bodily structure, such as a human organ), the user must decide the function of each crystal; similarly, the user must determine which distances are to be measured by which crystal pair. This can be awkward because surgery often necessitates changes during the procedure. If either of the receiver or transmitter crystals malfunctions, the distance between them cannot be measured. Critical measurements can therefore be lost after a significant amount of effort is put into setting up the surgery.

Fourthly, conventional ultrasound tracking systems measure only a straight line distance between any isolated pair of crystals. Three-dimensional information is therefore impossible to acquire. Even if multiple combinations of distances could somehow be linked together, the inherently analog nature of the data would necessitate the use of additional, complex hardware.

Finally, conventional ultrasound tracking systems use discrete elements, such as threshold capacitors and potentiometers requiring large plug-in units to increase the number of channels. The systems are very large, usually two feet wide by 18" deep, and up to 12" high. Additional hardware such as strip chart recorders must be used, for visualization and subsequent processing. This can be very awkward given the space constraints at busy research institutes and hospitals.

The foregoing drawbacks to prior art systems limited their utility, and hence limit the practicality of using the systems to perform various types of medical procedures.

SUMMARY OF THE INVENTION

According to the present invention there are provided a variety for methods for carrying out a medical procedure using a three-dimensional tracking and imaging system. The 3-D tracking and imaging system provides enhanced functionality for diverse clinical and medical research applications.

The 3-D tracking and imaging system of the present invention uses modern day digital electronics in conjunction with an integrated personal computer. External A/D converters are not required, as the data is acquired digitally, directly from the sensors. Due to the speed of the controlling computer, the tracking system of this invention is capable of detecting distance increments as small as 19 $\mu$m. The acquired data can be displayed on the computer screen as it is being obtained, and can be saved to the computer's storage media with a simple key stroke. After an experiment or surgical procedure, the saved data can be examined and manipulated according to the user's specifications.

According to a preferred embodiment of the present invention, virtually every function of the 3-D tracking and imaging system is digitally controlled, and therefore very flexible. To begin, a set-up menu is generated which allows the user to select which transducers are active as well as the function of each channel. Next, a data display program permits the parameters of the transducer to be customized for specific applications. For example, if very few channels are being used, the repetition frequency can be increased so that data can be acquired at several Khz. On the other hand, if the system is being used in vitro, where persistent echoes from a container vessel may present a problem, the repetition frequency can be reduced to allow the echoes to attenuate between successive measurements.

The duration of the power delivered to the transducers can be reduced for precision work or increased if greater distances are required to be measured. The duration of the delay required to overcome electromagnetic interference between transducer leads is adjustable by means of a variable inhibit feature. Additionally, the number of samples displayed and stored in any given data save is variable according to the length of time that a user's protocol demands. Finally, the resolution of the displayed information is variable in conjunction with the degree of motion of the measured specimen. All of these functions are controlled digitally by means of custom designed digital cards or modules discussed in greater detail below, which, in turn, are software controlled.

Additional customized software is included in the 3-D tracking and imaging system of the present invention for post processing and visualizing the acquired data. In these routines, stray data points can be easily removed, three point filters can be applied for smoothing, level shifts can remove areas of discontinuity, channels can be derived, beat analyses can be performed, and automatic minimum/maximum level sensing can be applied. Finally, routines can be provided that allow animated data points in a Cartesian coordinate system while providing volumetric and position information.

The 3-D tracking and imaging system of the present invention overcomes the limitation of prior art transducer pairs. The present system can work with many individual transducers that can be energized sequentially at very high repetition rates, thereby giving the impression that several distances are being measured instantaneously. In reality, the distances are measured in sequence, but since the delay time between successive measurements is in the order of 100 microseconds, the measurements occur virtually simultaneously for most biological applications.

Additionally, the 3-D tracking and imaging system of the present invention provides the option of combining the transmitter and receiver circuitry into one transceiver. This provides a researcher with the freedom to affix an array of transducers to a test object (e.g., catheter, needle, probe, etc,) and then decide which transducers are to function as transmitters and which are to function as receivers. Moreover, this type of configuration does not need to be limited strictly to transmitter-receiver pairs. By using transceivers, the duty cycle between implanted transducers can automatically alternate between transmit and receive modes, so that every possible combination of distances between a group of transducers can be determined. This type of application is particularly useful for studies which require redundancy of measurement, as well as for establishing in vivo reference frames from which to base three-dimensional tracking.

The 3-D tracking and imaging system of the present invention is configurable into a true 3-D mode. In this configuration four or more transceivers are implanted within an object (i.e., specimen) in which distances are to be measured, thereby serving as a mobile reference frame. Multiple transmitters are then attached to the specimen at various locations. Since any three transceivers can send and receive signals, they essentially create an x,y plane. The fourth transceiver is then used to determine the z coordinate of the surrounding transducers by determining if the active transmitter lies above or below the reference plane.

Because the 3-D tracking and imaging system of the present invention uses modem day integrated circuitry and custom programmed logic chips, it is physically much smaller than prior art units. A large part of the system of the present invention is implemented within the user PC (personal computer). The entire unit is composed of three digital computer cards that plug directly into a standard AT computer mother board. A single cable connection connects the controlling computer and the discrete peripheral transmitter/receiver/transceiver unit. This convenient set-up drastically reduces the amount of experimental space required over prior art conventional units.

Moreover, the 3-D tracking and imaging system allows the position of a device being tracked to be displayed in relation to the surrounding environment using a 3-D template.

The present invention provides a variety of medical procedures which utilizes the unique features of the 3-D locating and imaging system.

BRIEF DESCRIPTION OF THE DRAWINGS

A detailed description of the preferred embodiment is provided herein below with reference to the following drawings, in which:

FIG. 2, comprising FIGS. 2A, 2B, 2C and 2D, is a schematic diagram of a computer interface architecture used on all digital cards or modules of the preferred embodiment;

FIG. 3, comprising FIGS. 3A, 3B, 3C, 3D, 3E, 3F, 3G, 3H, 3I, 3J, 3K, 3L, 3M, 3N, 3O, 3P and 3Q is a schematic diagram of a controller card architecture according to the preferred embodiment;

FIG. 4, comprising FIGS. 4A, 4B, 4C, 4D, 4E, 4F, 4G, 4H, 4I, 4J, 4K, 4L, 4M, 4N, 4O and 4P, is a schematic diagram of a counter card architecture according to the preferred embodiment;

FIG. 5, comprising FIGS. 5A, 5B, 5C, 5D, 5E, 5F, 5G, 5H, 5I, 5J, 5K, 5L, 5M and 5N is schematic diagram of an A/D card architecture according to the preferred embodiment;

FIG. 6, comprising

FIG. 7, comprising

FIG. 8, comprising

FIG. 18 is a 3-D scene showing a reference frame, location and direction of a surgical instrument and an ultrasound sector image;

DETAILED DESCRIPTION OF THE PREFERRED EMBODIMENT

Figure 1:
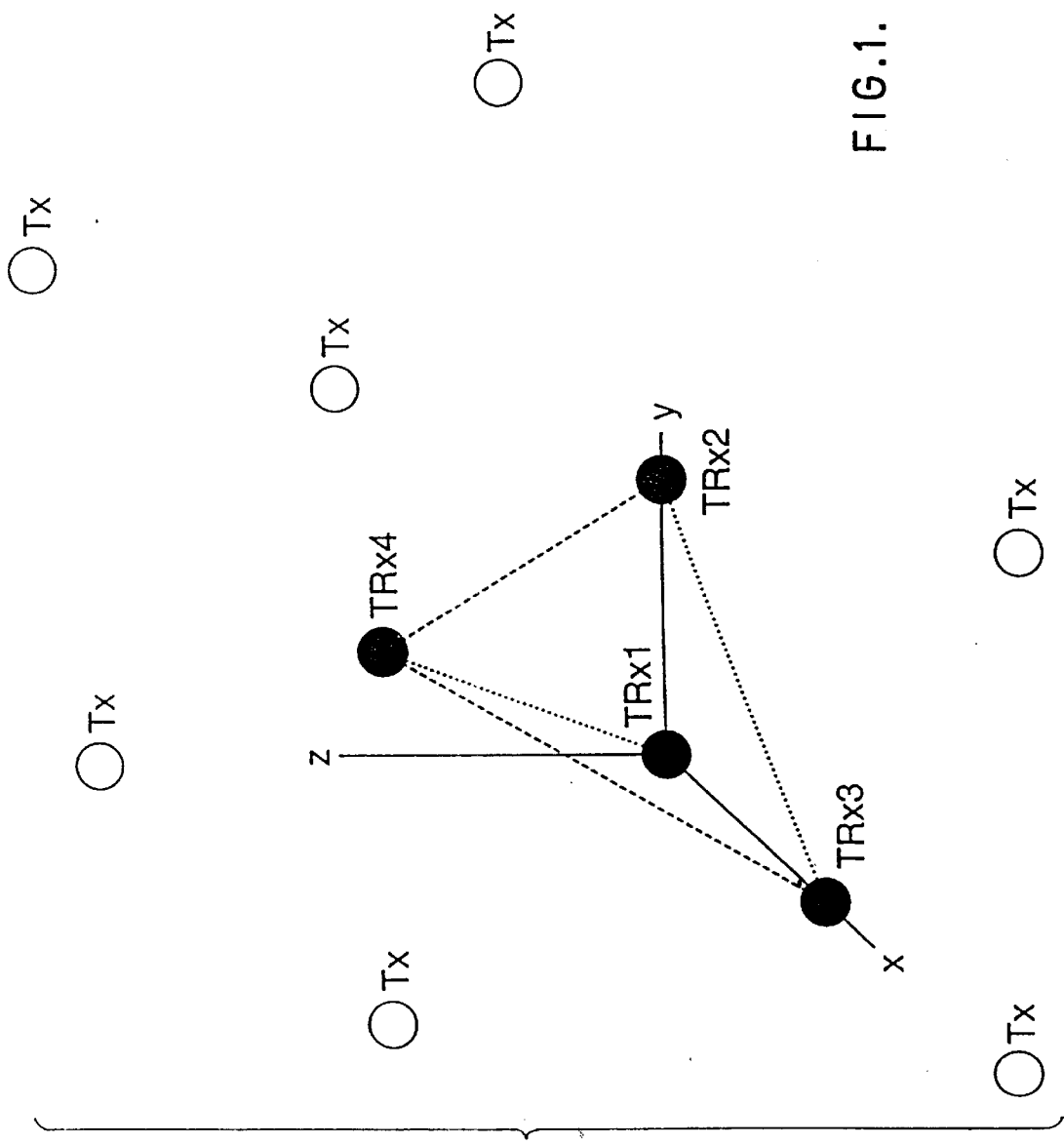
FIG. 1 is a schematic representation of four transducers in three-dimensional space, for tracking and triangulating the three-dimensional positions of each transducer, in accordance with the present invention.

As discussed above, the ultrasonic tracking system of the present invention utilizes a plurality of transceivers, each of which can be programmed to operate as a transmitter or a receiver. By utilizing four or more transceivers, full three-dimensional measurement capability is provided, as shown in FIG. 1. Any three transceivers (TRx1, TRx2 and TRx3) lay in a plane (i.e., the x,y plane). The fourth transceiver (TRx4) may then be used to determine the z coordinates of the surrounding transducers (i.e., multiple crystals Tx) by determining if an active one of the transmitter transducers lies above or below the reference plane established by transceivers TRx1, TRx2 and TRx3. Each of the many transmitters (Tx) attached to the specimens are sequentially fired, while all reference transceivers record the receiver signals. Since the distance from each transmitter to the reference plane created by the transceivers is known, the relative x, y, z, coordinates of the transmitters can be determined. This is done in real time on a personal computer (PC) with the use of triangulation. This method of networking the transducers is unique to the tracking system of the present invention, and permits the user to trace the three-dimensional motion of an object under investigation. Obviously, the greater the number of transmitters, the better is the reconstruction.

Specific applications of the ultrasonic tracking system which utilize three-dimensional tracking and triangulation, are discussed in greater detail below.

As indicated above, the ultrasonic 3-D tracking system according to the present invention is preferably fully integrated into the standard AT-style computer motherboard found in modern PCs. The three digital cards which comprise the majority of the hardware for the present invention, perform specific, modular functions in the overall operation of the unit. As such, each card is provided with a proper system interface structure in order to be compatible with the ISA architecture of the controlling processor.

Figure 2A:
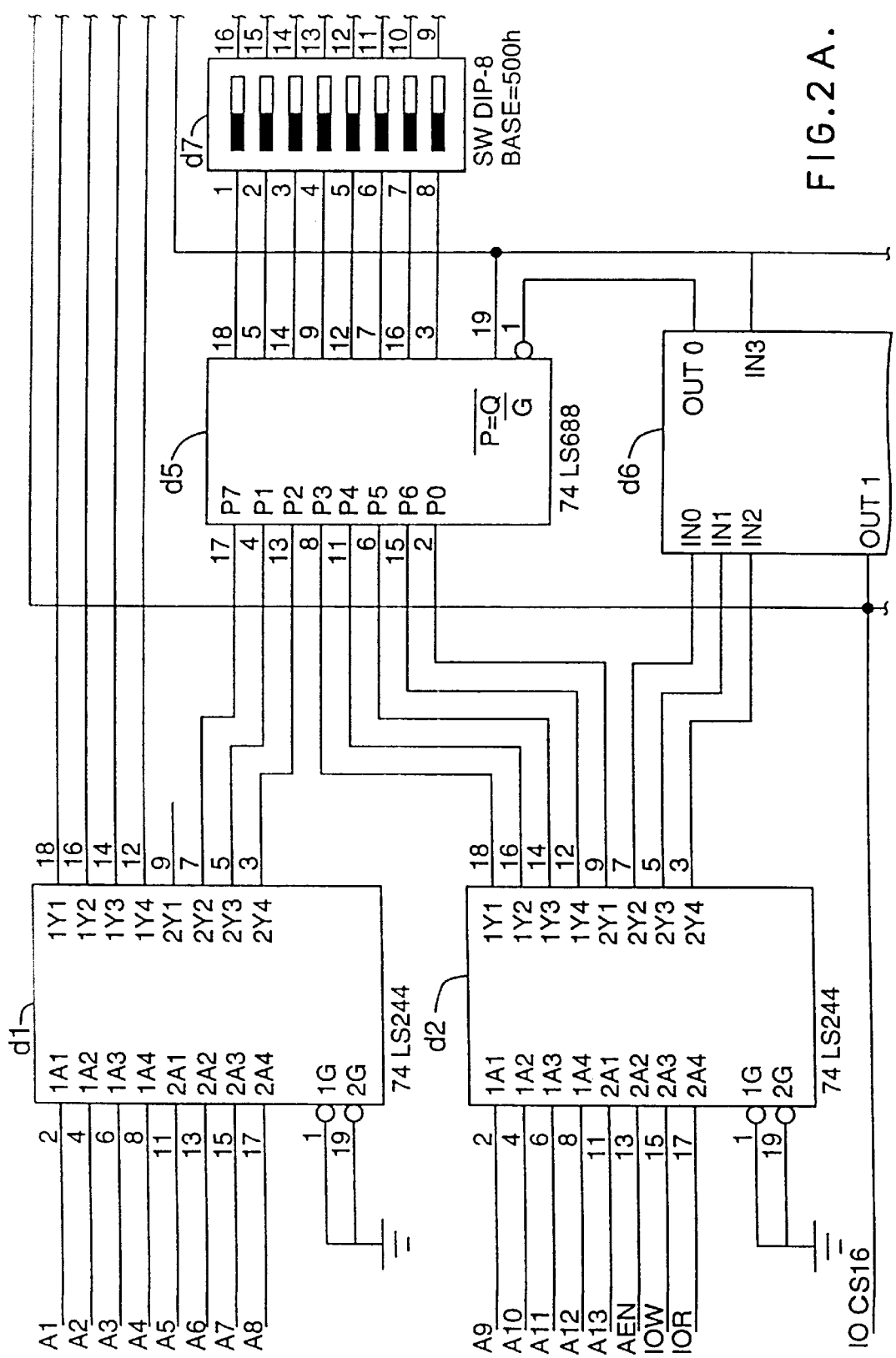
Figure 2B:
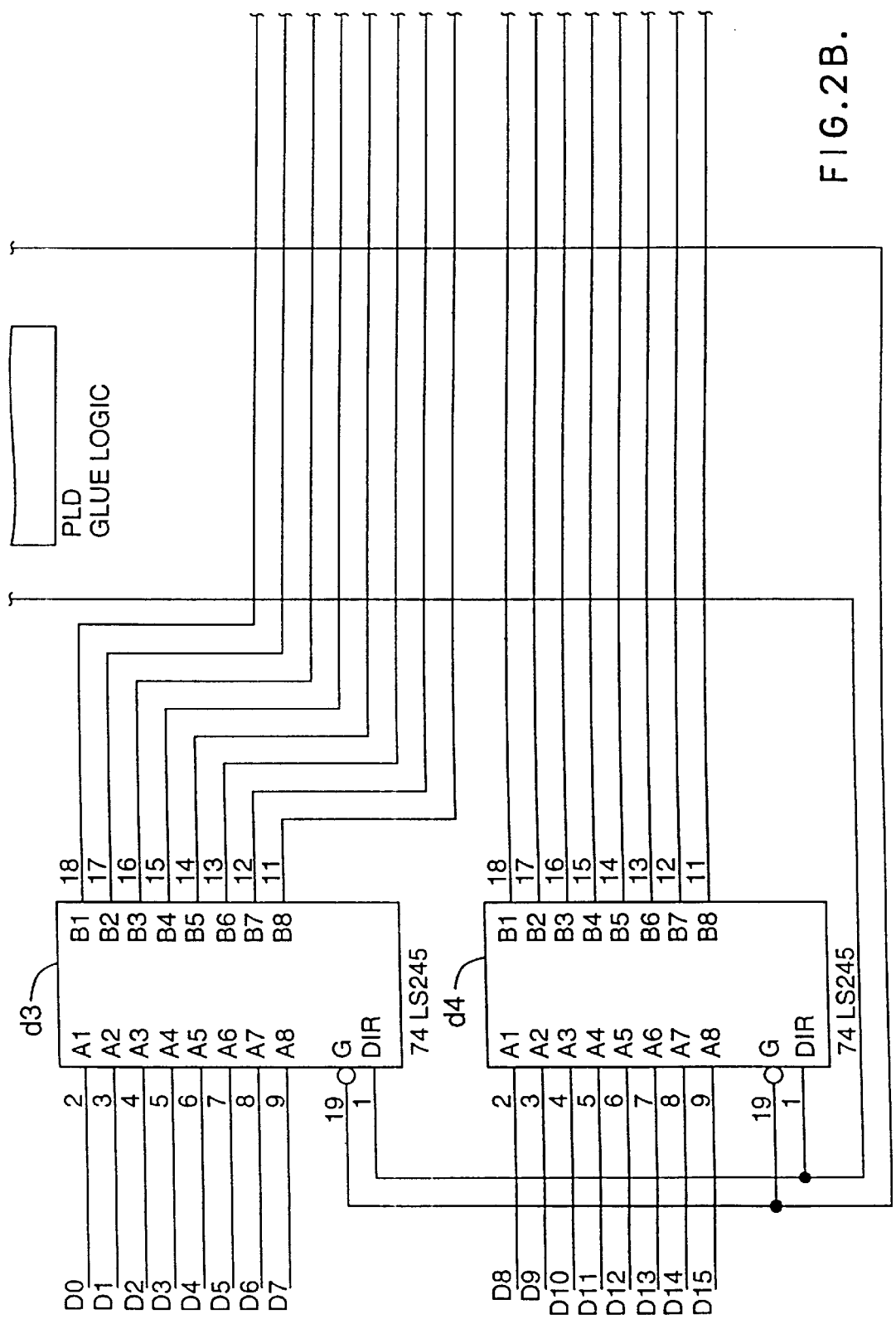
Figure 2D:
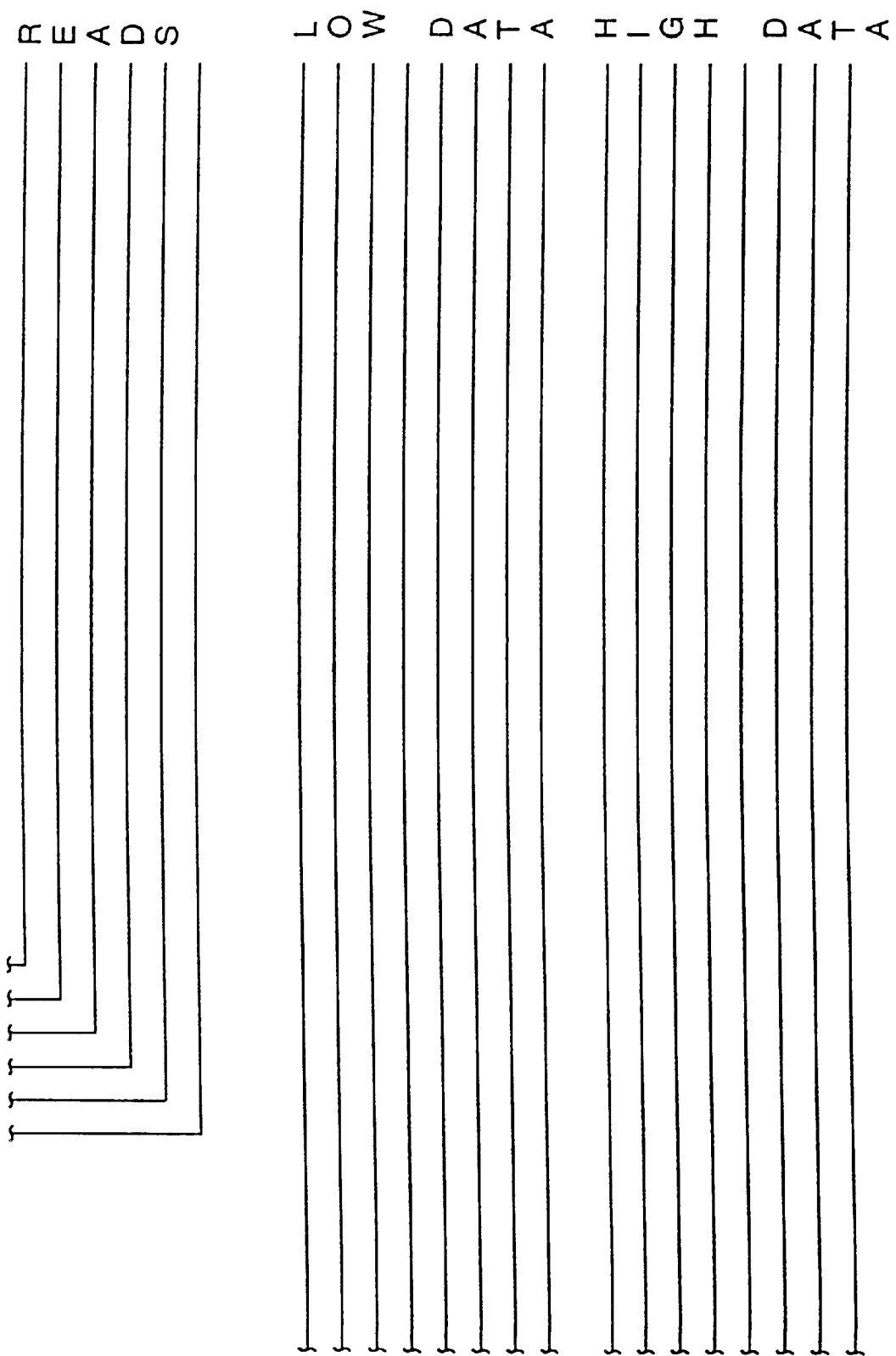
Figure 3B:
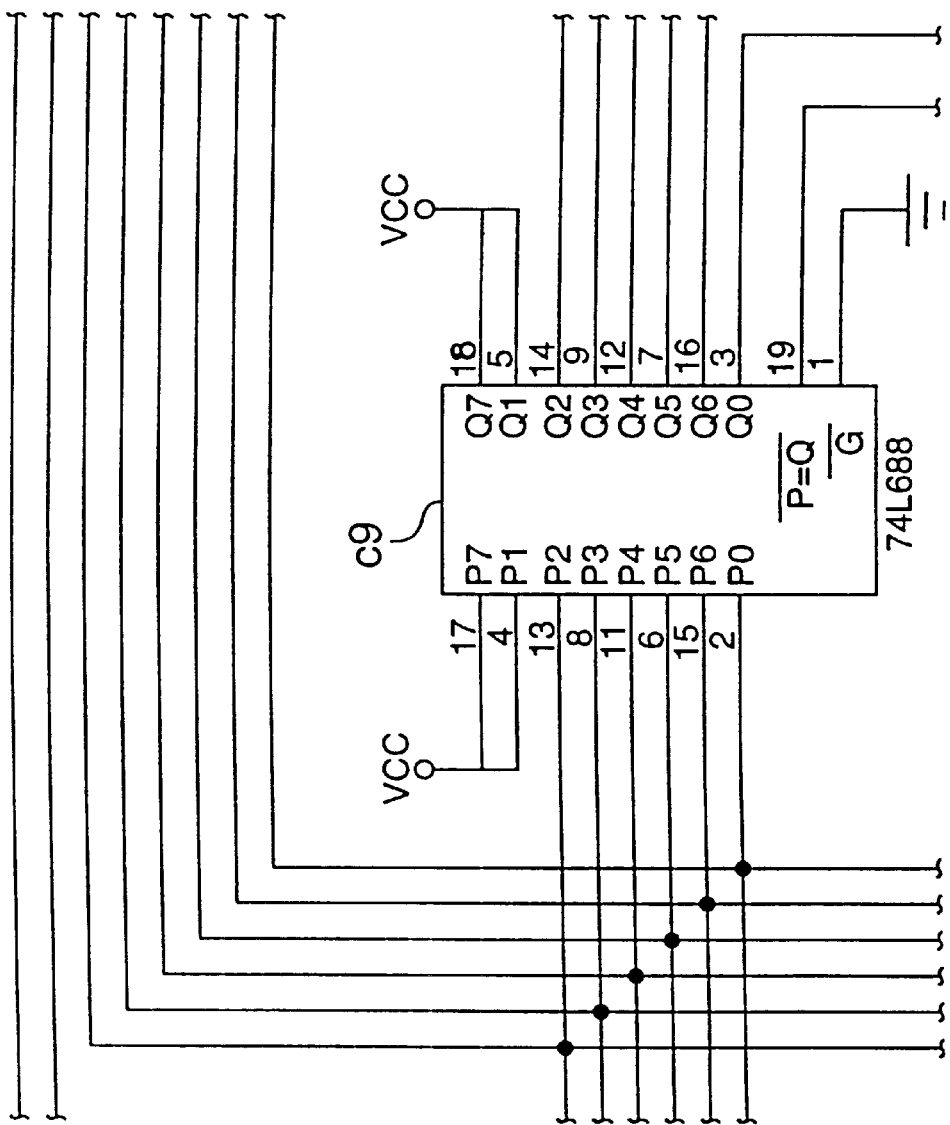
Figure 3C:
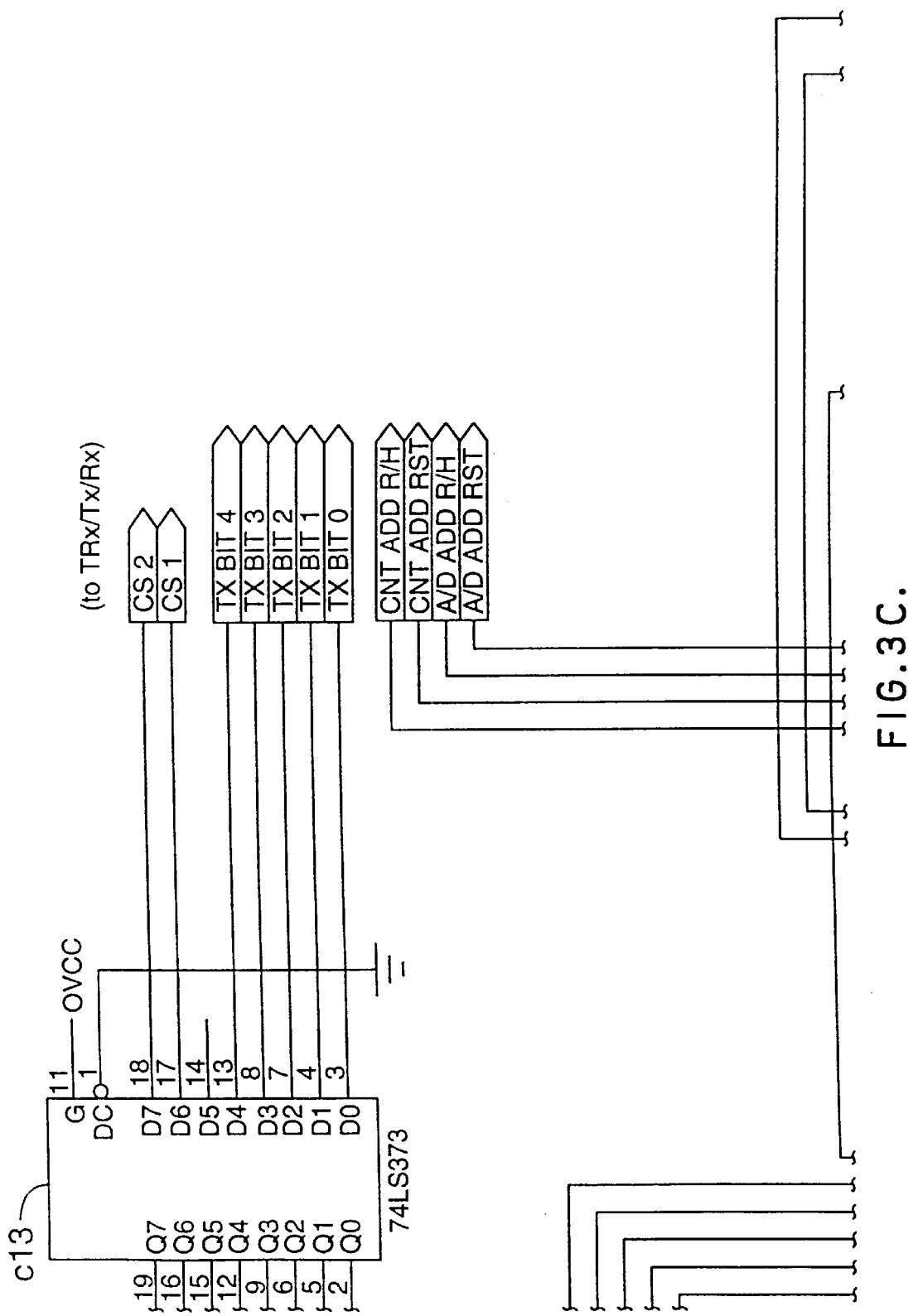
Figure 3E:
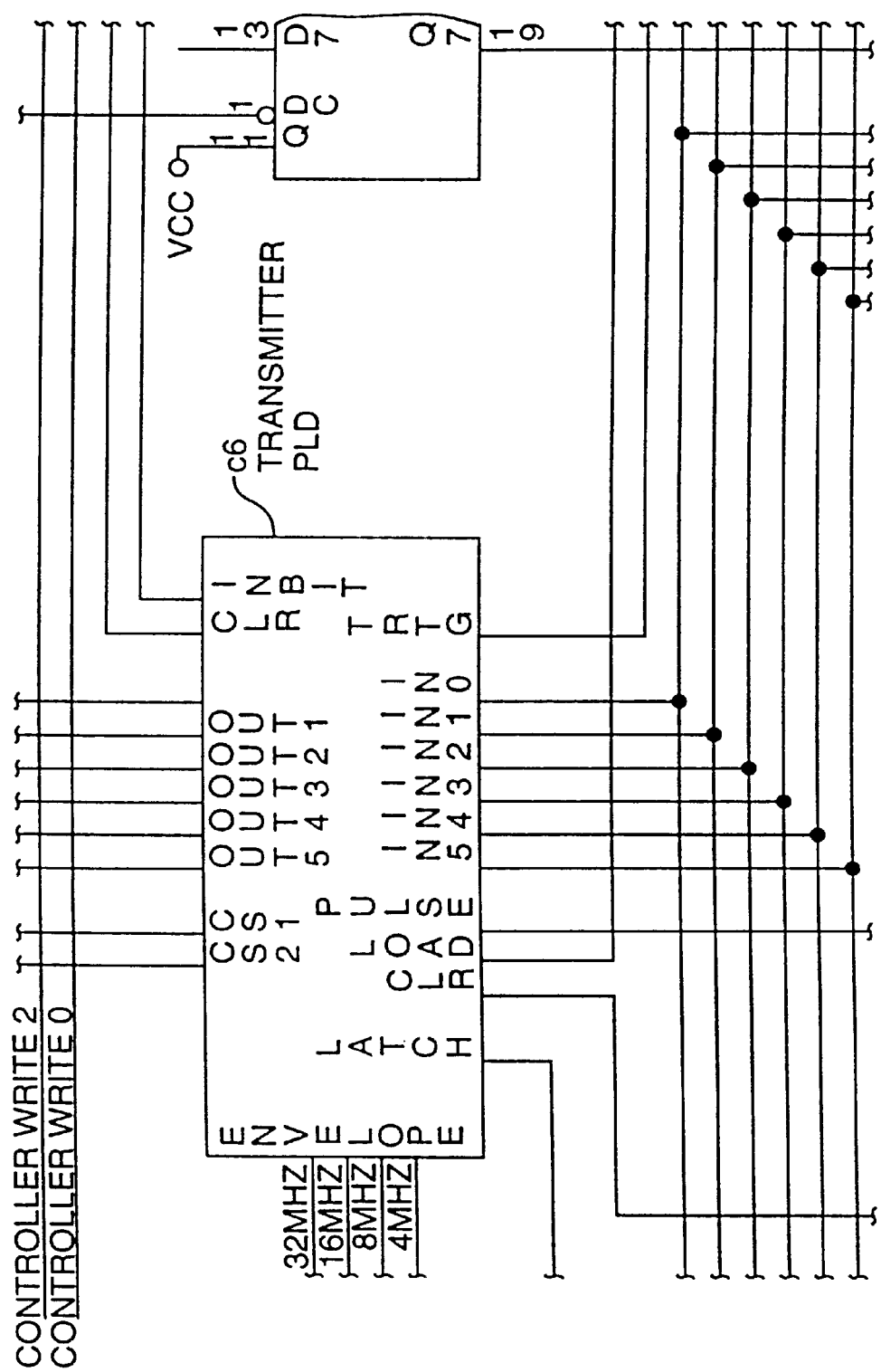
Figure 3F:
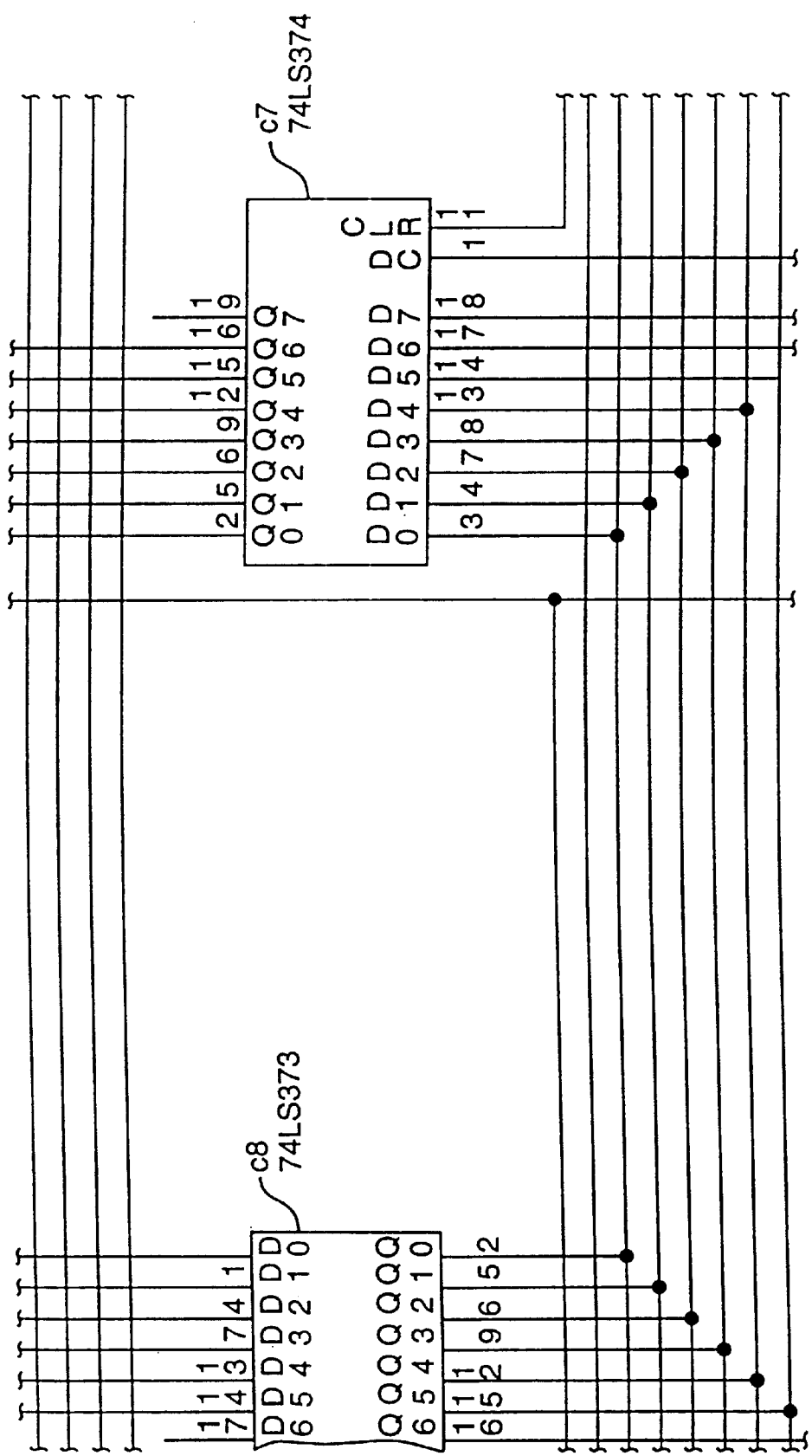
Figure 3H:
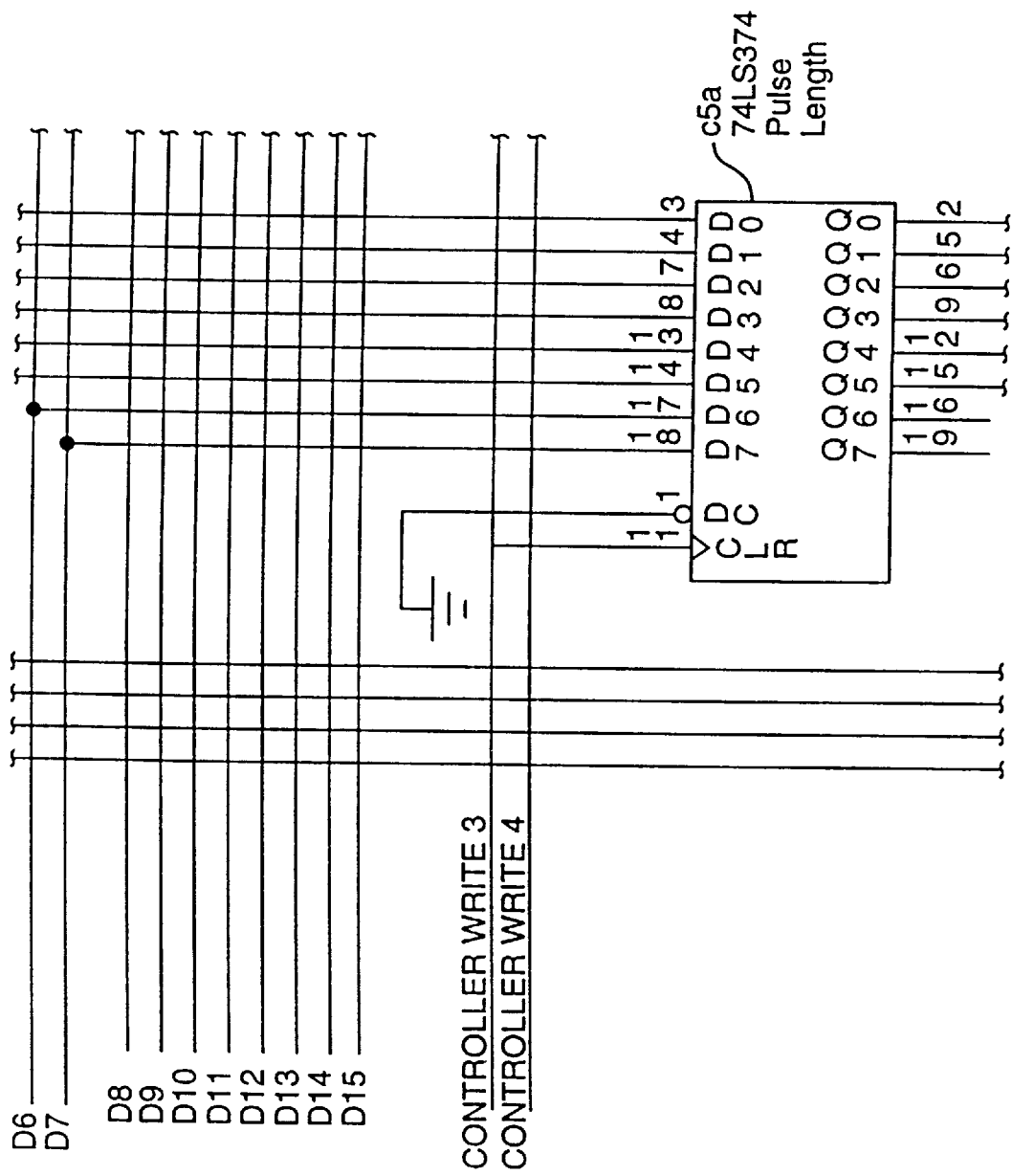
Figure 3I:
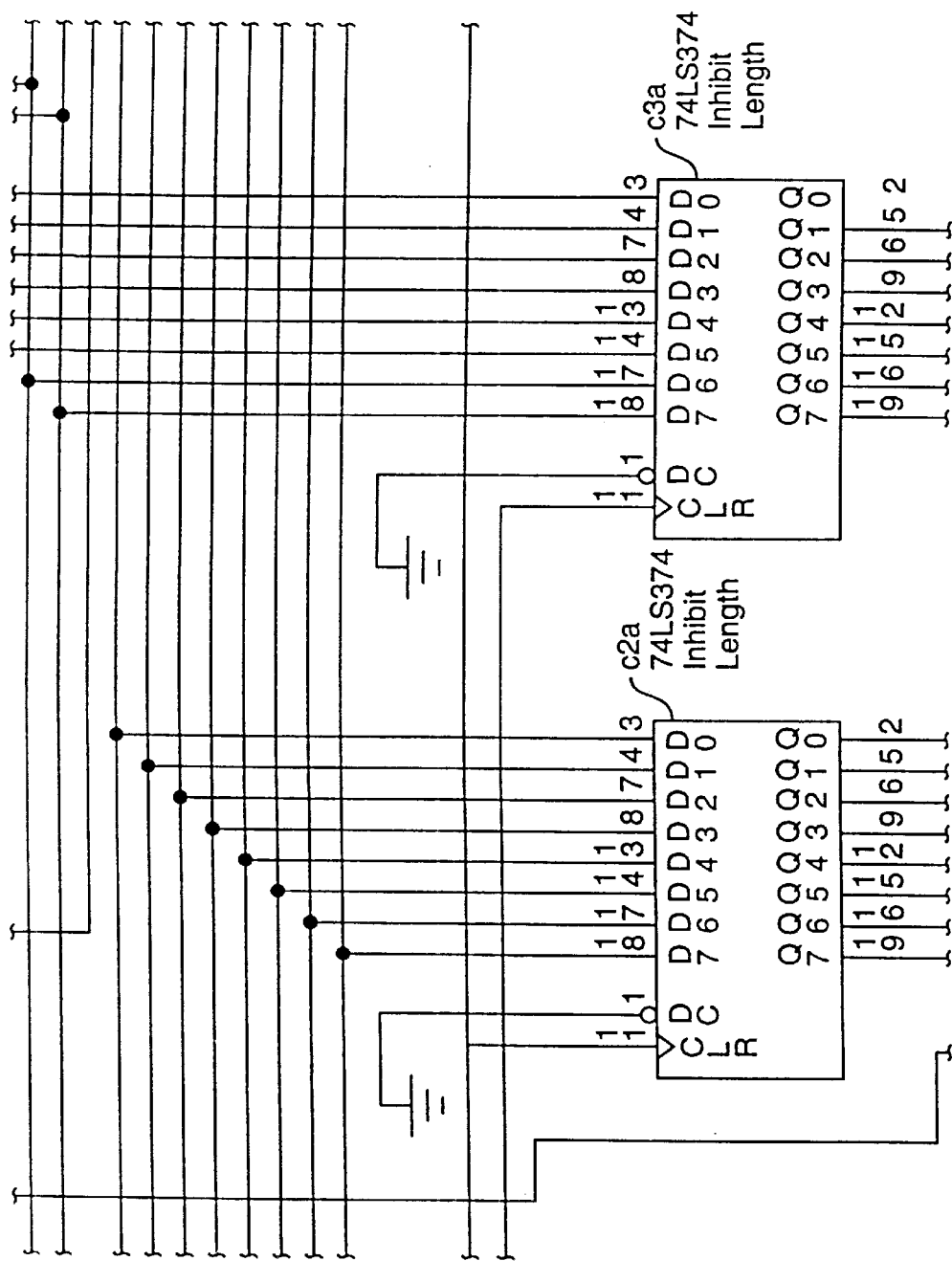
Figure 3J:
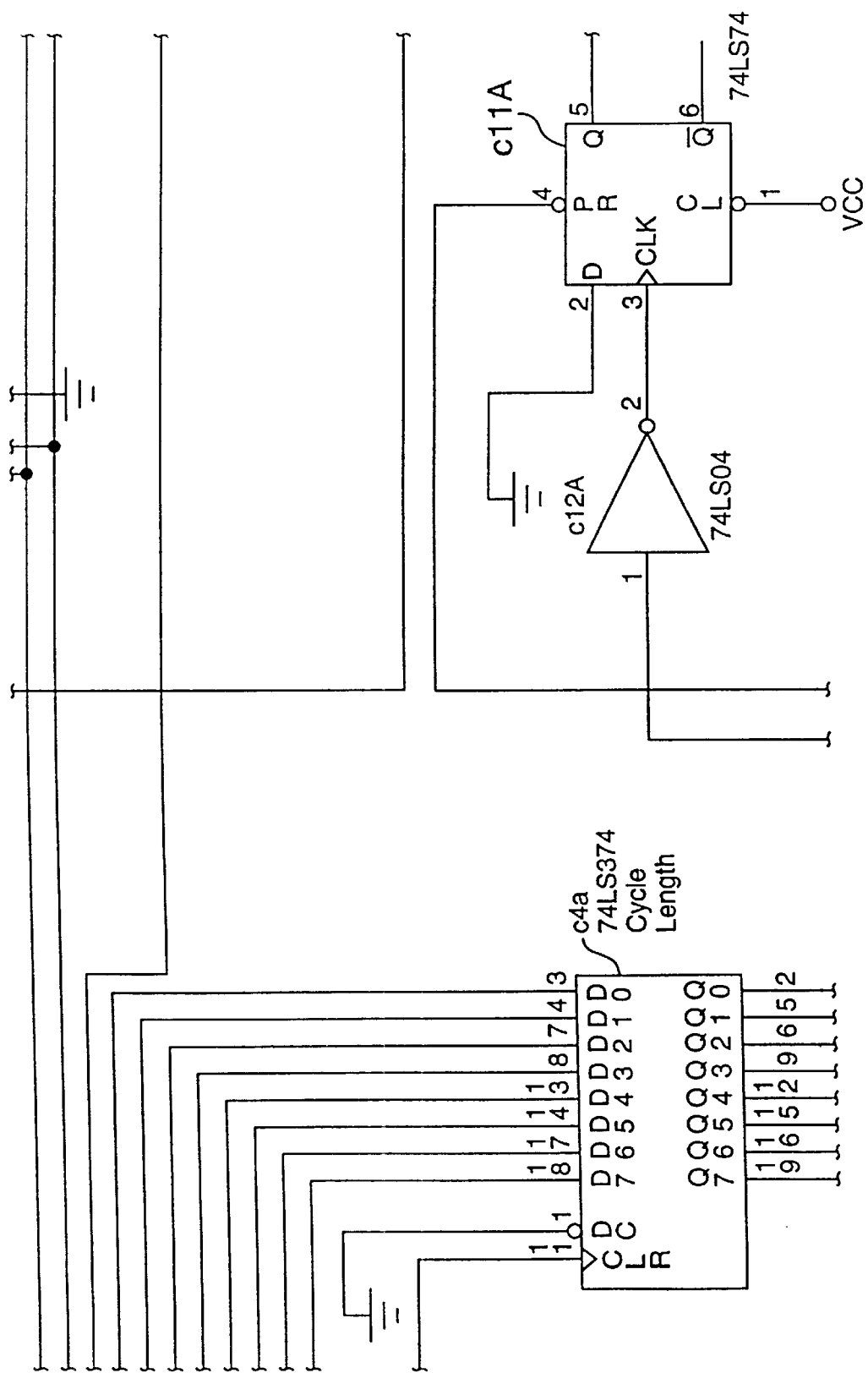
Figure 3L:
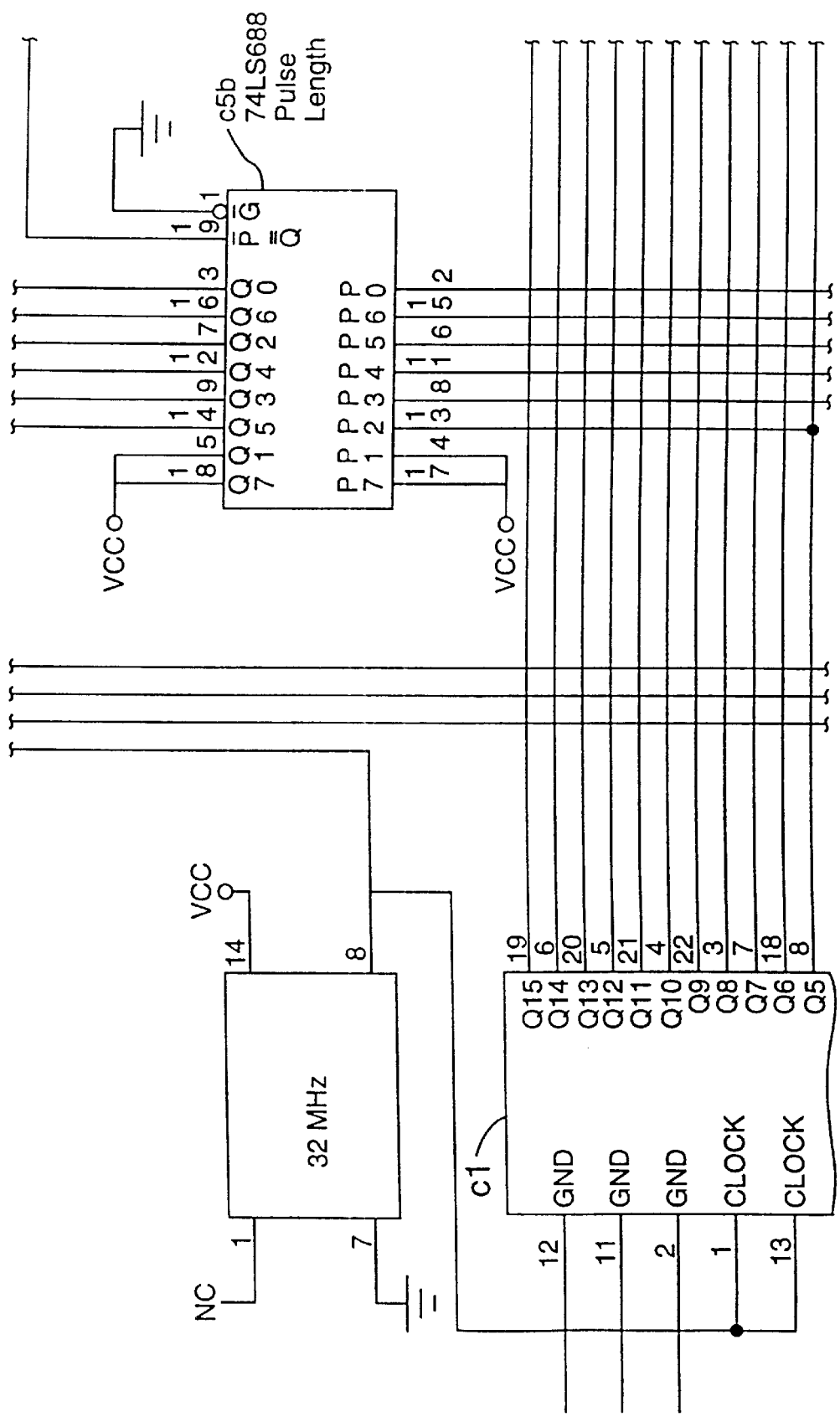
Figure 3M:
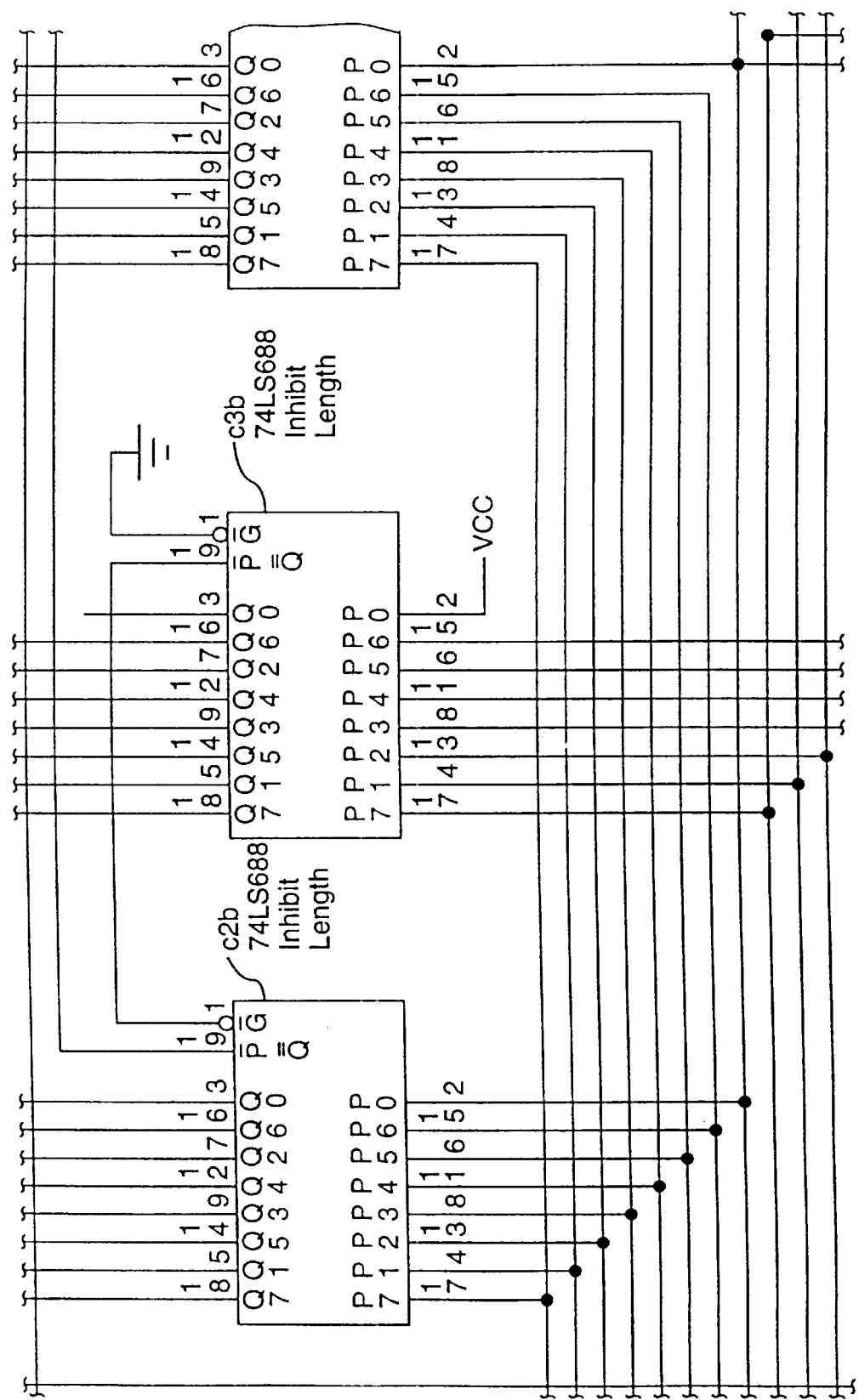
Figure 3N:
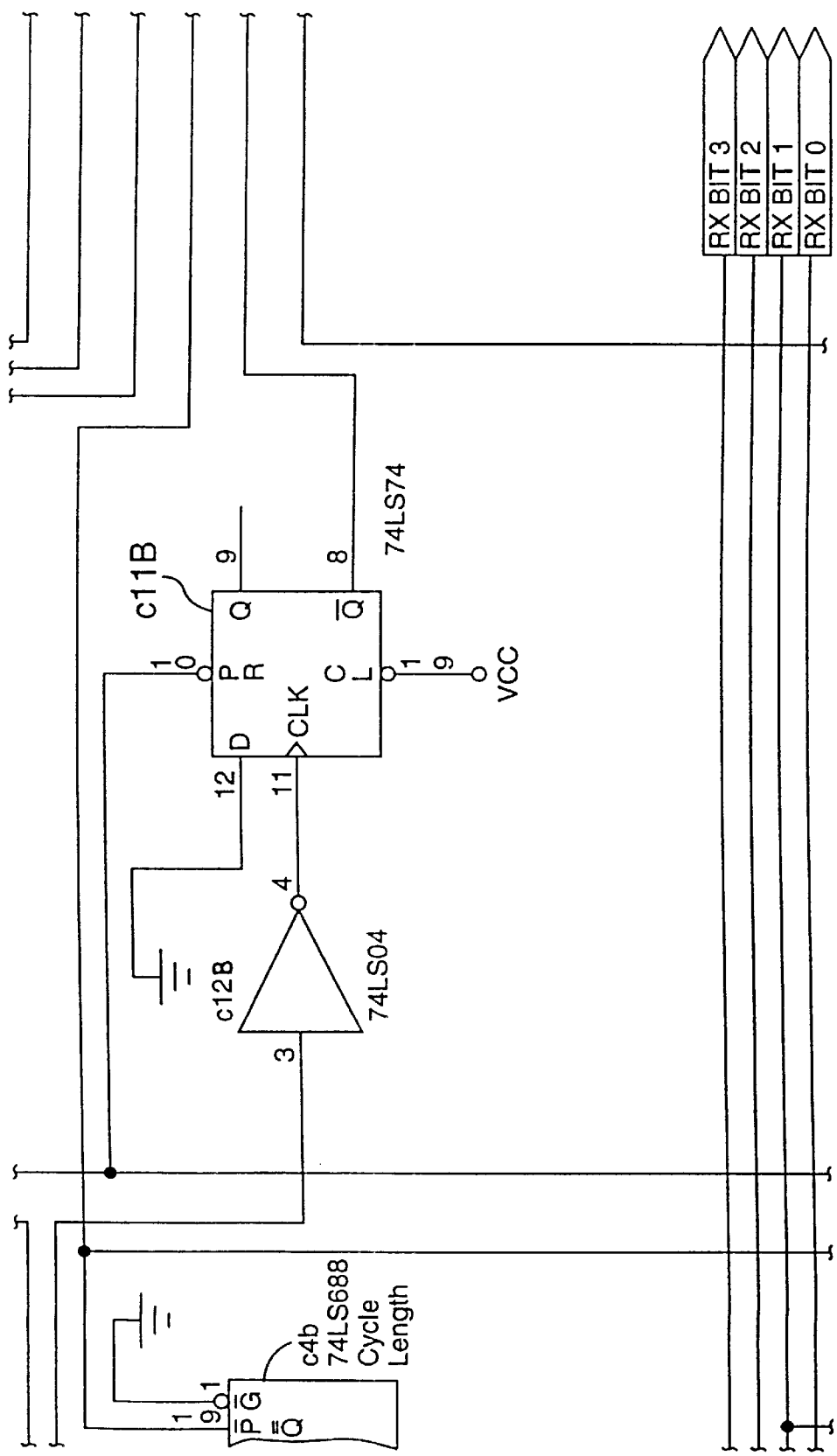
Figure 30:
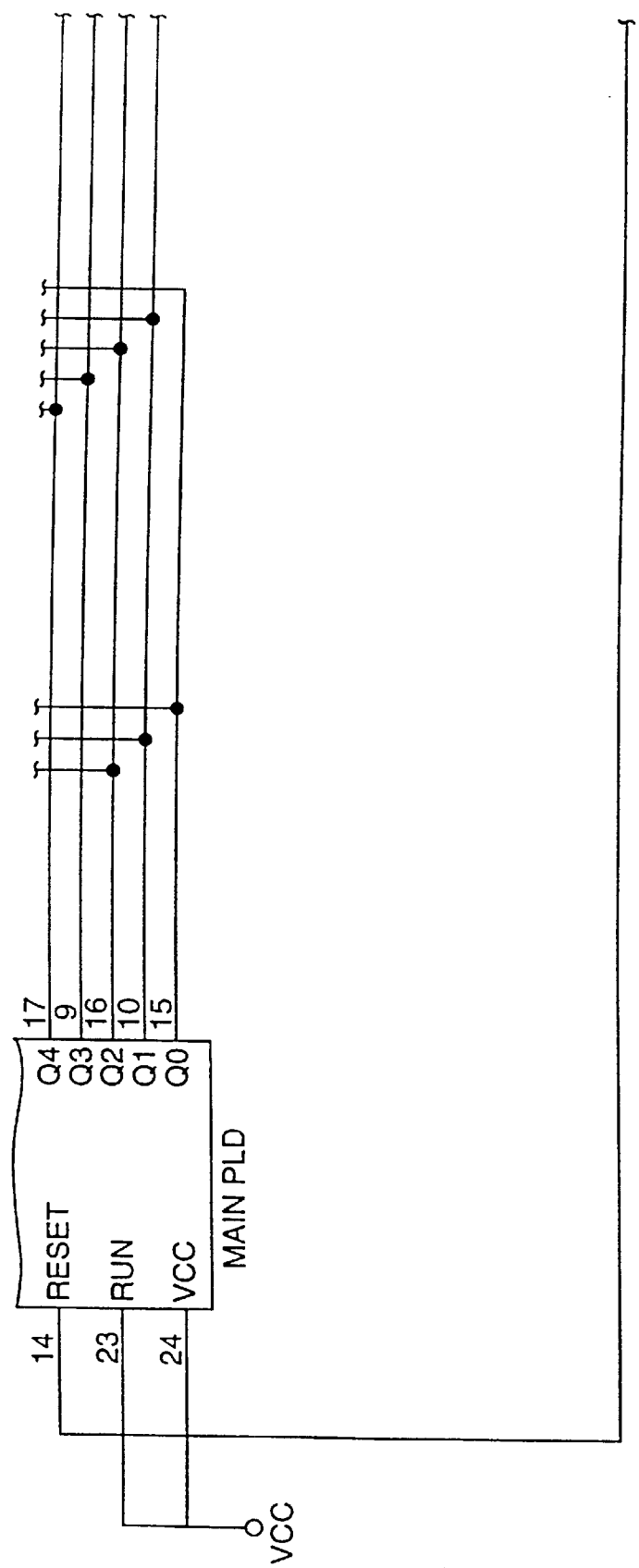
Figure 3P:
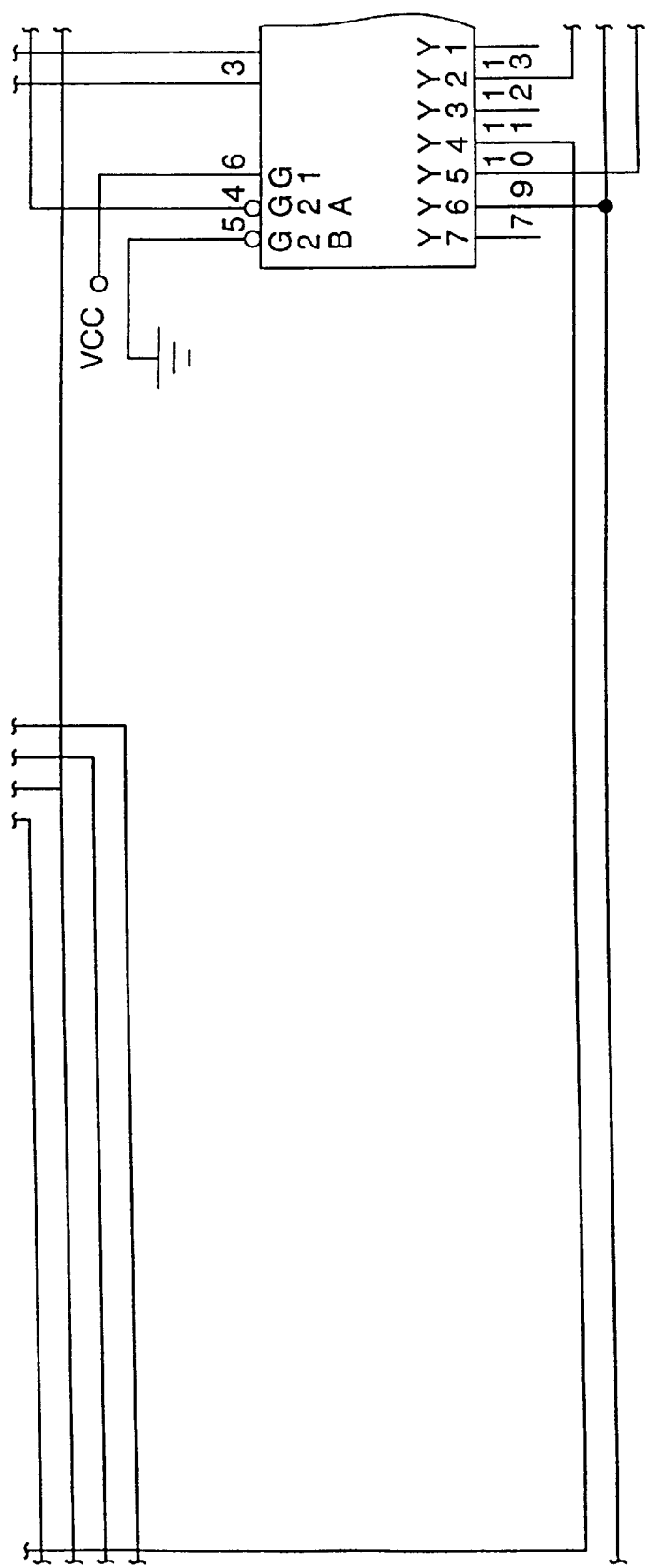
Figure 3Q:
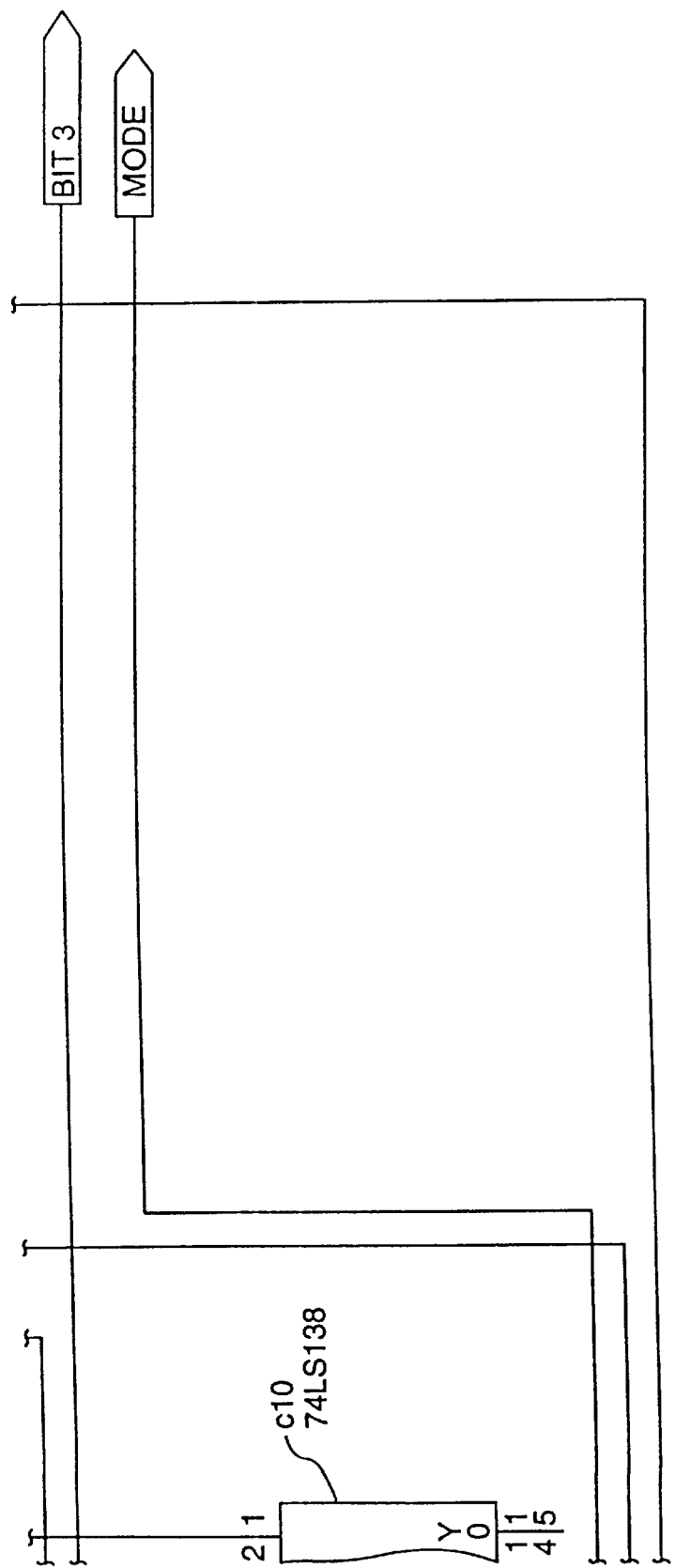
Figure 4B:
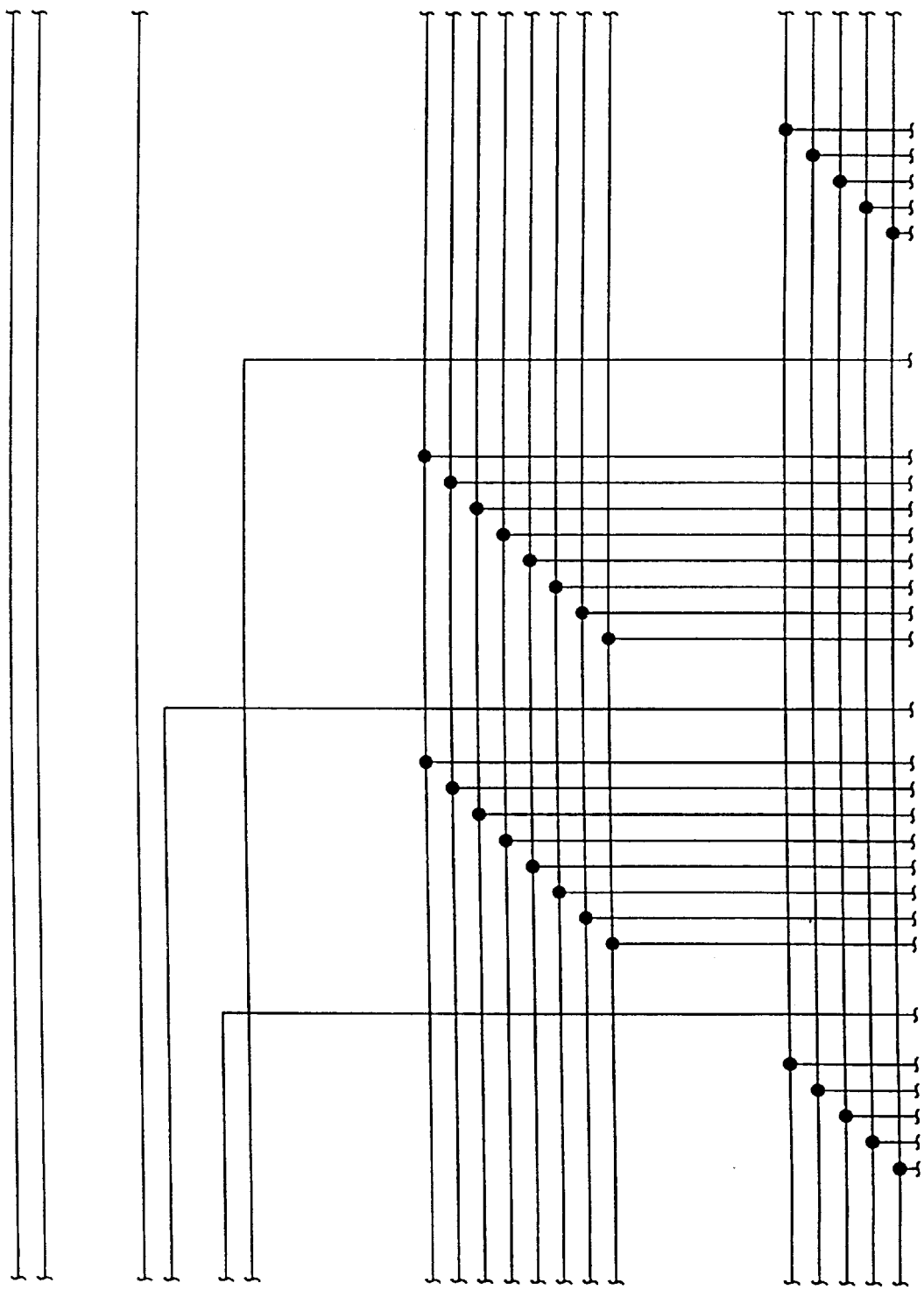
Figure 4C:
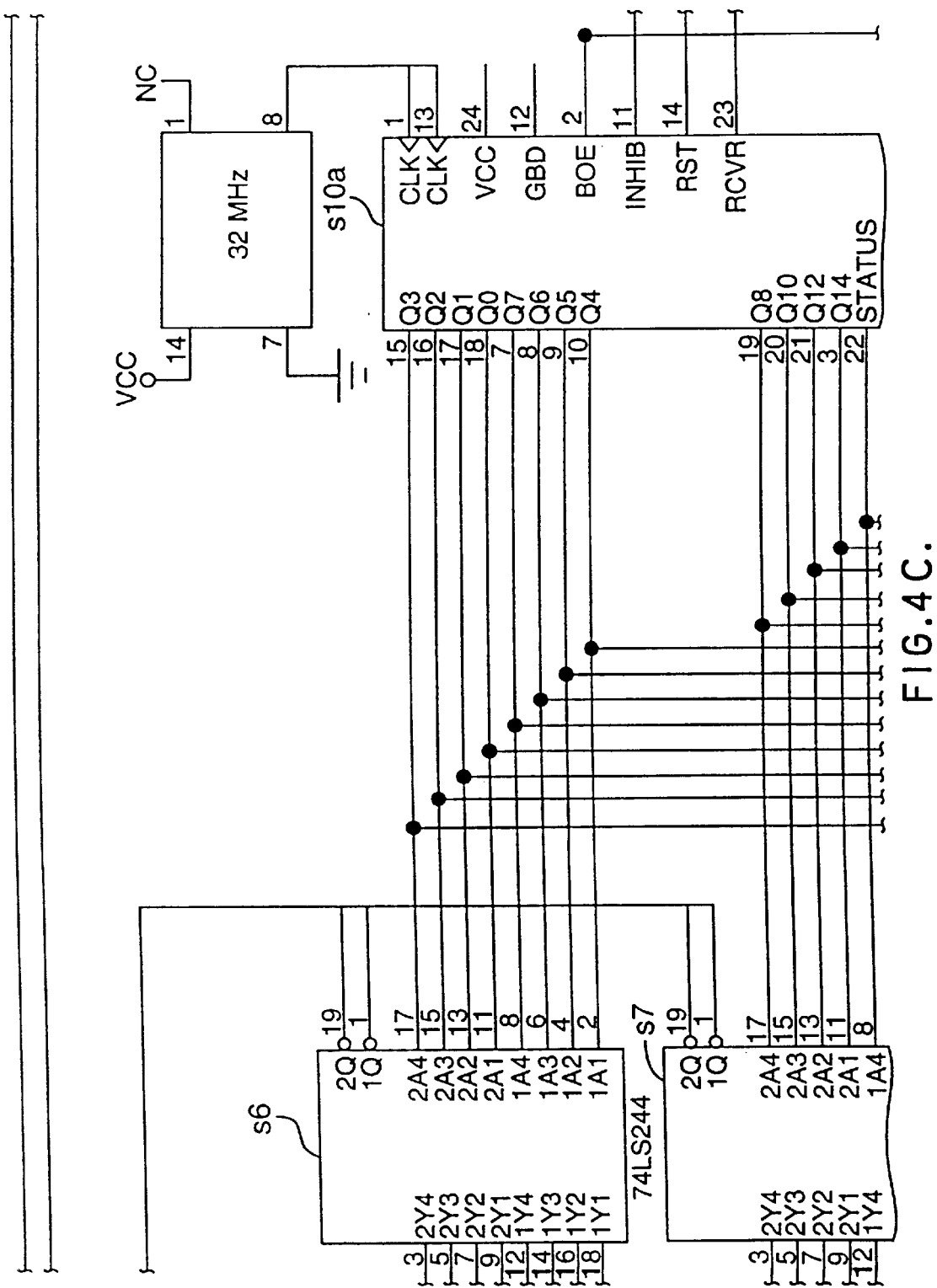
Figure 4D:
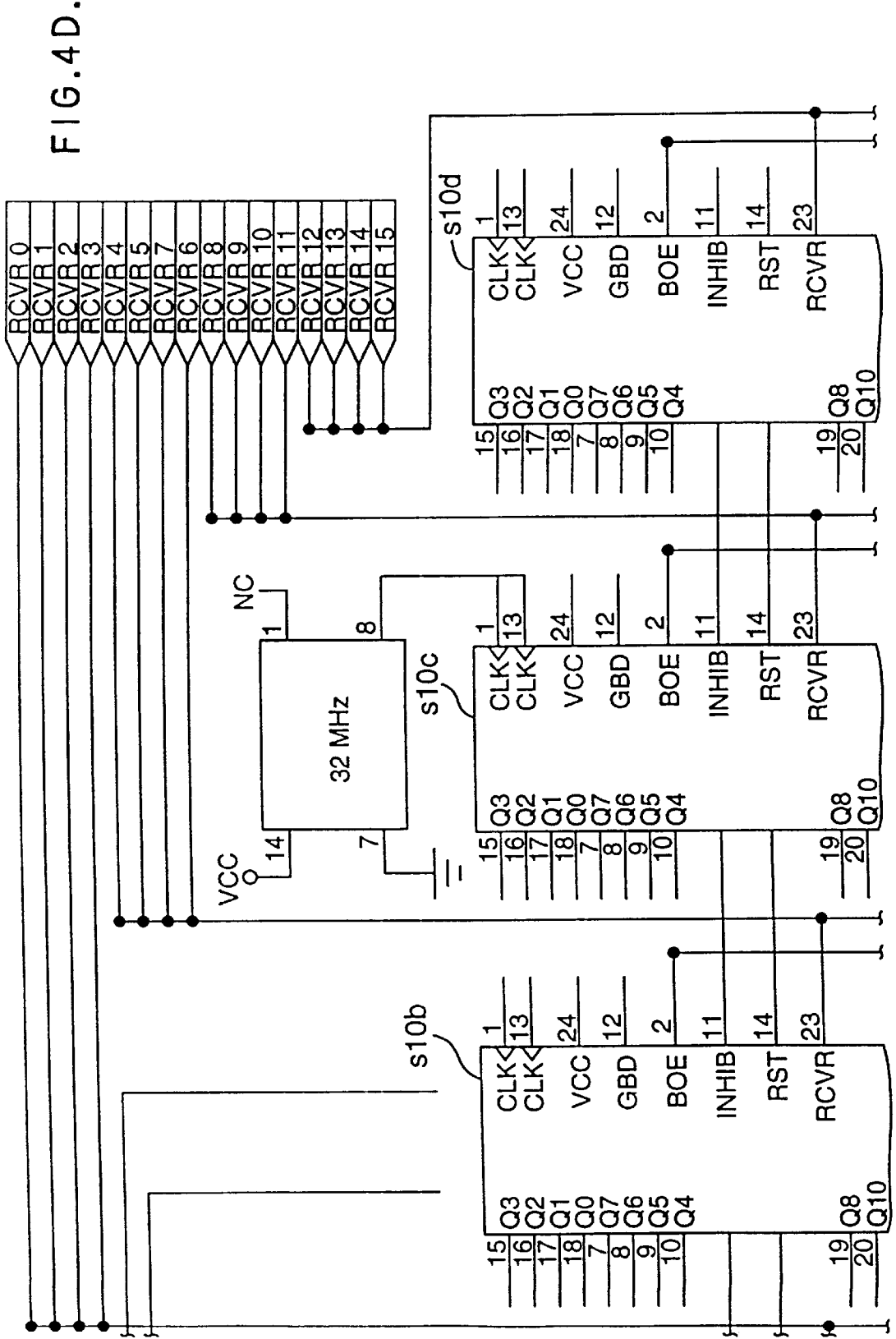
Figure 4E:
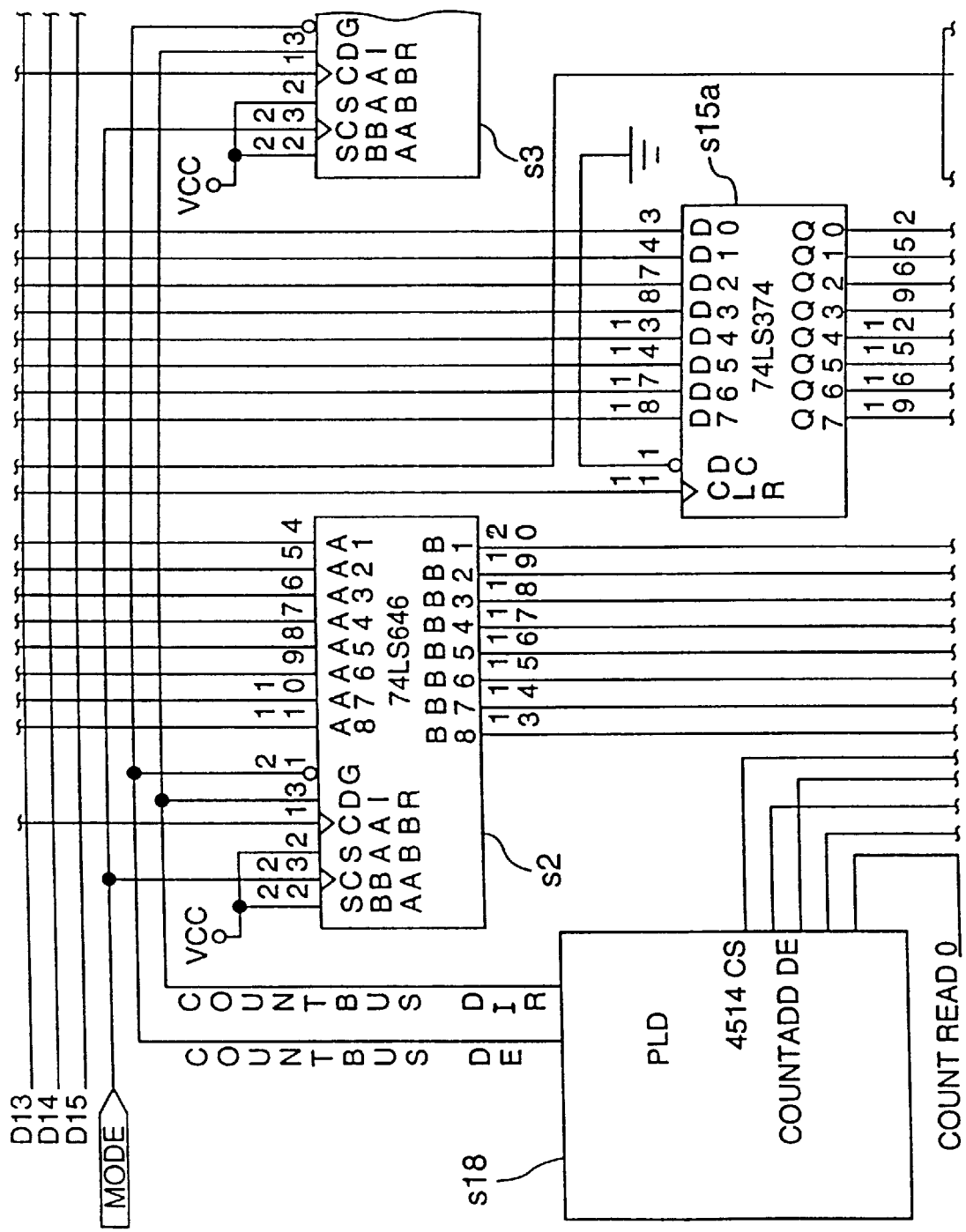
Figure 4F:
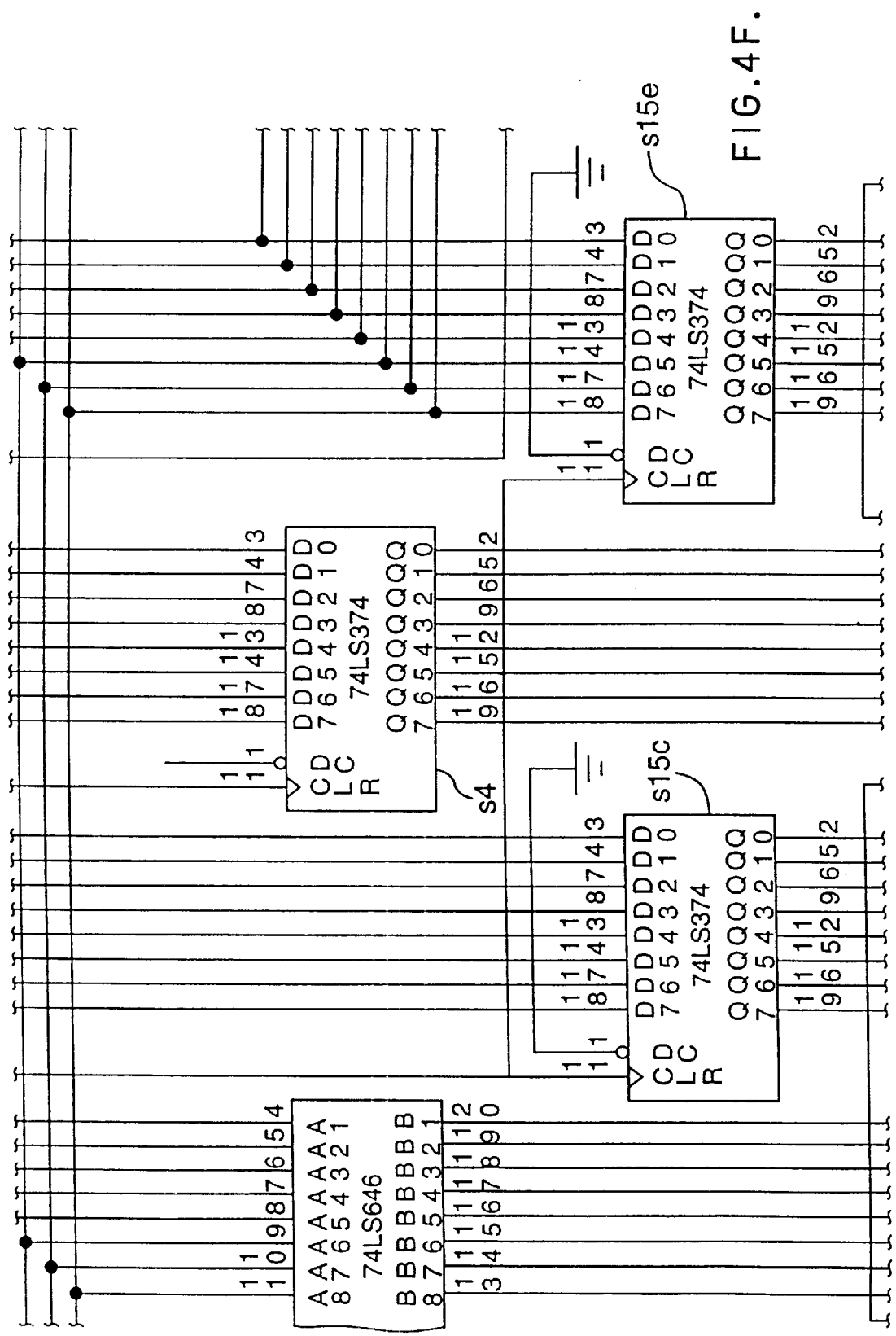
Figure 4G:
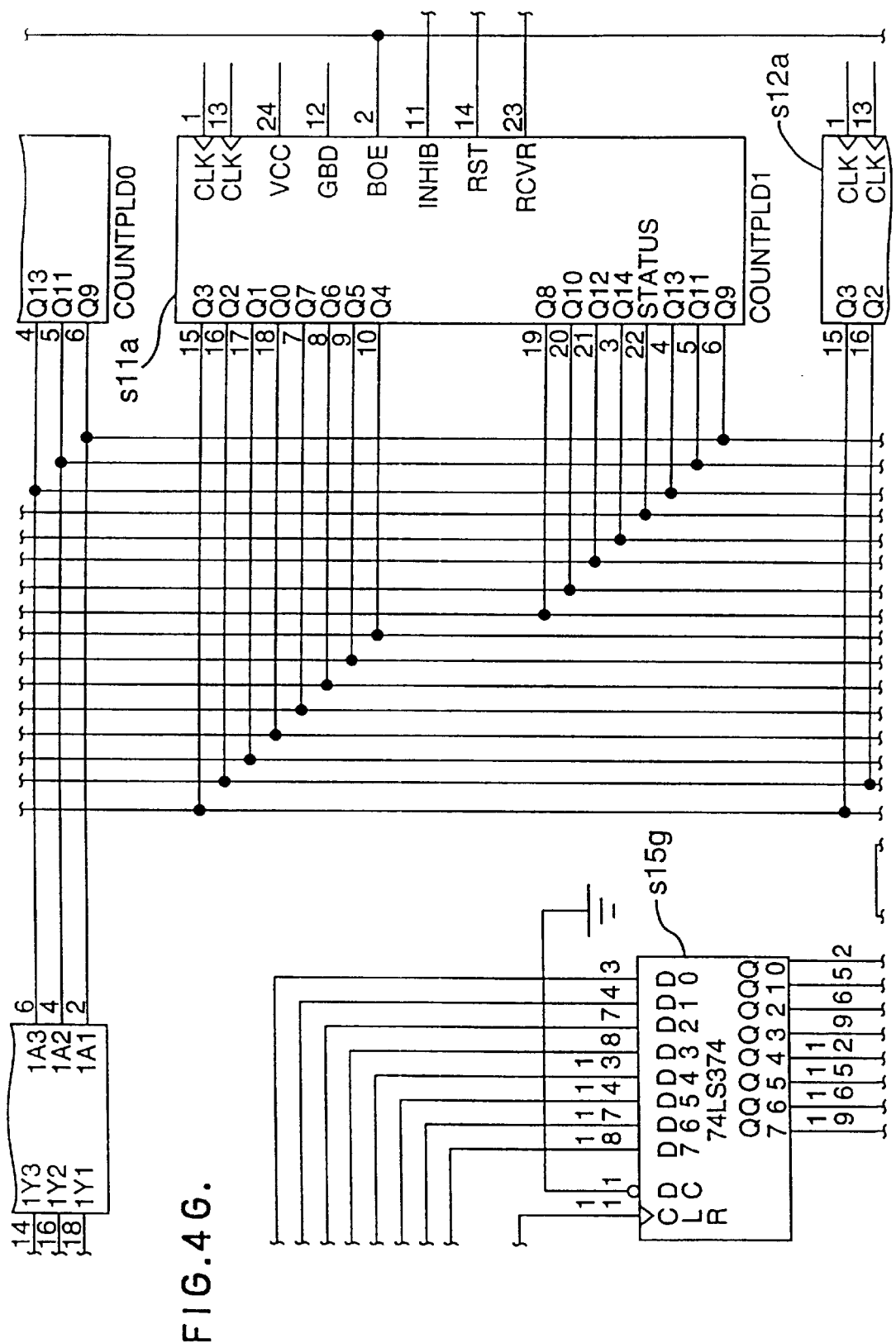
Figure 4H:
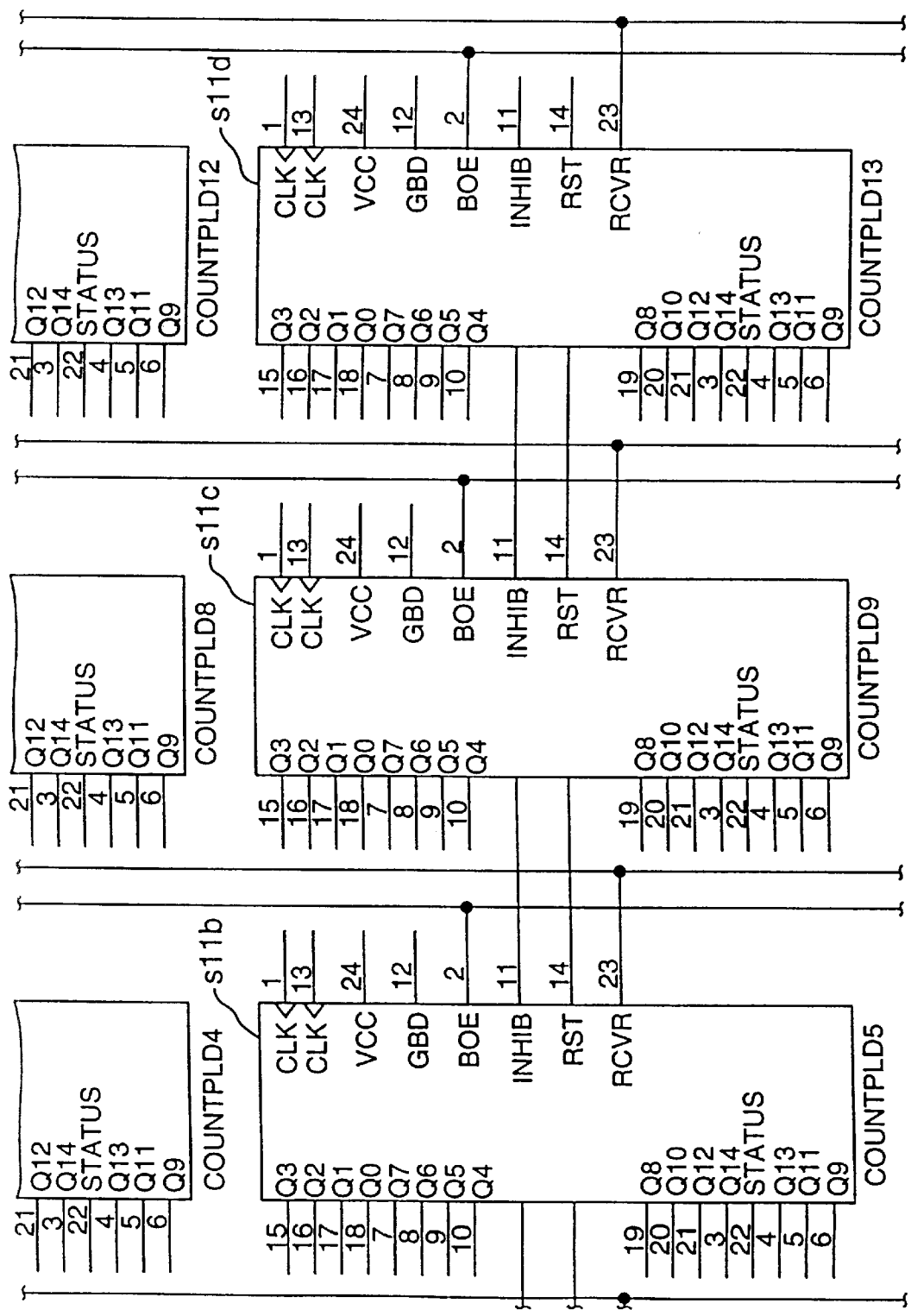
Figure 4I:
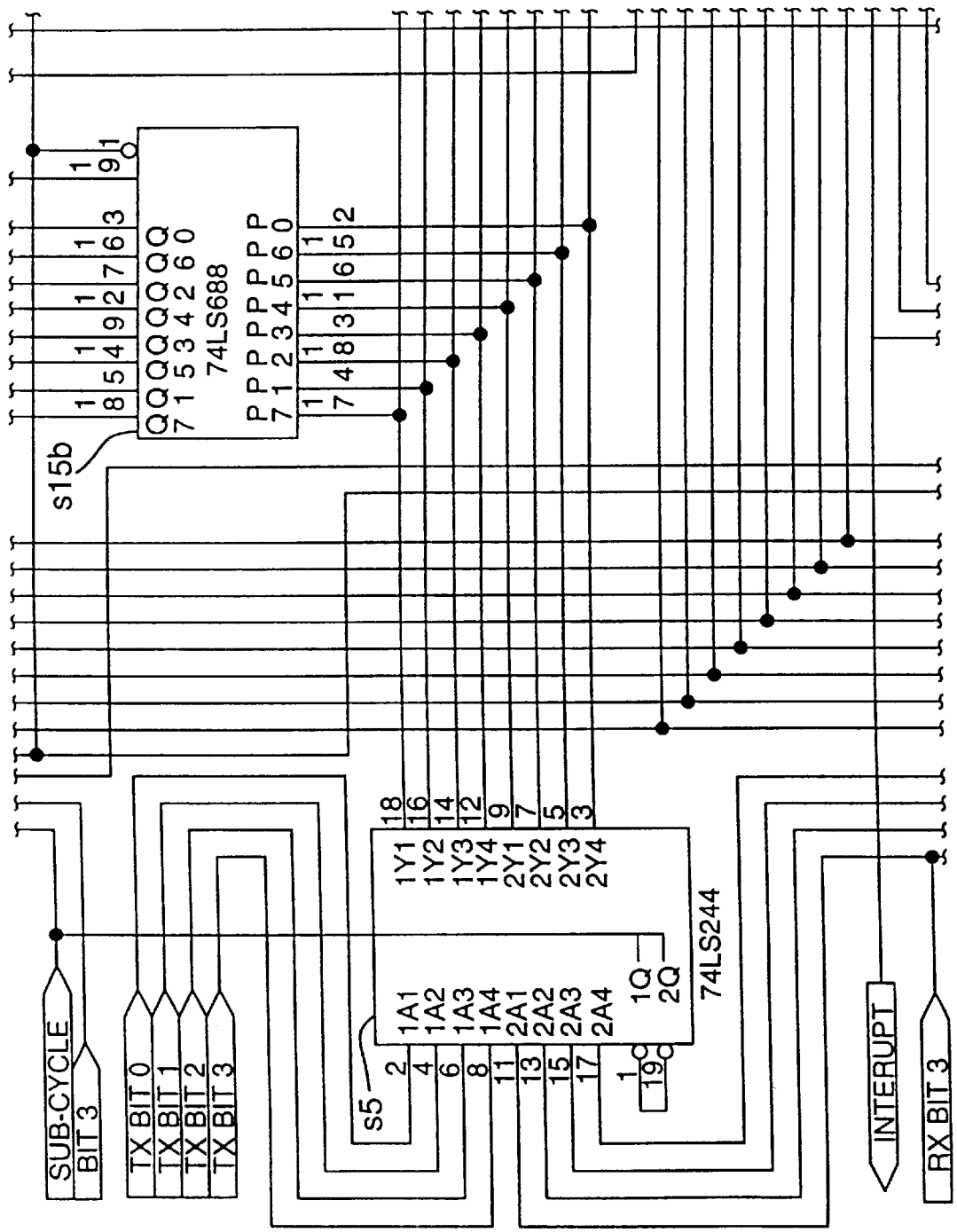
Figure 4J:
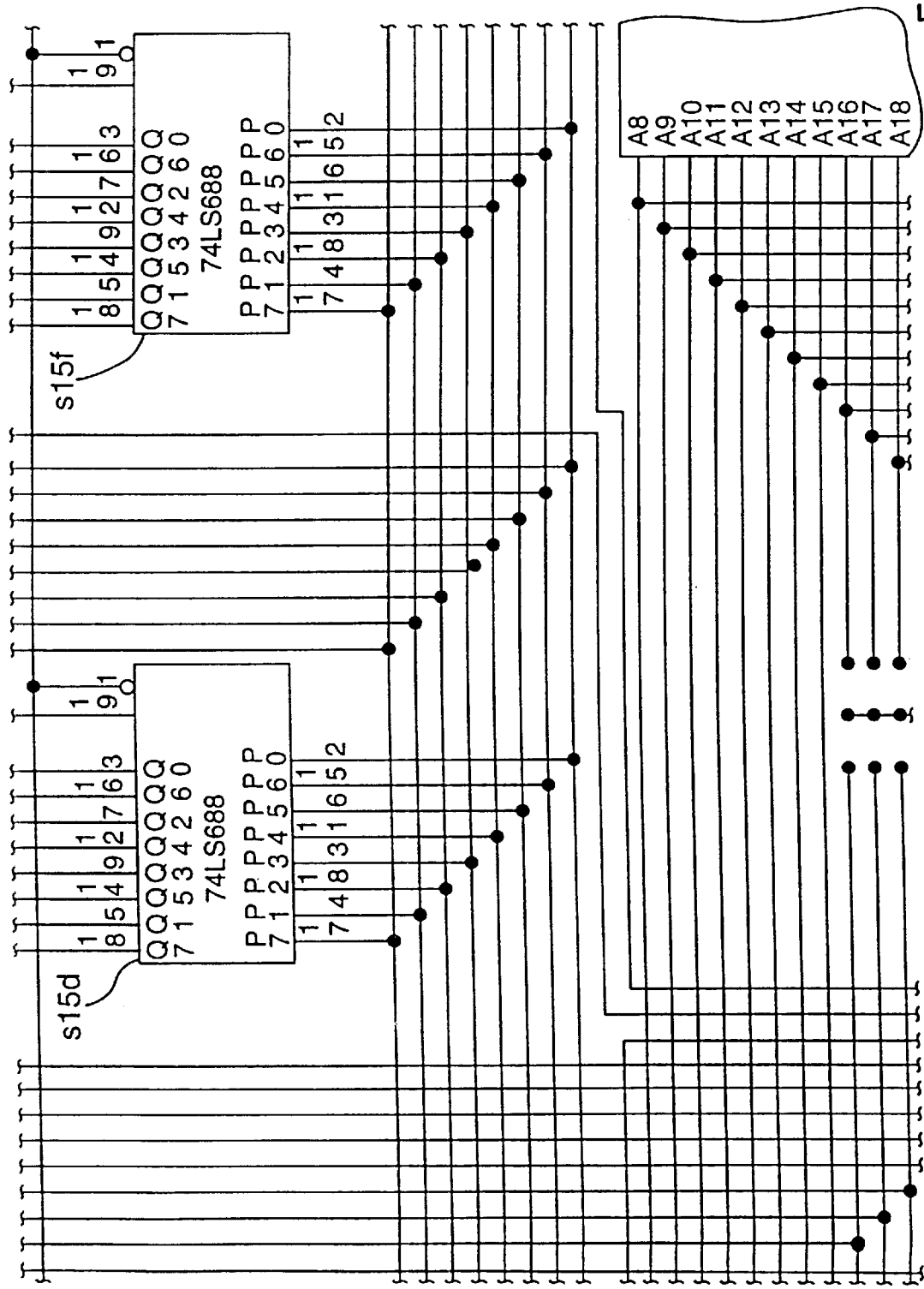
Figure 4K:
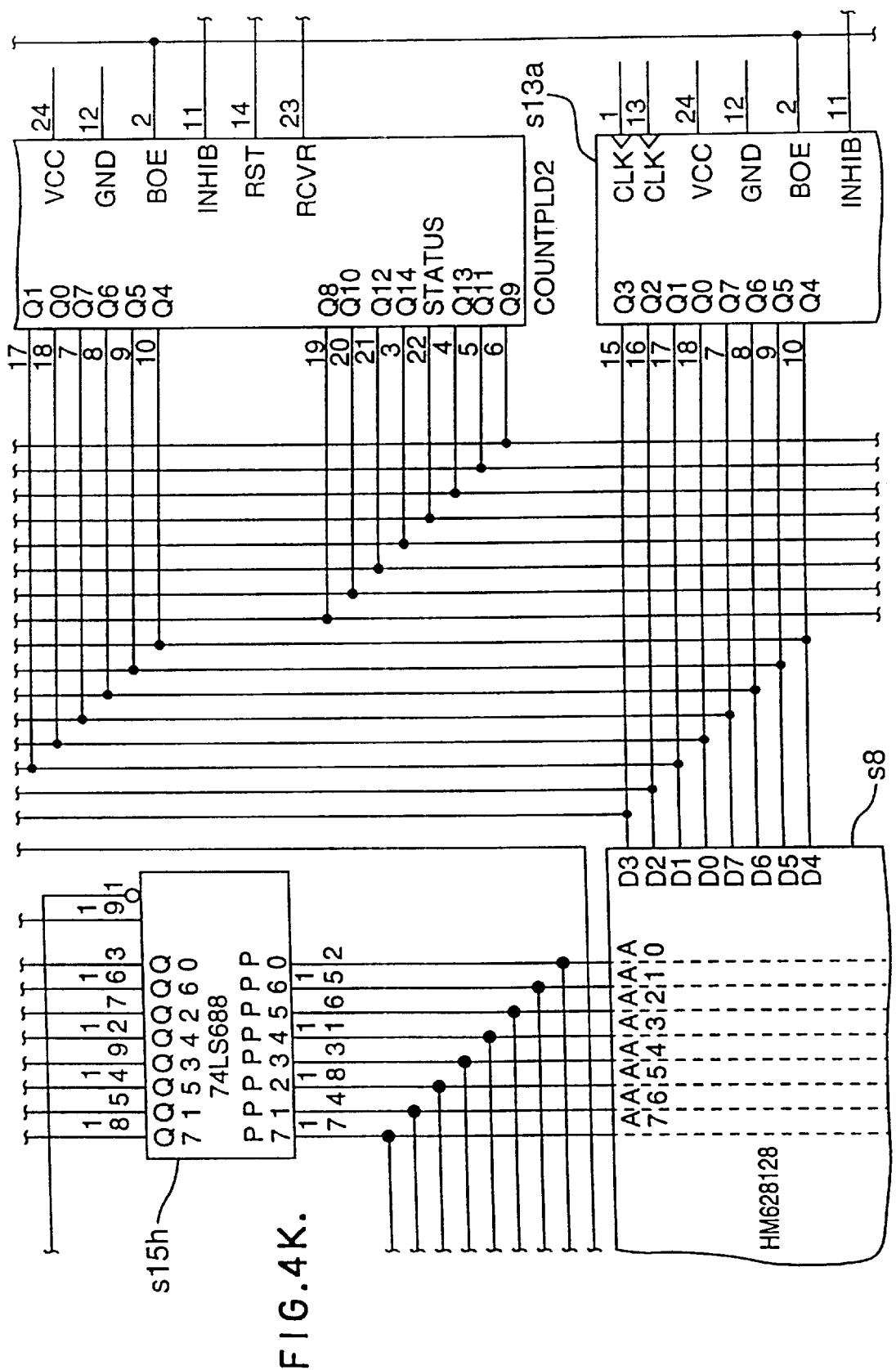
Figure 4L:
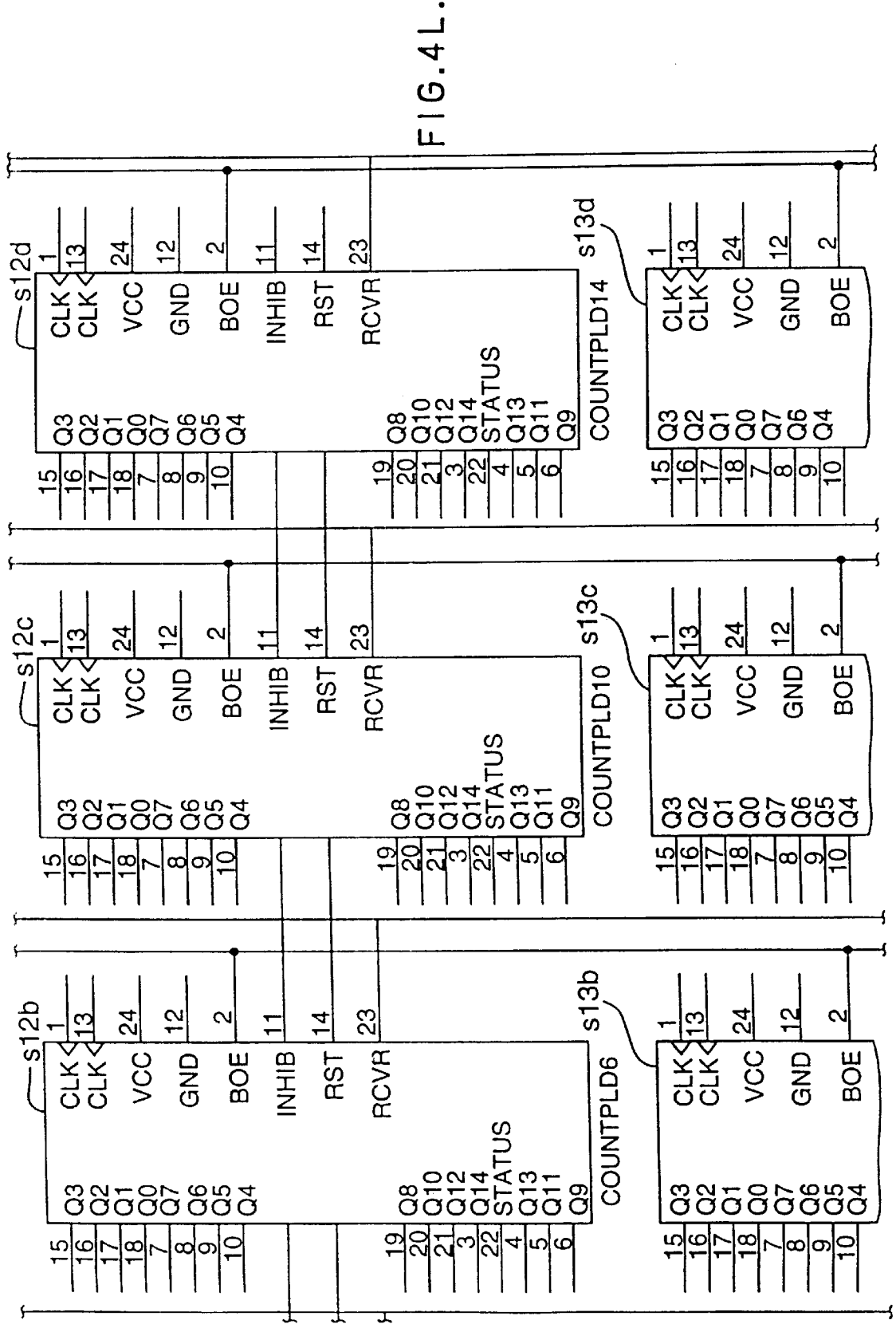
Figure 4M:
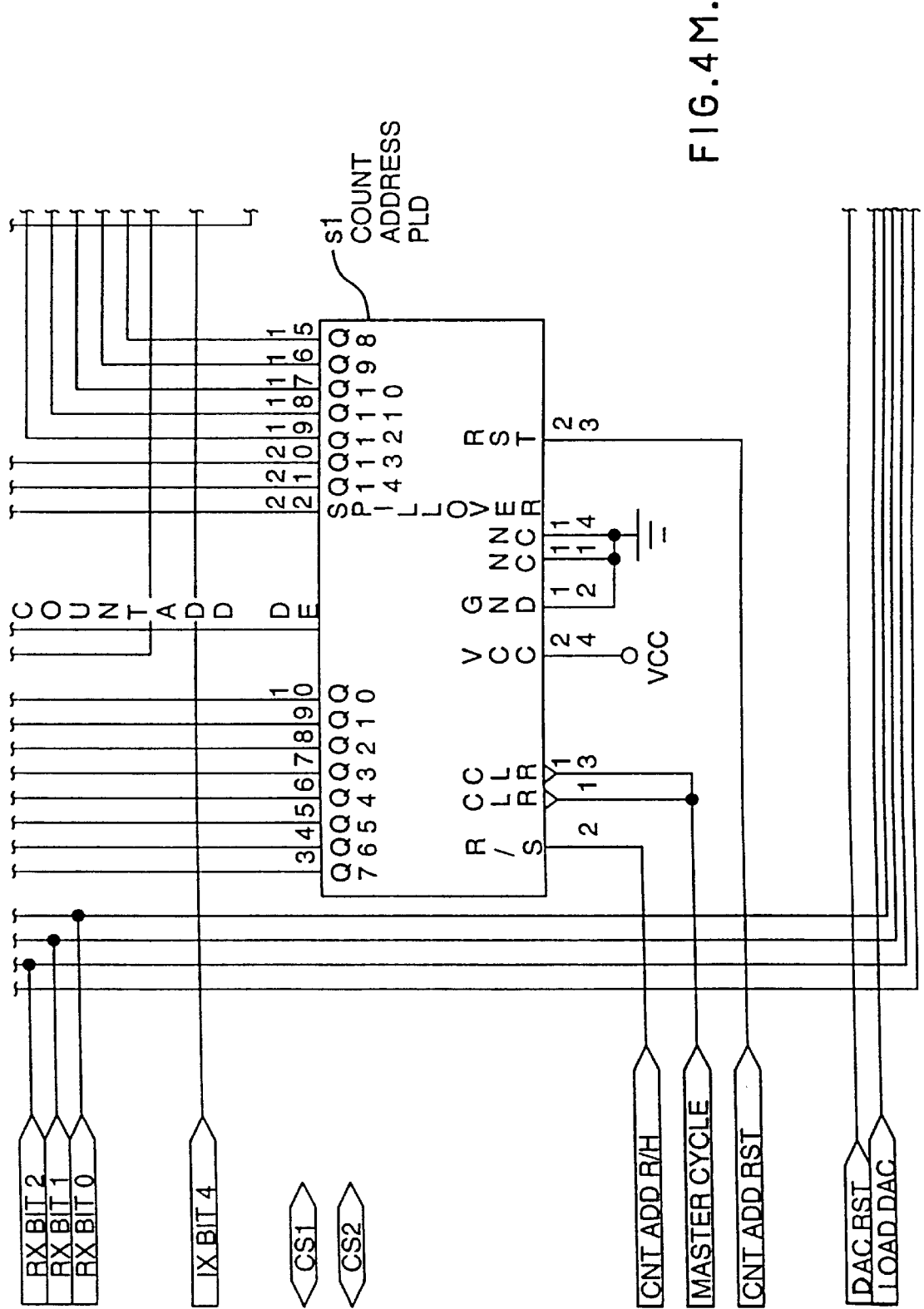
Figure 4N:
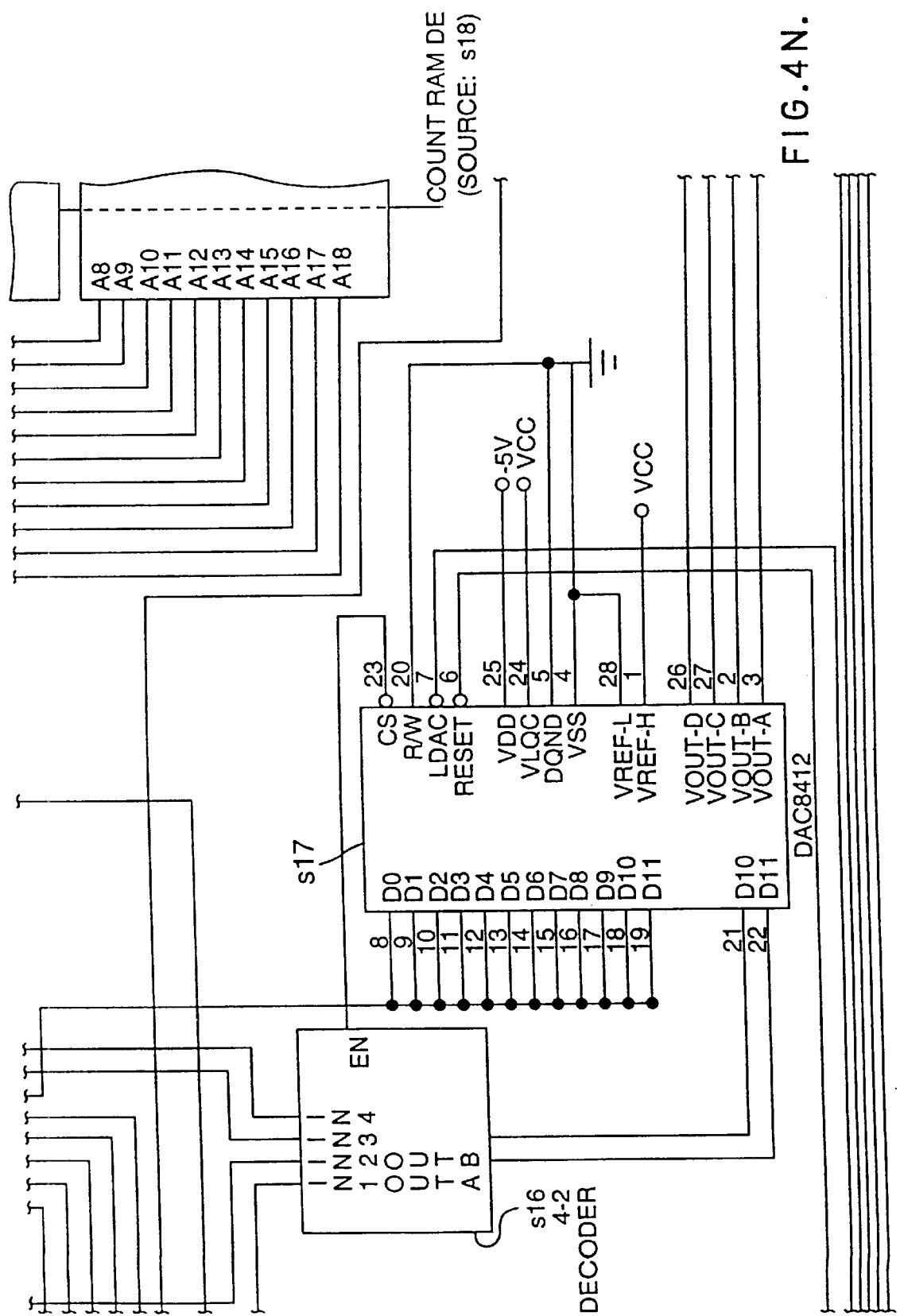
Figure 40:
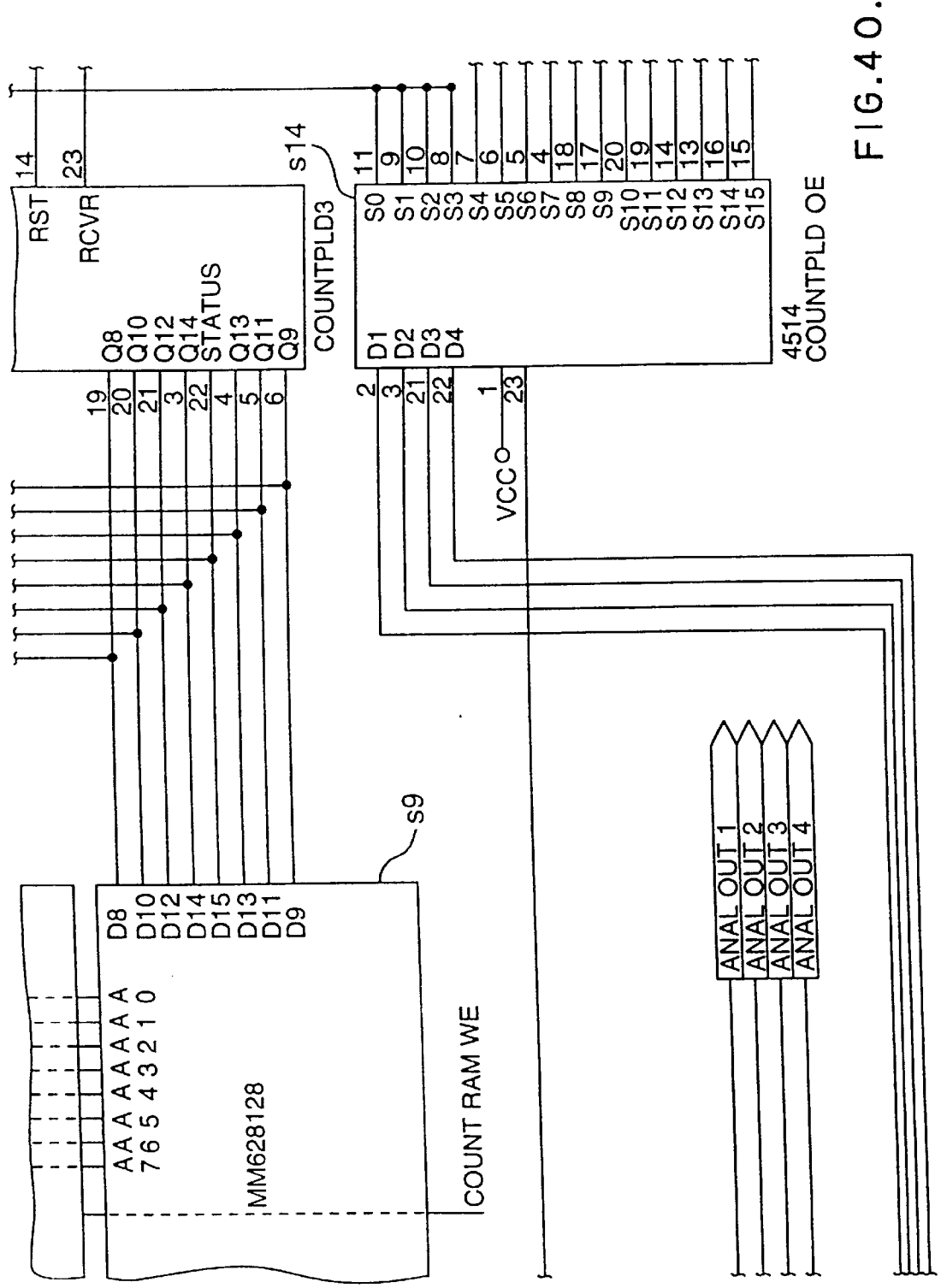
Figure 4P:
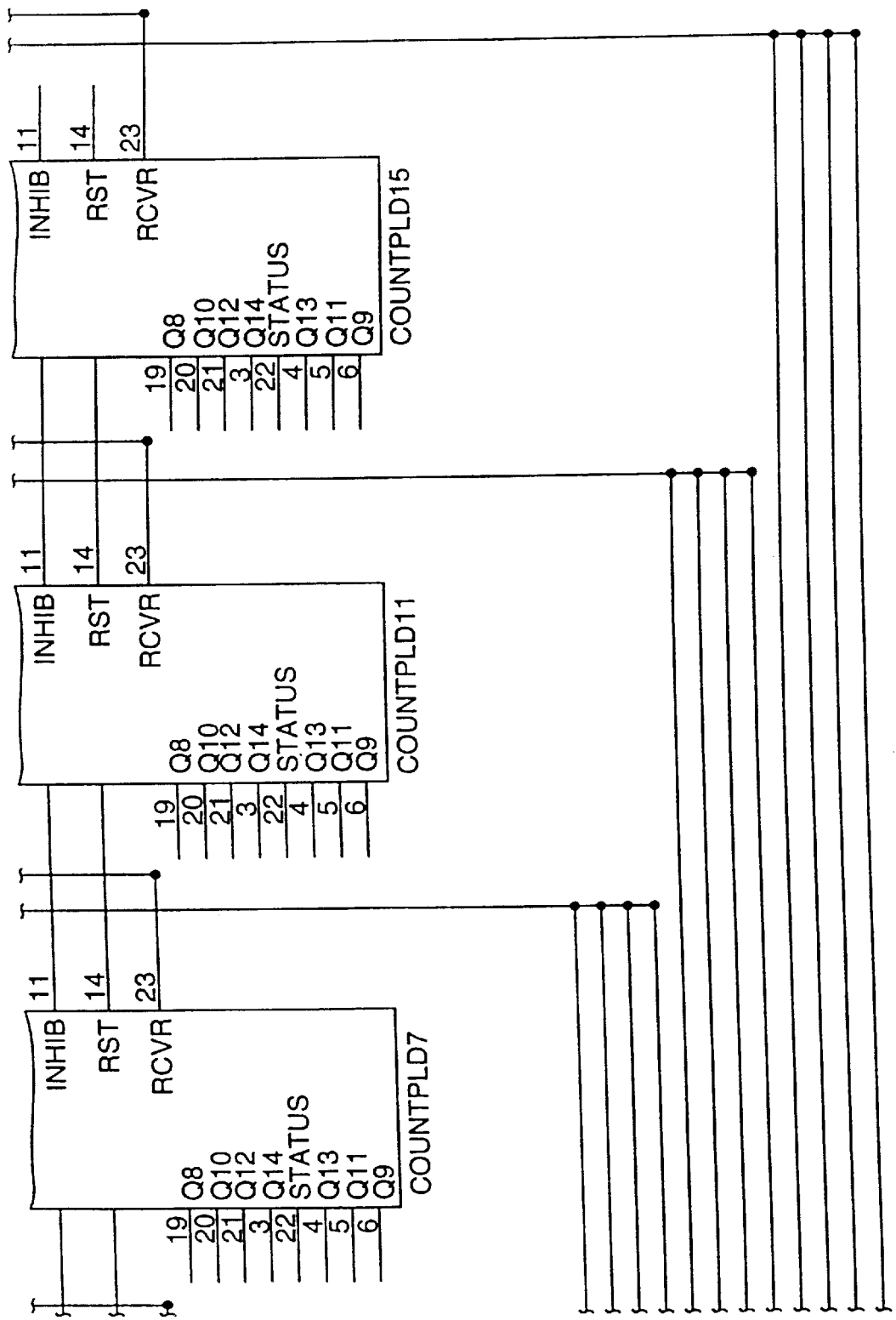
Figure 5B:
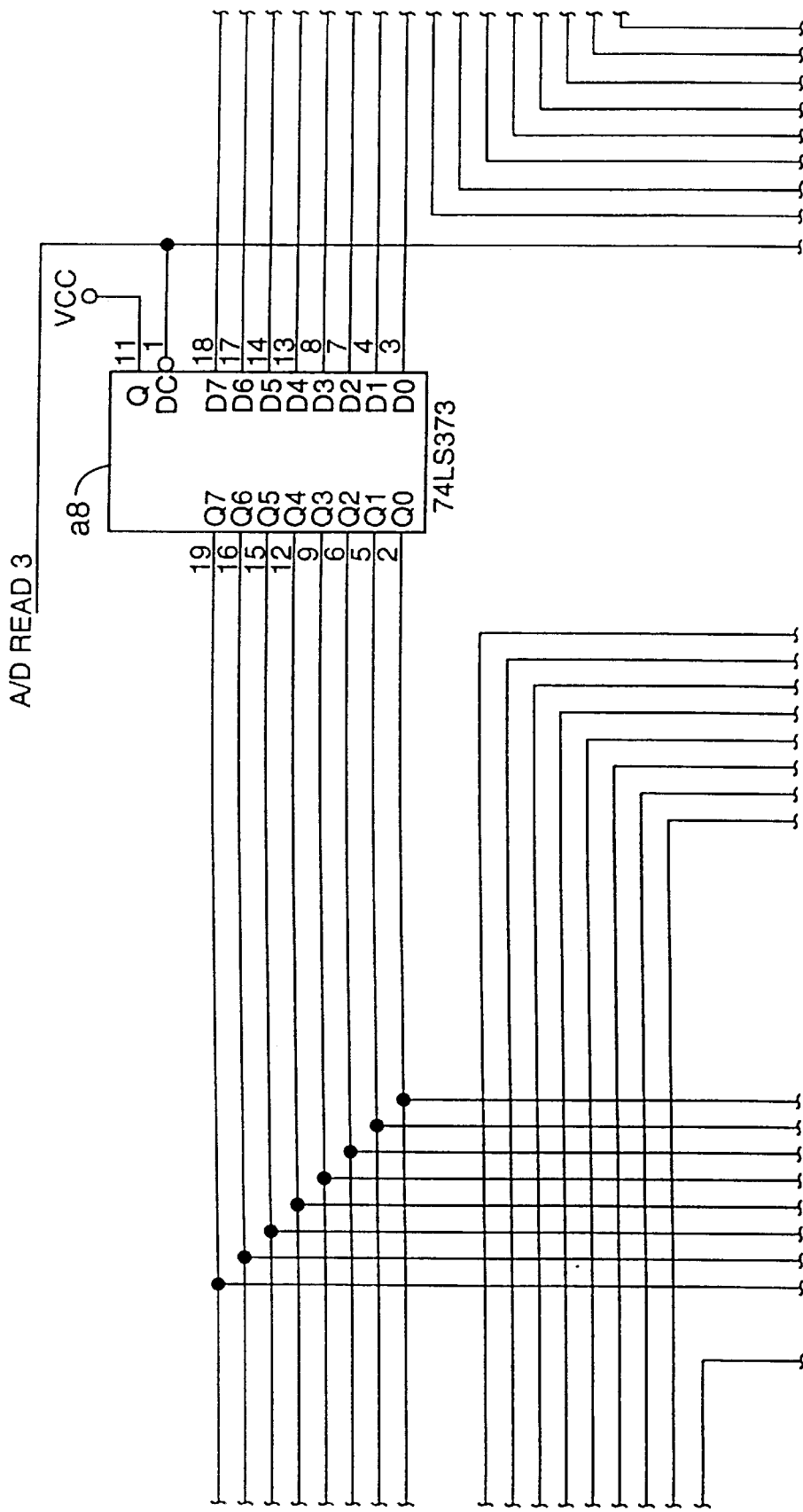
Figure 5C:
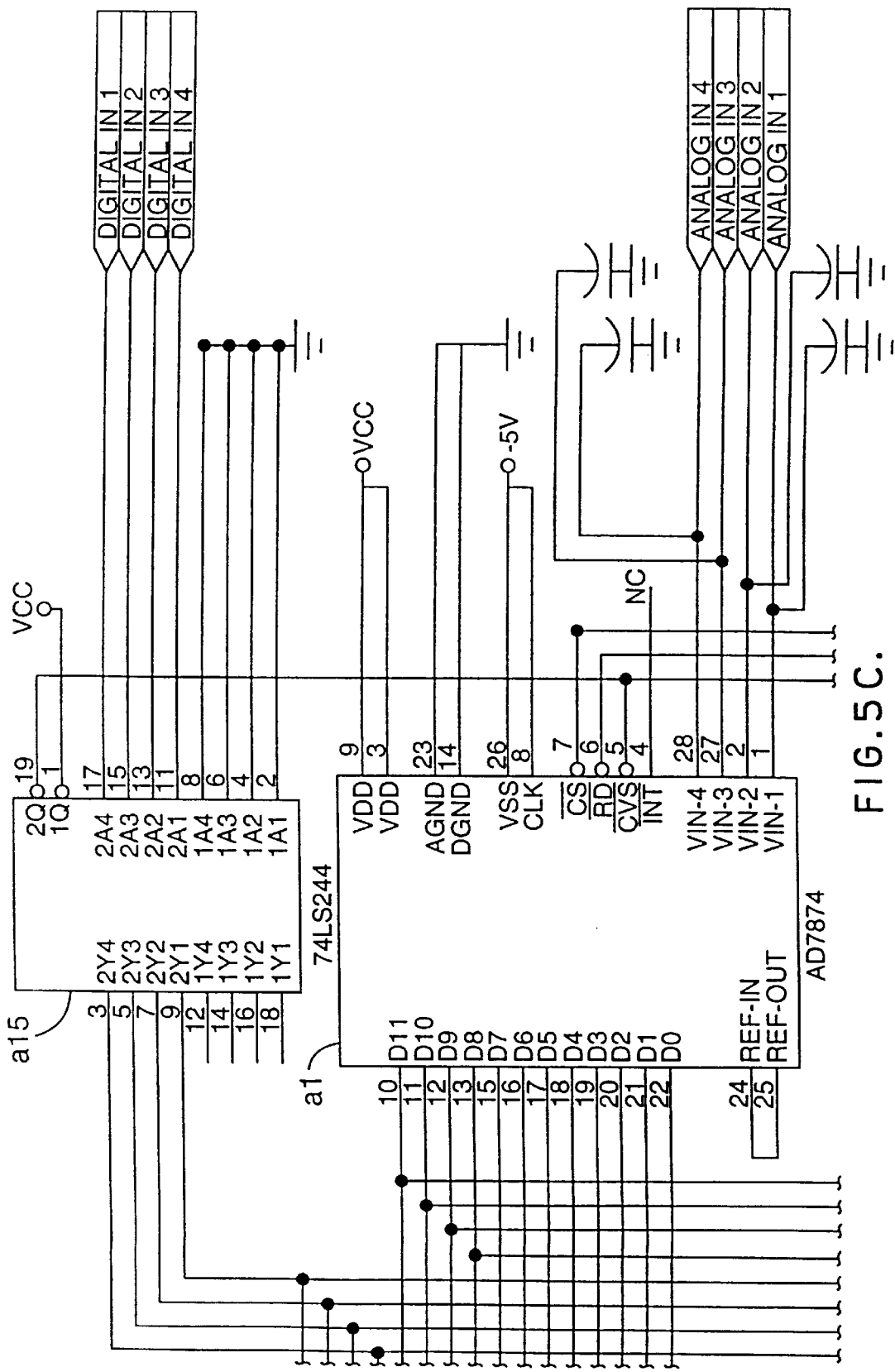
Figure 5D:
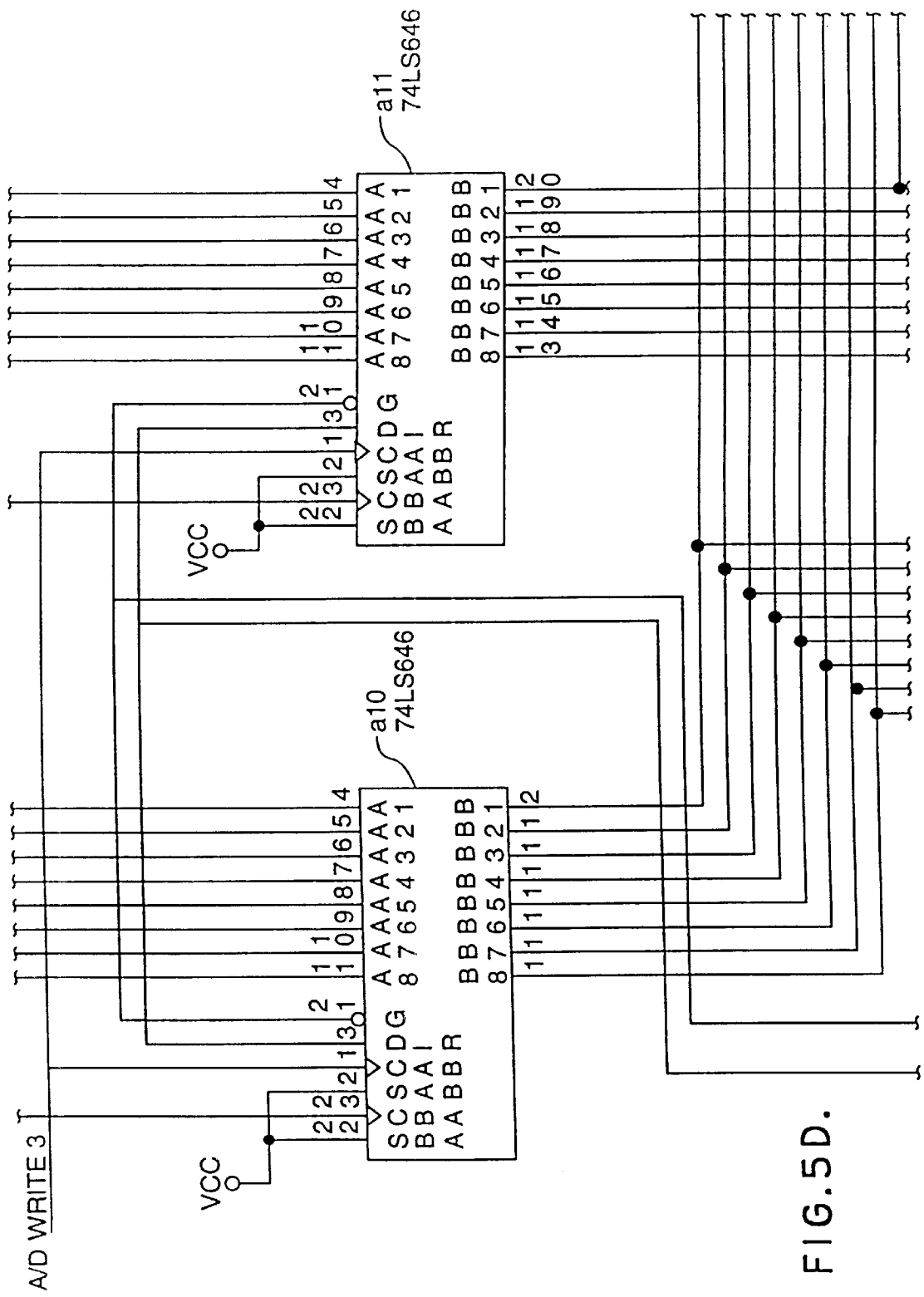
Figure 5E:
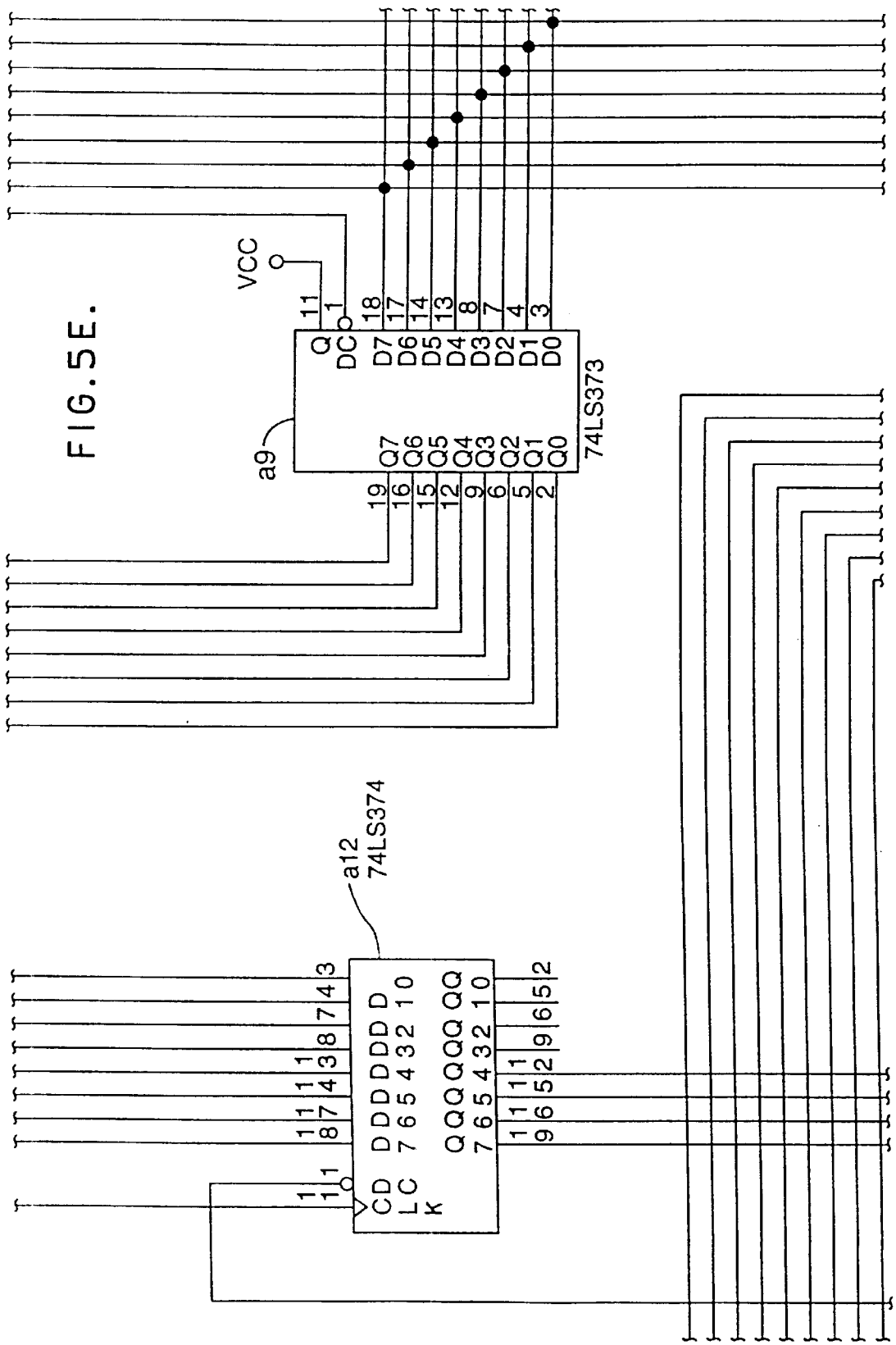
Figure 5F:
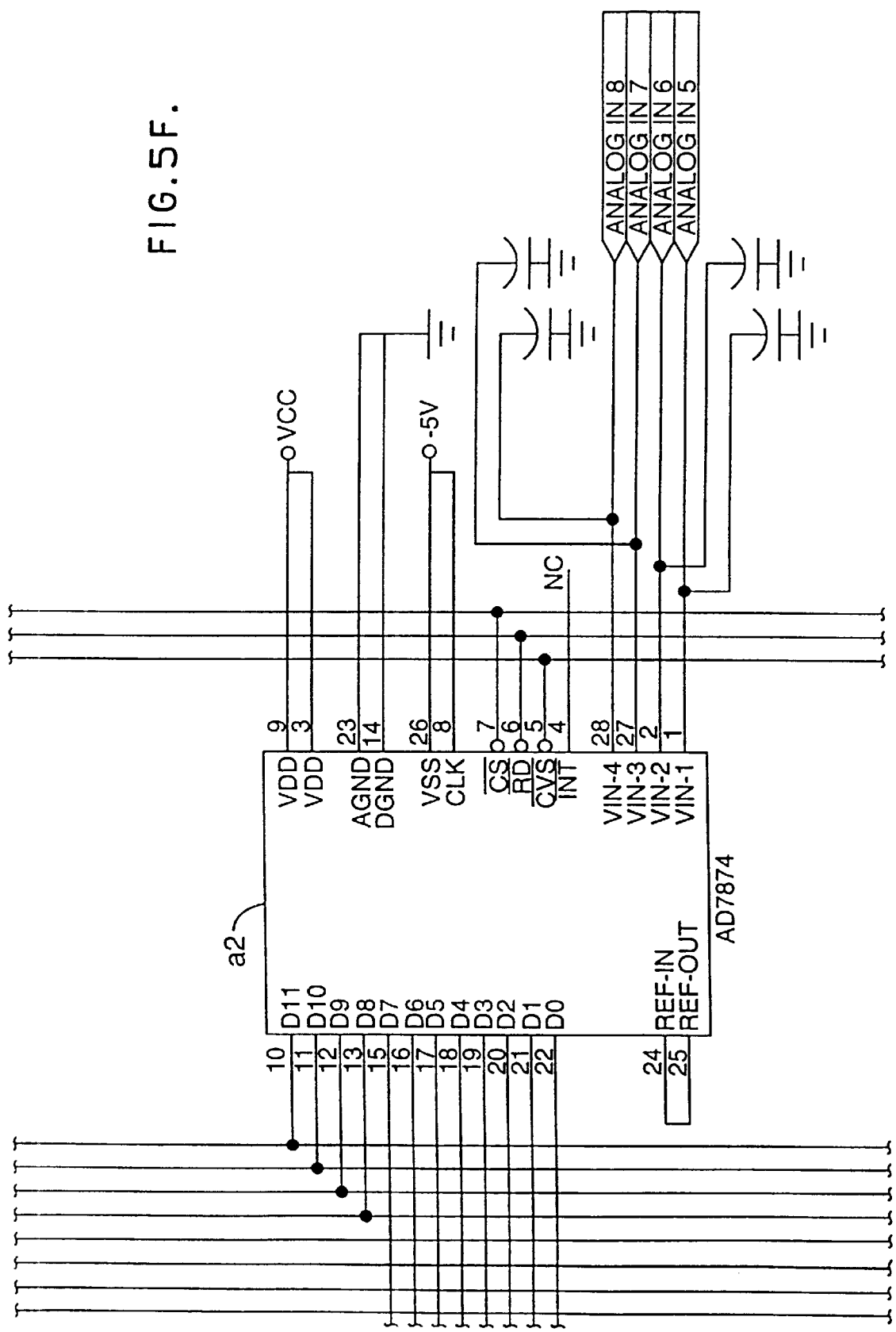
Figure 5G:
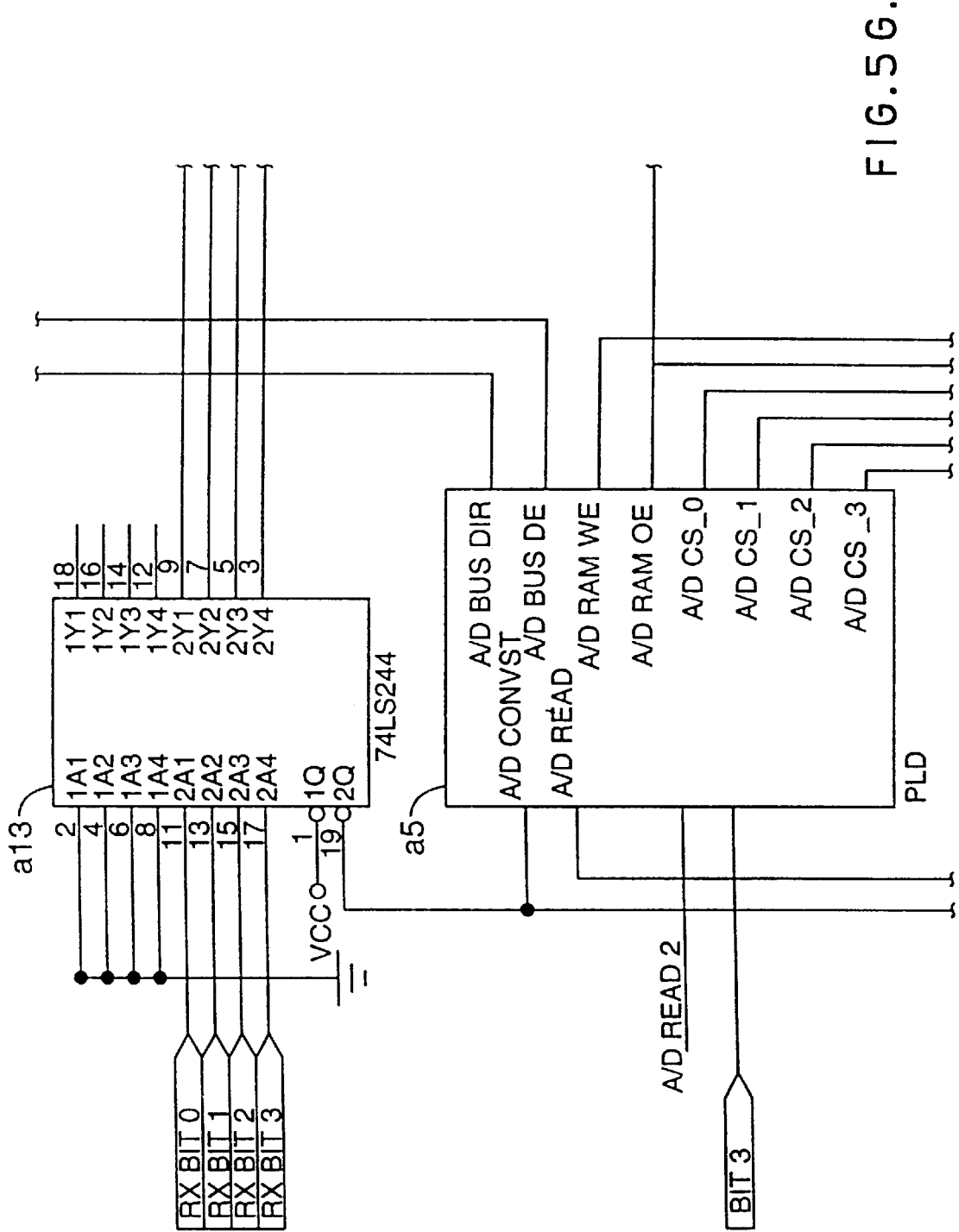
Figure 5H:
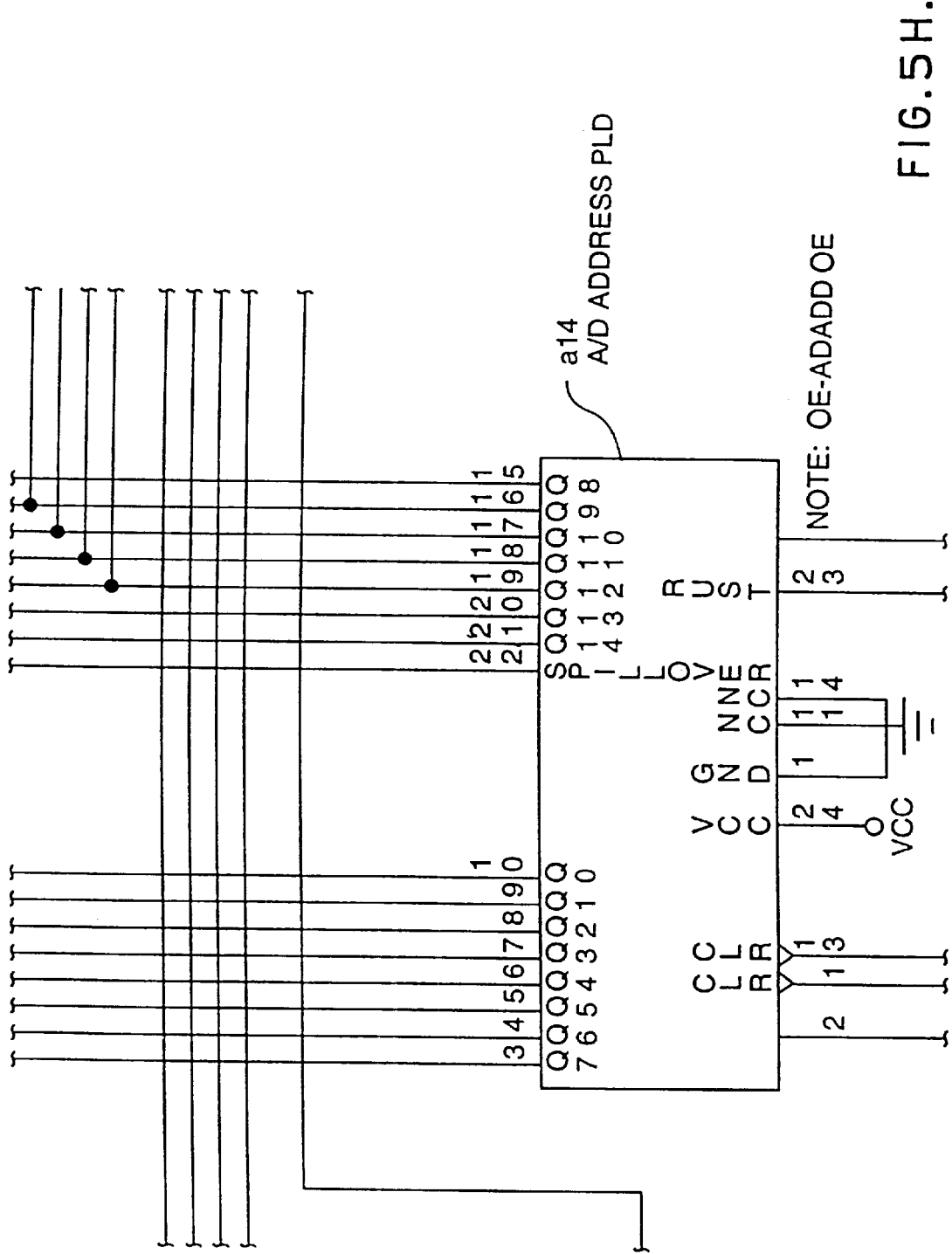
Figure 5I:
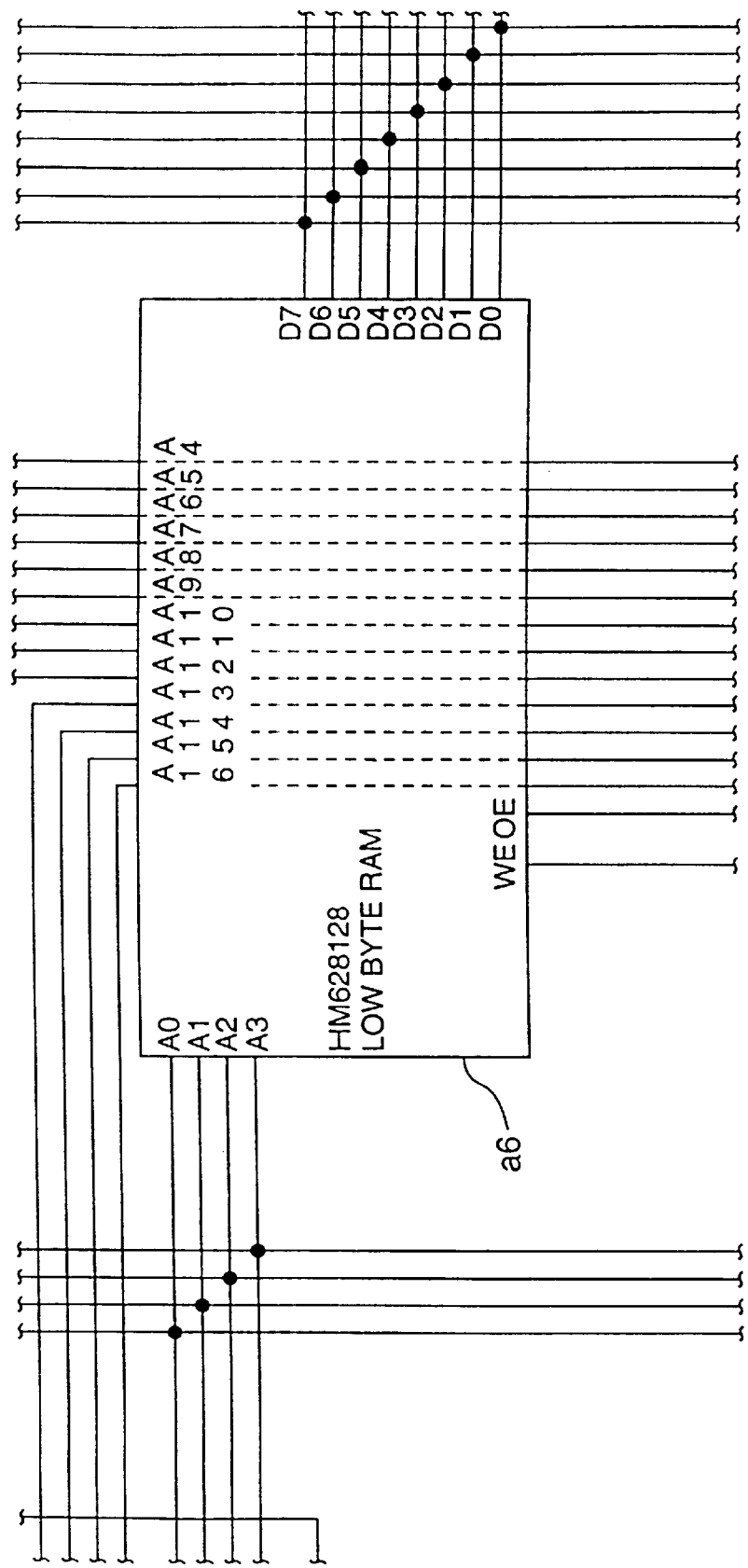
Figure 5J:
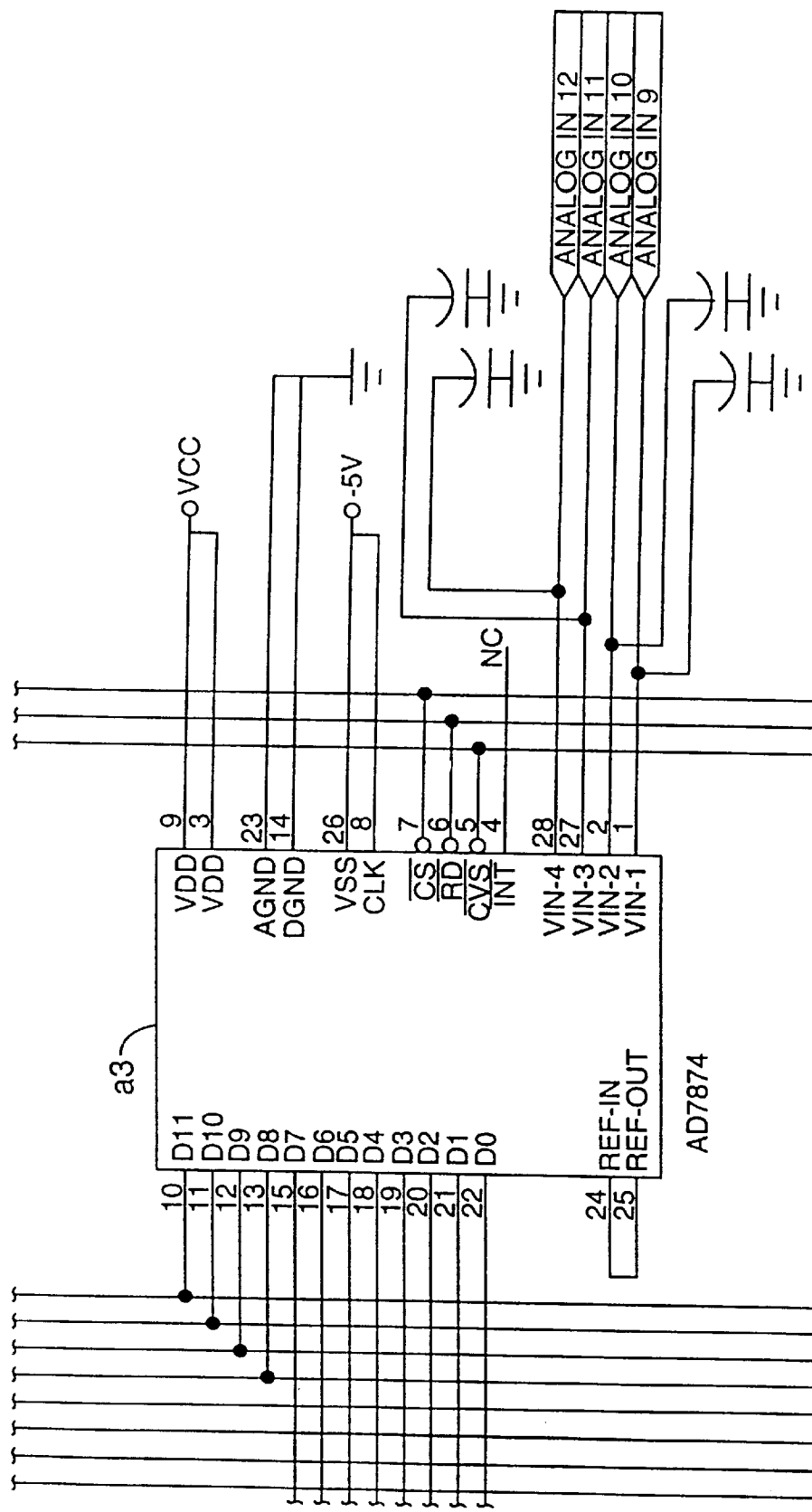
Figure 5K:
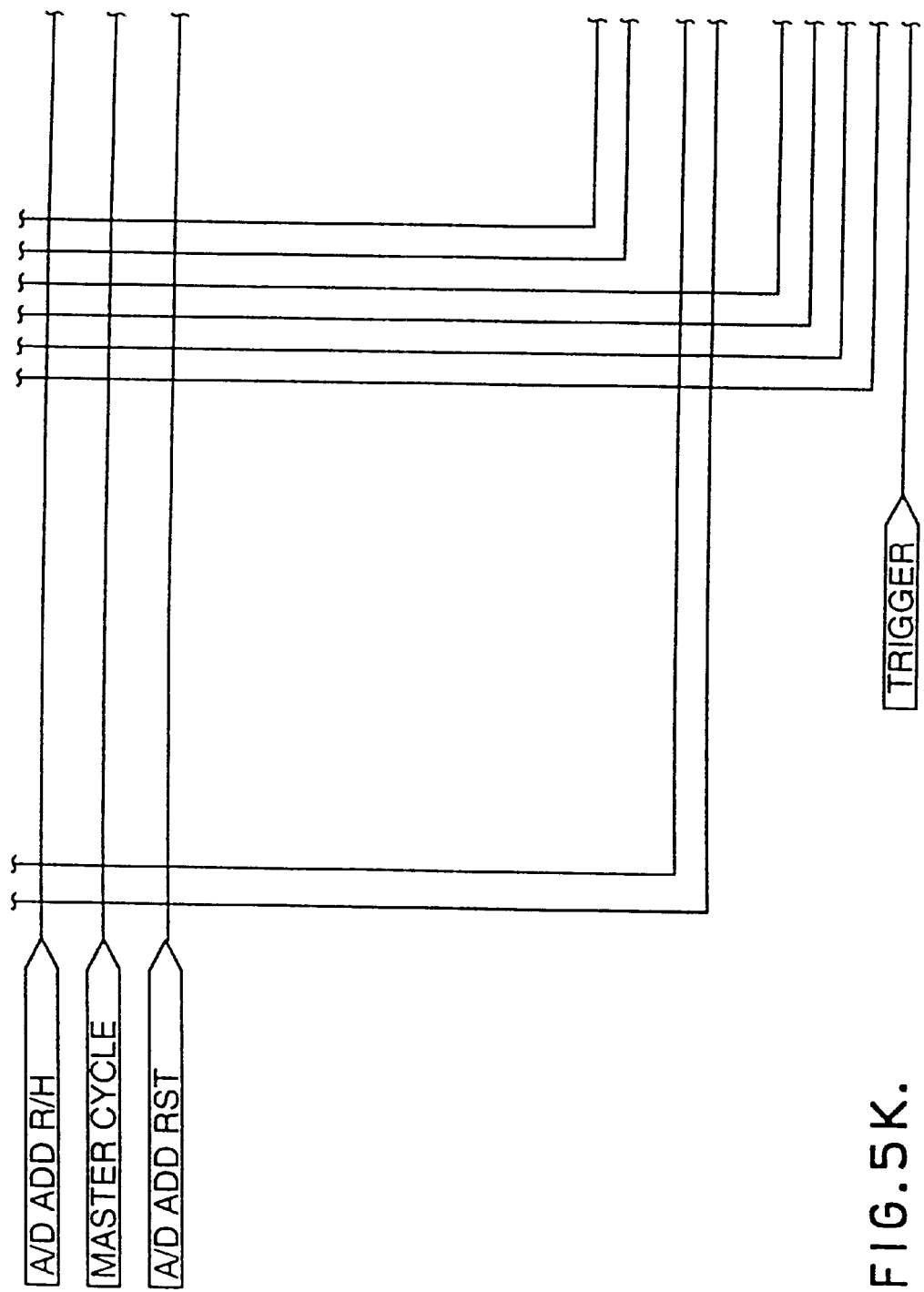
Figure 5L:
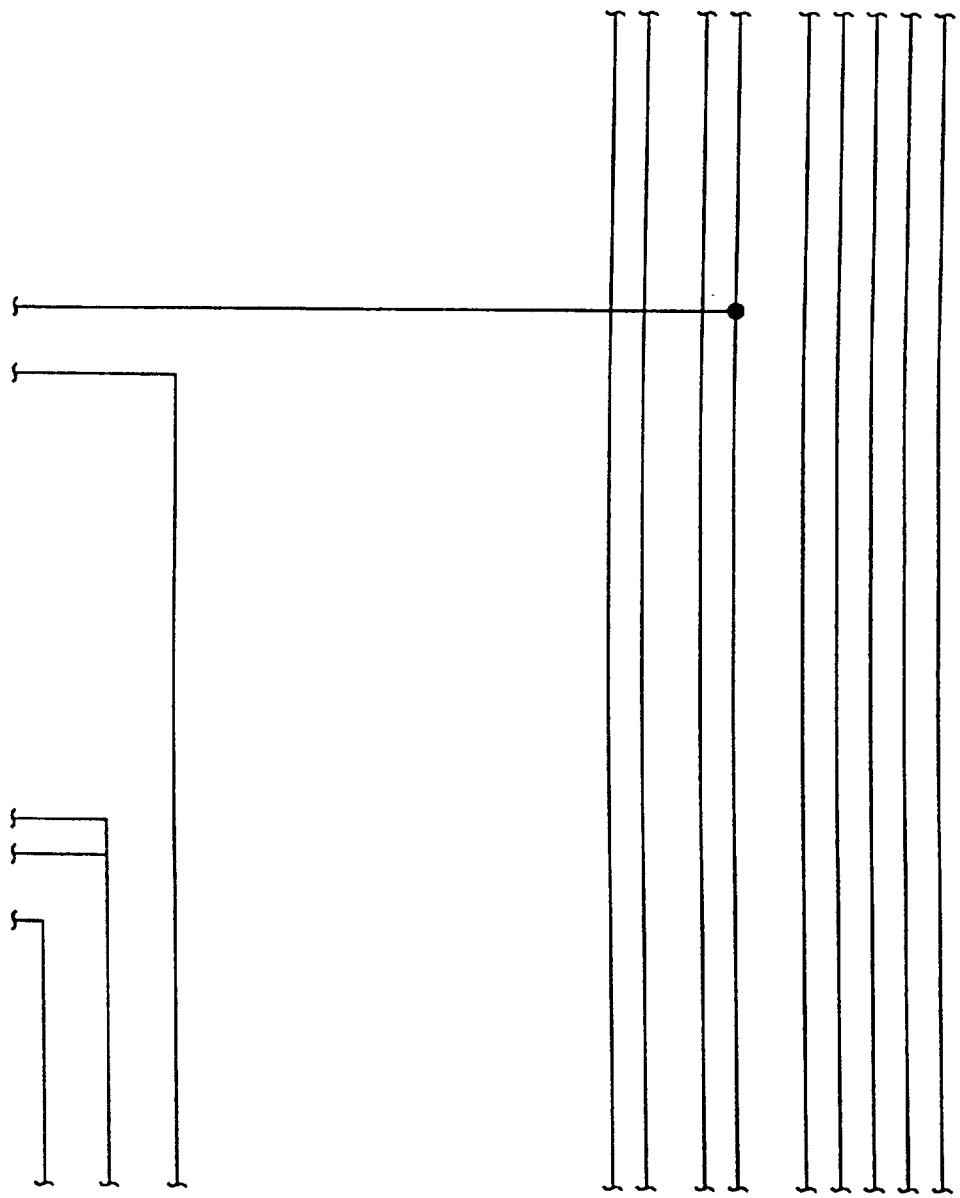
Figure 5M:
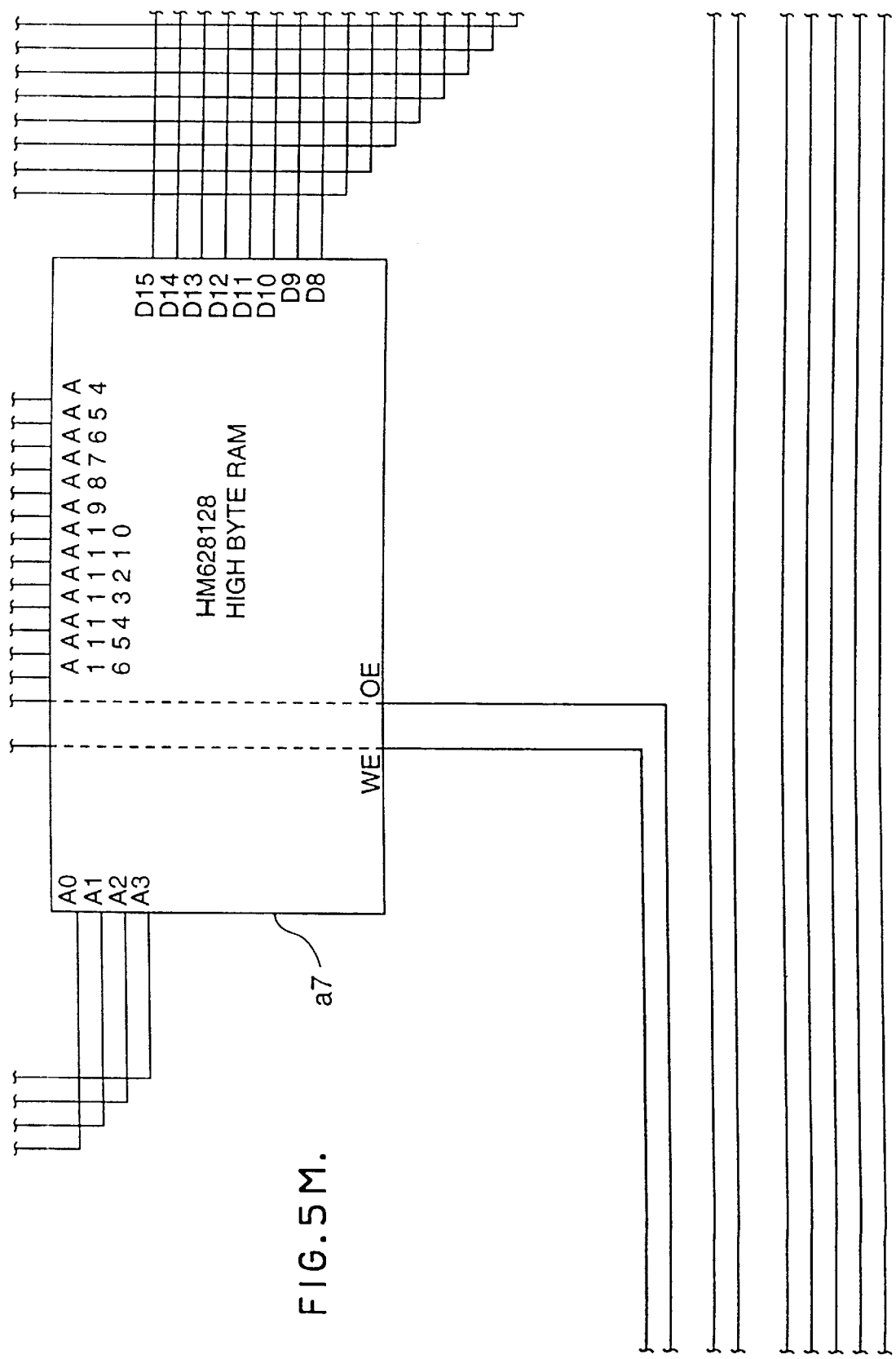
Figure 5N:
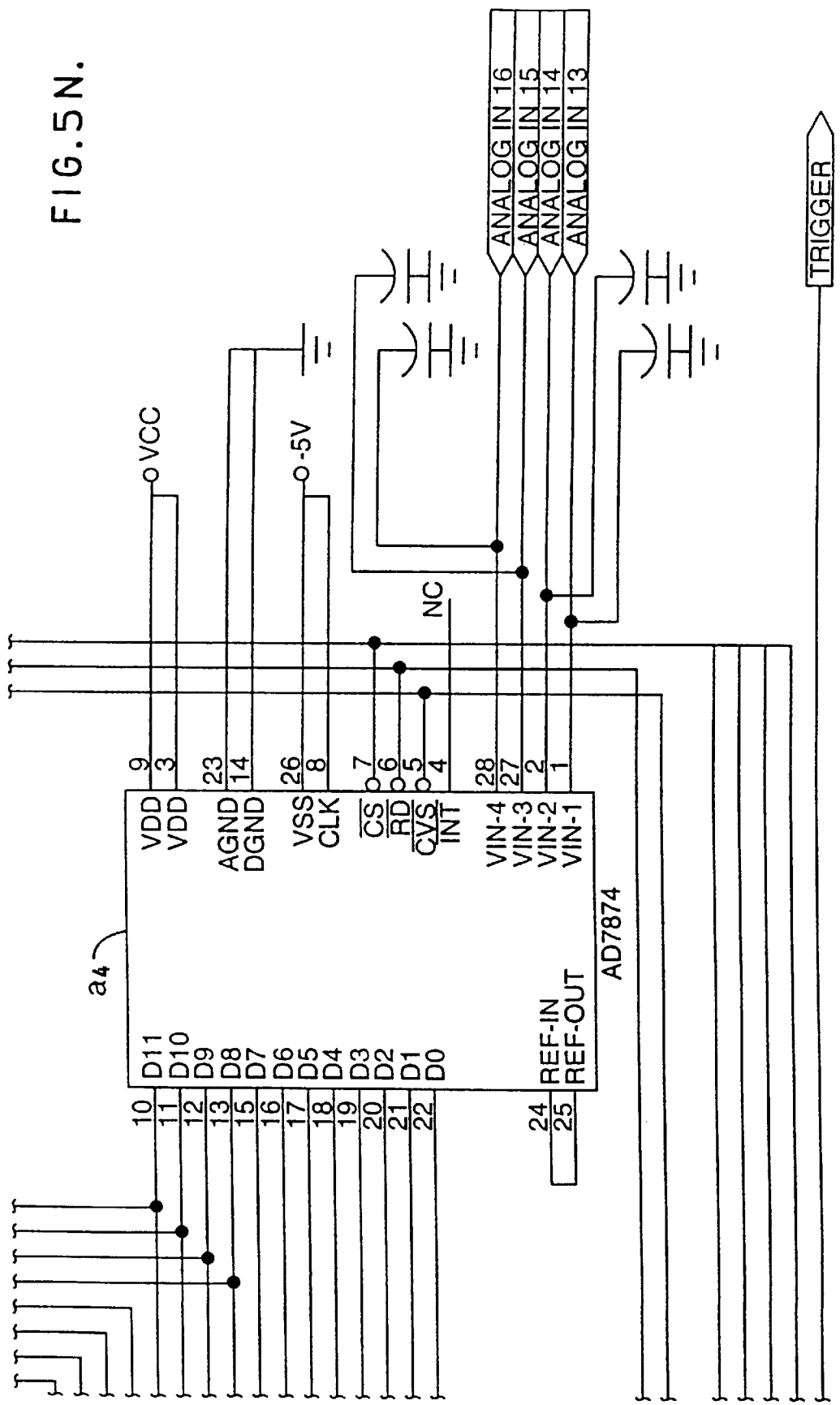
Figure 6A:
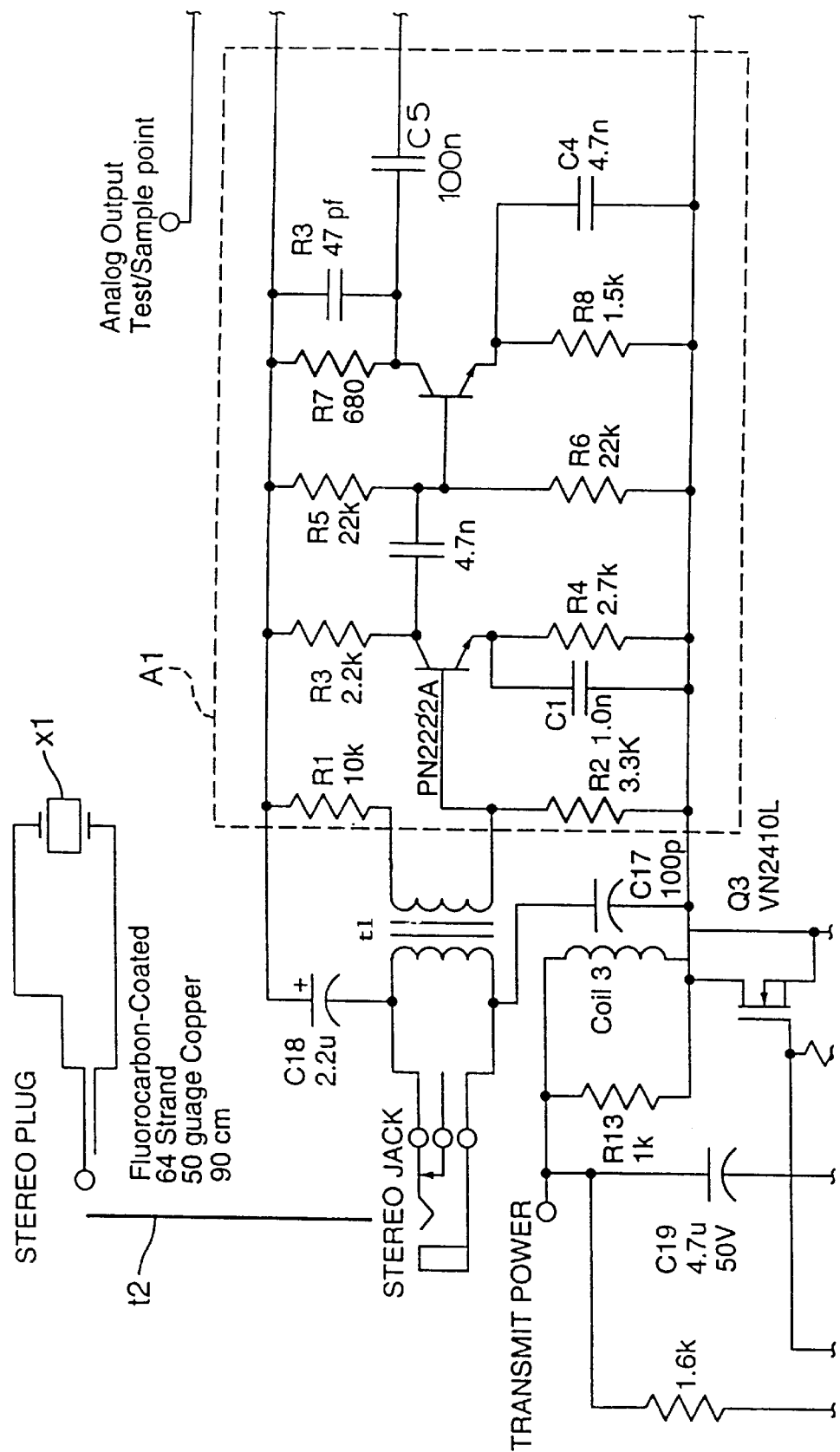
FIGS. 6A, 6B, 6C and 6D, is a schematic diagram of a transmitter/receiver/transceiver architecture according to the preferred embodiment.
Figure 6B:
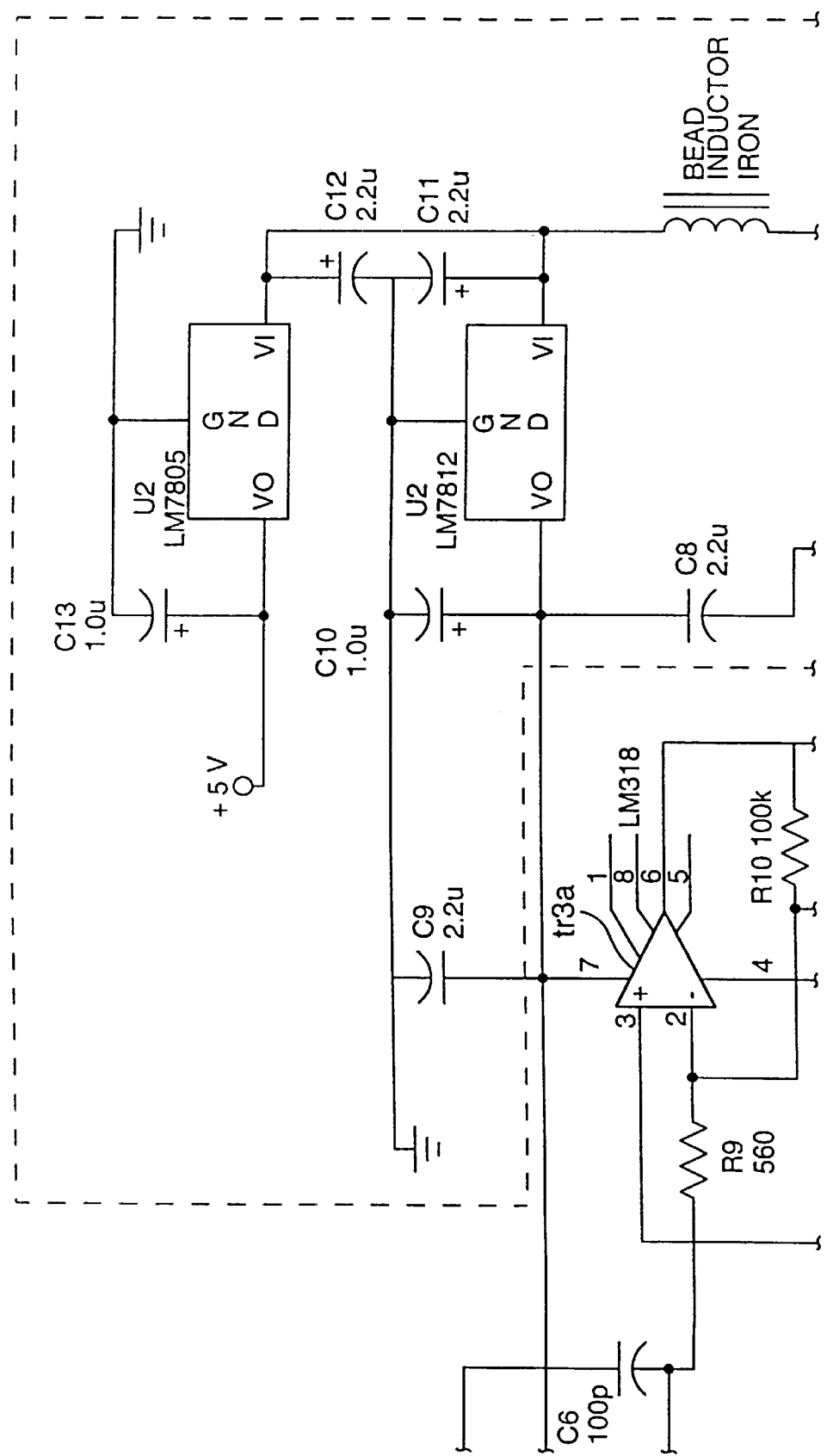
Figure 6C:
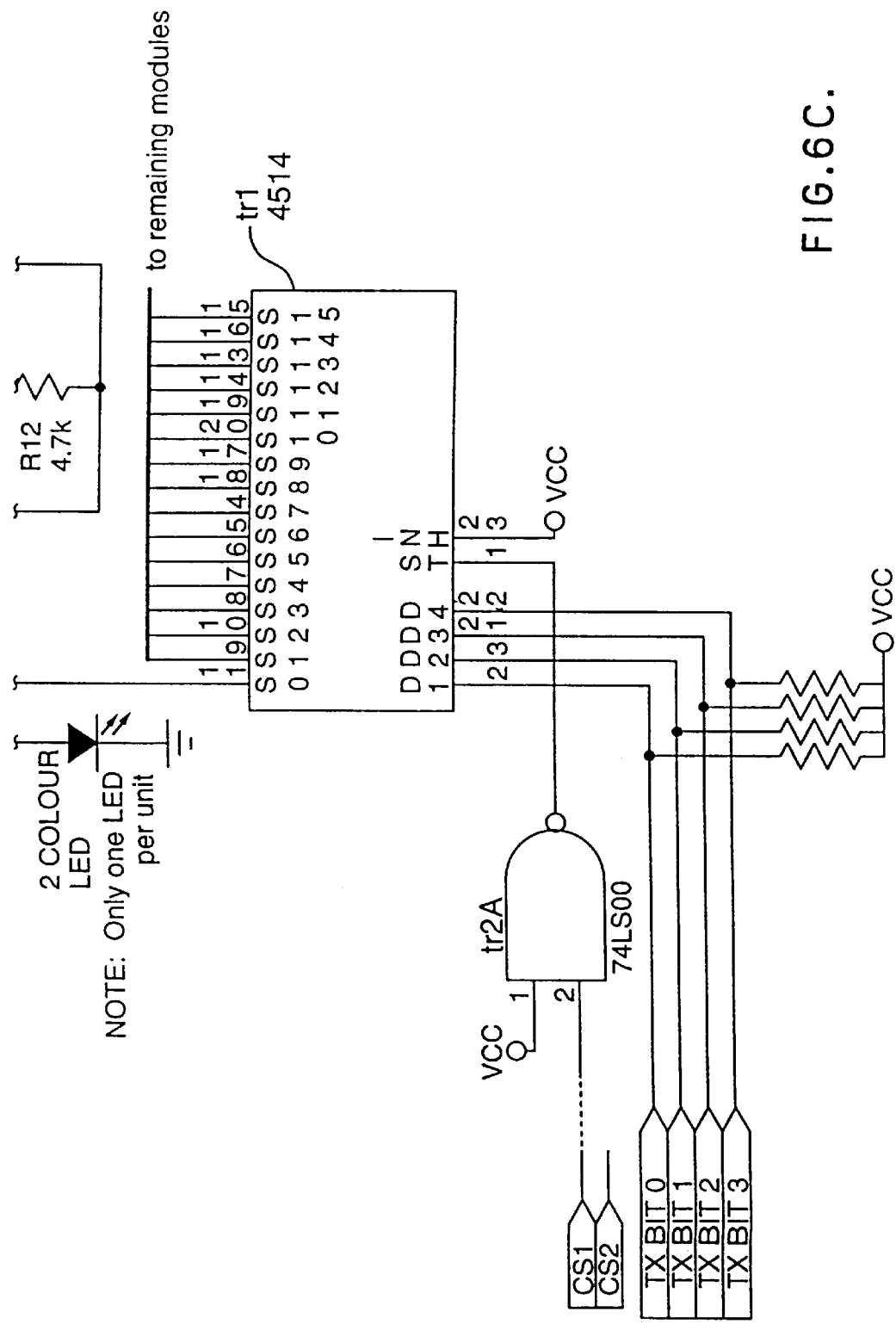
Figure 6D:
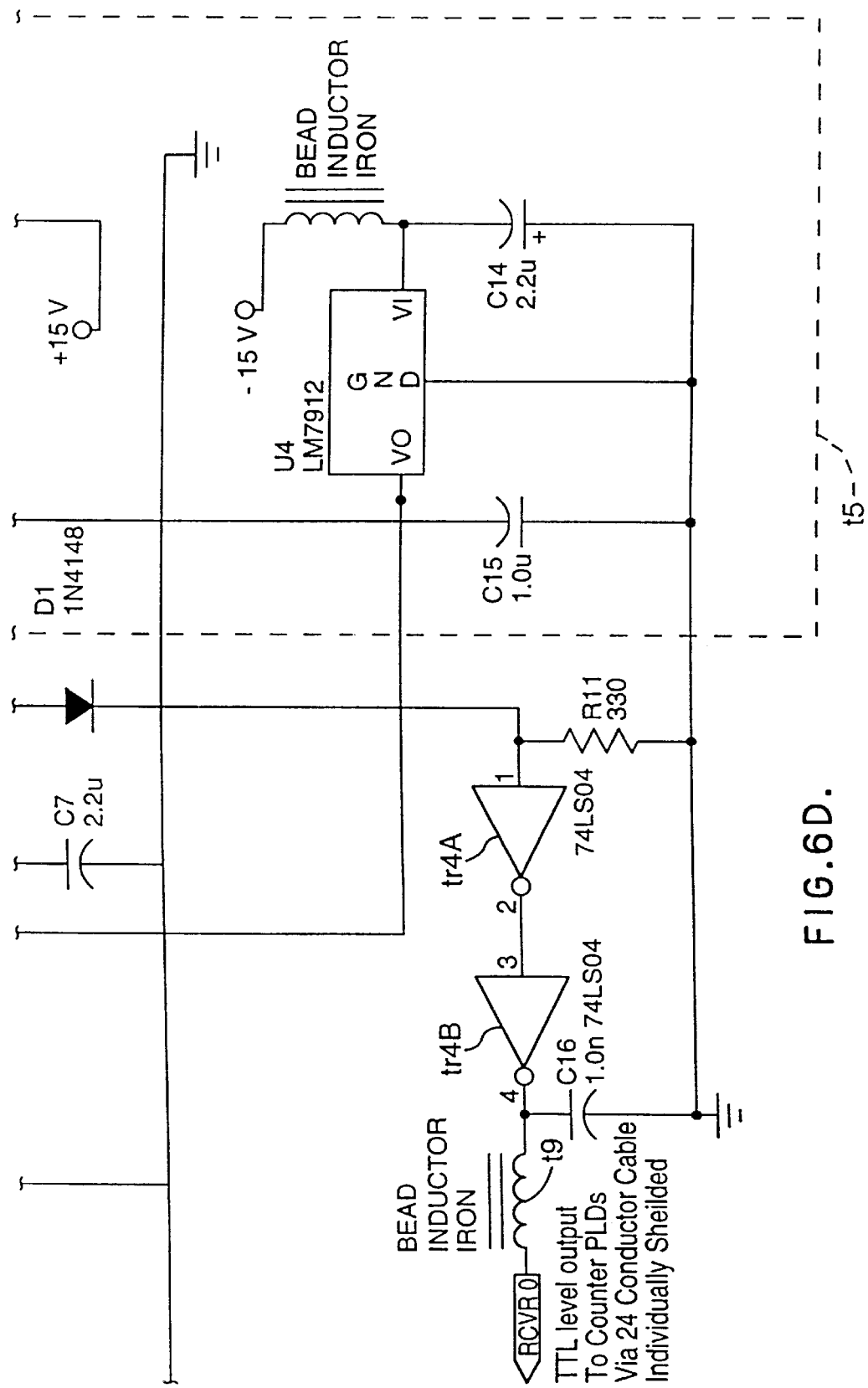

FIG. 2 is a block diagram of the computer interface and addressing scheme common to all three digital cards. It should be noted that the system is classified as an I/O mapping device as opposed to memory mapping device. Consequently, dedicated I/O registers within the controlling processor are responsible for all data throughput.

As illustrated in FIG. 2, the system computer interface architecture features a full two byte data transfer (DO-D15), as well as partial address decoding (A1–A13). Full two byte address decoding is not required. All signals sent to, or taken from the AT bus are buffered using octal buffers (d1 & d2) for both address and control lines, and transceivers (d3 & d4) for the data lines. In terms of decoding, each board features an eight position dip switch (d7) or equivalent for address selection. Address lines A6–A13 are used for this function, thus providing 256 distinct addressing locations, each with a resolution of 40 (hex) (i.e., 26). It should be noted that AO is not used for address decoding.

An 8-bit magnitude comparator (d5) is used to equate the manually set dip switch with address lines polled by the computer mother board. When a match is found, a signal is generated which gates demultiplexes d8 and d9, each of which is a 1-of-8 demultiplexes. The lower three address lines (A1–A3) are used as inputs to both of these Read and Write demultiplexes. To distinguish their functionality, the buffered IOR signal is sent to opposite polarity enables on each demultiplexer. Thus if IOR is in a high state, the system computer interface is in a Write mode. To avoid Reading and Writing from the I/O address ports, A4 is also used as an opposite polarity input to do and do. This has the effect of offsetting the Reads from the Writes by precisely 10 (hex) (i.e., 24). The result of this is two controllable ranges of eight data bits used for gating "reads" from the digital boards, and "writes" to the digital boards. A single PLD (d6) serves to handle the glue logic between the other components of the decoder circuitry.

Due to the architecture of the x86 family of microprocessors, there are only a finite amount of I/O registers. These registers can be partitioned into either 65535 8-bit registers, or 32767 16-bit registers. Due to the nature of the data transfers to and from the boards, and by selection of an active low signal to the I/O CS16 input of the AT bus, only 16-bit data transfers are employed by the system.

The only remaining control line extending to the digital circuit card is the Address Enable (EN). This signal is used in conjunction with the I/O Read and I/O Write signals to gate the magnitude comparator (d5). By doing so, Direct Memory Access (IQMA) conflicts are avoided between the tracking system and other internal computer modules of the PC.

The first functional module in the ultrasonic 3-D tracking system of the present invention is the controller card. A functional diagram is provided in FIG. 3, which comprises FIGS. 3A, 3B, 3C, 3D, 3E, 3P, 3G, 3H, 3I, 3J, 3K, 3L, 3M, 3N, 3O, 3P and 3Q. The controller card employs the identical bus decoding scheme described above with reference to FIG. 2, to govern and pace the functionality of the overall system. As with all of the digital cards, the controller is preferably a four layer Printed Circuit Board, (PCB), with the embedded layers being the power and the ground planes, respectively.

The operation of the card is as follows: A single Programmable Logic Device (PLD), c1, is programmed to cycle through a full two byte count at 32 MHz. The output registers of c1 are always active, so that the counter is constantly outputting a count value between 0 65535. These outputs are used for both comparative and timing purposes throughout the system. For this reason, a highly reliable, fast-response PLD is required.

Functional blocks C.—C. latch predetermined values from the decoding circuitry, and compare them to the output of c1. Thus, upon system start-up, specific values are written to the registers of C.—C., and once those values are matched by the output of c1, respective signals are generated to govern such features as Pulse Length (6-bit), Cycle Length (8-bit), and Inhibit (15-bit). As illustrated, the "equating" outputs of the low data byte comparison (c2 & c5) require an edge triggering flip-flop (c11) to hold their equated state. The Output of the high data byte comparator (c4) is of sufficient duration to feed directly to c10 and c12. Using a 80 MHz clock, the Pulse Length signal is variable between 0 $\mu$s and 2.00 $\mu$s at 31.25 ns increments, the Inhibit signal between 0 $\mu$s and 2.048 ms and 62.5 ns increments, and the Sub-Cycle Length signal is variable between 0 $\mu$s and 2.048 ms at 16 $\mu$s increments. Typical values are loaded into the registers of c2–c5 to best suit a given application, as discussed in greater detail below.

A second function of the c1 counter is to generate signals to a resetting 1-of-8 demultiplexes (c10) which in turn generates signals for application to c1 and c11 for resetting important system parameters. As can be seen in FIG. 3, one of these parameters is the Mode function which governs the direction of data flow in the octal transceivers located on the remaining system cards discussed in greater detail below. Four c1 outputs are also used to cycle through the RCVR lines of the system, thereby providing a default of 16 receiver modules.

A second major role of the controller card is to manage the performance of the transmitter activation bits. Using a transmitter PLD (c6) as a preloadable up counter, a value indicative of the start transmitter is latched to its input registers. Using an output of the c10 multiplexer as a clocking signal, c6 increments the six transmitter bits and outputs them both to a transparent buffer (c13), and to a 6-bit comparator (c9). Since the transmitter bits are sent to all three digital boards, as well as to the computer peripheral, the transparent buffer is required to avoid capacitive loading.

The ending transmit value is sent to the second side of the 6-bit comparator after it has been latched by c7. The octal latch (c8) is used simply to read the status of the transmitter bits by the controlling software. Once the 6-bit comparison is made and equated, a value is sent out to the local bus to clock the address incrementors on the remaining two digital cards. Although 6-bits are used for equating the transmitter increment bits, the default system allows for a 4-bit transmit value, corresponding to 16 possible transmitter channels. However, higher tier models of the ultrasonic tracking system of the present invention may employ up to 32 transmit cycles, corresponding to a 5-bit transmit value.

An 8-bit latch (c14) is also used by the system to generate and gate signals used to control address counters, interrupt controls, and trigger toggles.

Before most of the signals reach the local bus connecting the digital cards, they pass through c12, which is a simple "glue logic" PLD that ensures correct timing and signal polarity. This circuit module is also responsible for generating such parameters as the external system trigger for pacing and gating additional laboratory equipment.

Unlike the controller card which generates signals, the counter card (FIG. 4) receives signals to consolidate the ultrasonic distance information. The counter card features an external db25 connection to the transmitter/receiver/transceiver peripheral unit (FIG. 6). This twenty-four conductor, individually shielded connection between the counter card and the peripheral transmit/receive unit carries the 4-bit transmitter increment signals (TX BITS), the transmitter Pulse Length signals (CS1 and CS2) as well as the sixteen default receive lines accommodating 16 transmitter channels (upgradable to 32). Again it should be noted that not all embodiments of the ultrasonic 3-D tracking systems according to the present invention, employ the full range of sixteen receivers. Therefore, where a receive line is unused, it is grounded so as to avoid interfering with the desired signals.

A functional diagram of the counter card or module is provided in FIG. 4. The functionality of the counter module is best described in two stages, data writing and data reading. Examining the data writing stage, at precisely the moment when a valid signal is sent out by the external peripheral unit (FIG. 6) to activate a transmitting transducer, the expandable bank of receiver PLDs (s10–s13) are reset, to zero. These counters then count up from a zero value in accordance with respective internal 32 MHz clocks. Each PLD (s10–s13) is connected to an individual receive transducer (FIG. 6). As the 15-bit digital count in each PLD (s10–s13) is incremented past a predetermined value, an internal register within the PLD is activated which permits the reception of a receive signal. This predetermined value is used to implement the inhibit feature of the system and is designed to block out the electromagnetic interference caused by activating a transmit transducer. Once the mechanical vibration of the transmitted ultrasound is detected by a receive transducer it is converted to an electrical signal, amplified, filtered, and sent back to the appropriate counter PLD. This has the effect of stopping the digital count within the chip.

Next, a 1-of-16 multiplexer (s14) is activated for causing the output enable feature of the counters to be sequentially activated. The captured digital, value corresponding to the separation distance between the active transmitter and each connected receiver is then output in two bytes to the on-board RAM modules (s8 & s9) for temporary storage. Each time the RAM modules are activated, a default of sixteen locations are written to, according to the sixteen default receive signals. This cycle is then repeated for the next transmitter in the system. The incrementing of the RAM addresses is handled by s5, an octal buffer that outputs the 8-bit quantity representing the receiver/transmitter value at any time. Once all the transmitters in the system have been sequentially activated and recorded, the master cycle signal from the controller module triggers s1, the counter address incrementor PLD. This module then increments the RAM addresses to the next major block for the next transmit/receive master cycle.

Typically, the on-board RAM modules s8 & s9 are 8-bit by 131,072. Thus, in the-default configuration of sixteen transmitters and sixteen receivers, the RAM is cycled through 512 times before reaching its capacity. Options exist for upgrading the on-board RAM to 8-bit by 524,288, so as to allow for 2048 complete transmitter/receive cycles. It should be noted that for most biological investigations, a repetition frequency of 200 Hz is demanded. Thus, even with 256 kB of storage capacity (128 k×2), the on-board RAM can be completely filled in as little as 2.56 seconds. Consequently, the system of the present invention includes software functionality for downloading the stored information. This process is described in greater detail below.

To successfully realize the data reading stage, the counter card or module monitors the addresses that are automatically incremented to the RAM, and writes values to those addresses. This task is carried out by the octal transceivers (s2 & s3). Using the Mode function generated by the controller card, the addressing data shifts from a reading to a writing state in accordance with the system timing. This gives the software the ability to activate any address in the RAM by simply writing out a 16-bit value to s2 and s3. Since the incrementing of the transmitter and receiver bits is automatic, there is no need to monitor their value. Thus, s4 can be simply an octal D-type flip-flop rather than an octal transceiver.

Once an address is written to the RAM for data output, the octal buffers s6 and s7 are opened to permit the PLD distance data to be passed along the low and high byte data paths into the I/O registers of the motherboard processor, then to the computer RAM, and finally to the hard disk for permanent storage. As can be seen in the system timing diagrams (FIGS. 7 & 8), the system is in a data output mode for the majority of each system cycle. Data input to the RAM occurs regularly, but only for 8 $\mu$s intervals.

A second major function of the counter module or card is to provide an analog signal output. Despite the fact that digital data acquisition is superior in many ways to conventional analog circuitry, many users are required to work with analog signals. The Digital-to-Analog (DAC) converter (s17) is thereby provided as an option on the standard tracking units of the preferred embodiment. The DAC of the present invention operates as follows. Successive 8-bit values are latched into one side of the one of four magnitude comparator (s15b, d, f & h). These values are selectable through the software to permit any combination of transmitter/receiver output signals to be transferred to the four analog outputs. The opposite side of each comparator (s15b, d, f & h), is directly connected to the constantly cycling transmitter and receiver bits. When the value applied to both sides of a comparator are equal, the output is passed to a 4-to-2 line encoder (s16), before being passed to a DAC (s17). Under this configuration, four distinct, 12-bit analog channels can be connected to an output port from the computer.

Finally the counter card or module also employ a "glue logic" PLD (s18) to coordinate the timing of the output enable signals, as well as the handling of thirty-two versus sixteen transmit channel capability.

It should be noted that the foregoing counter card is suitably replaced by other types of well known timer modules which are configured to measure transit time.

The final digital card or module in the ultrasonic 3-D tracking system of the present invention is a synchronized Analog to Digital (A/D) converter card or module. During typical experiments, a user may wish to acquire more than the networked distance measurements. For example, in a cardiac investigation, analog signals such as pressure, ECG, and blood flow are also important. For this reason, an expandable A/D card is integrated into the tracking system of the preferred embodiment. The basic system is perfectly provided with four A/D channels. However, up to sixteen independent, 12-bit channels may also be provided ranging from ±10V.

As illustrated in FIG. 5, the A/D module functions in virtually the same fashion as the counter card. Analog channels are fed in via a db25 cable connection (RGB 174U coax connectors) to a1–a4. During the data input mode, all analog channels are internally converted fed into two 8-bit by 131,072 RAM modules (a6 & a7). The RAM is automatically incremented using the four gated receiver bits (a13). An incrementing address PLD (a14), which receives the same clock as the counter address incrementor, is used to provide the remaining thirteen address lines to the RAM. Thus, every time a complete transmit receive cycle is performed, both the A/D RAM and the counter RAM registers are increased. During the write, or data output mode, an address is written to the respective octal D-type flip-flop (a12) and transceivers (a10 & a11) to access the proper RAM location. The octal buffers a8 and a9 are opened allowing the converted analog information to be transmitted along the high and low byte data buses to the computer storage device. Finally, a controlling PLD (a5) is used to coordinate the timing signals on the A/D module. By congruously activating the A/D and counter information, it is possible to synchronize the digital distance information with the converted analog data.

A second function of the A/D card is to provide for direct digital inputs. Thus, up to four digital input channels may be received via latch a15 and monitored via octal buffer a8 during an experiment in the same fashion as the analog data.

The final hardware component in the ultrasonic 3-D tracking system of the present invention is the peripheral transmitter/receiver/transceiver unit, shown in FIG. 6. Each peripheral board of the preferred embodiment possesses the capacity to support sixteen transmitters with eight receivers, or eight transceivers. These components are mounted onto a two-layer printed circuit board and connected to the host computer system by means of the twenty-four conductor, individually shielded computer cable discussed above. The external peripheral unit receives its transmit voltage level and biasing voltages from an independent power supply (t5). The unit also possesses a two color LED to indicate whether the unit is in active or standby mode.

The peripheral unit works as follows. The digital signals from the computer to the unit are passed through pull up resistors to a CMS 1-of-16 decoder (try). The decoded signals are then transmitted to selectable transmitters or transceivers. The variable duration Pulse Length signal is sent via filtering and biasing elements to the gate of an N-Channel Enhancement Mode VMS transistor (Q). The gate signal bridges the transmit voltage level to ground. This signal is then passed through a step-up isolation transformer (TO) and out of the peripheral unit via a coated, 32 gauge, multi stranded wire (t2) to the transducer (x1).

The transducer (x1) is preferably a cylindrical piezoelectric ceramic crystal, encapsulated with an electrically insulating sealant.

Using a network of similar receivers, the mechanical vibration from a transmitter crystal is detected and converted to an electrical signal. Each individual receiver circuit consists of step-up isolation transformer (T1), a two stage amplifier (A1) collectively providing a 48 dB gain, a linear operational amplifier (tr3), a half-wave rectifier (D1) and a TTL level inverter (tr4A and tr4B). The digital waveform output from the TTL inverter is further isolated using an RF choke (t9) before it is transmitted back through the shielded cable to the appropriate LLDS.

According to the best mode of implementing the receiver, the single-ended amplifiers A1 may be replaced by a differential amplifier.

Figure 7A:
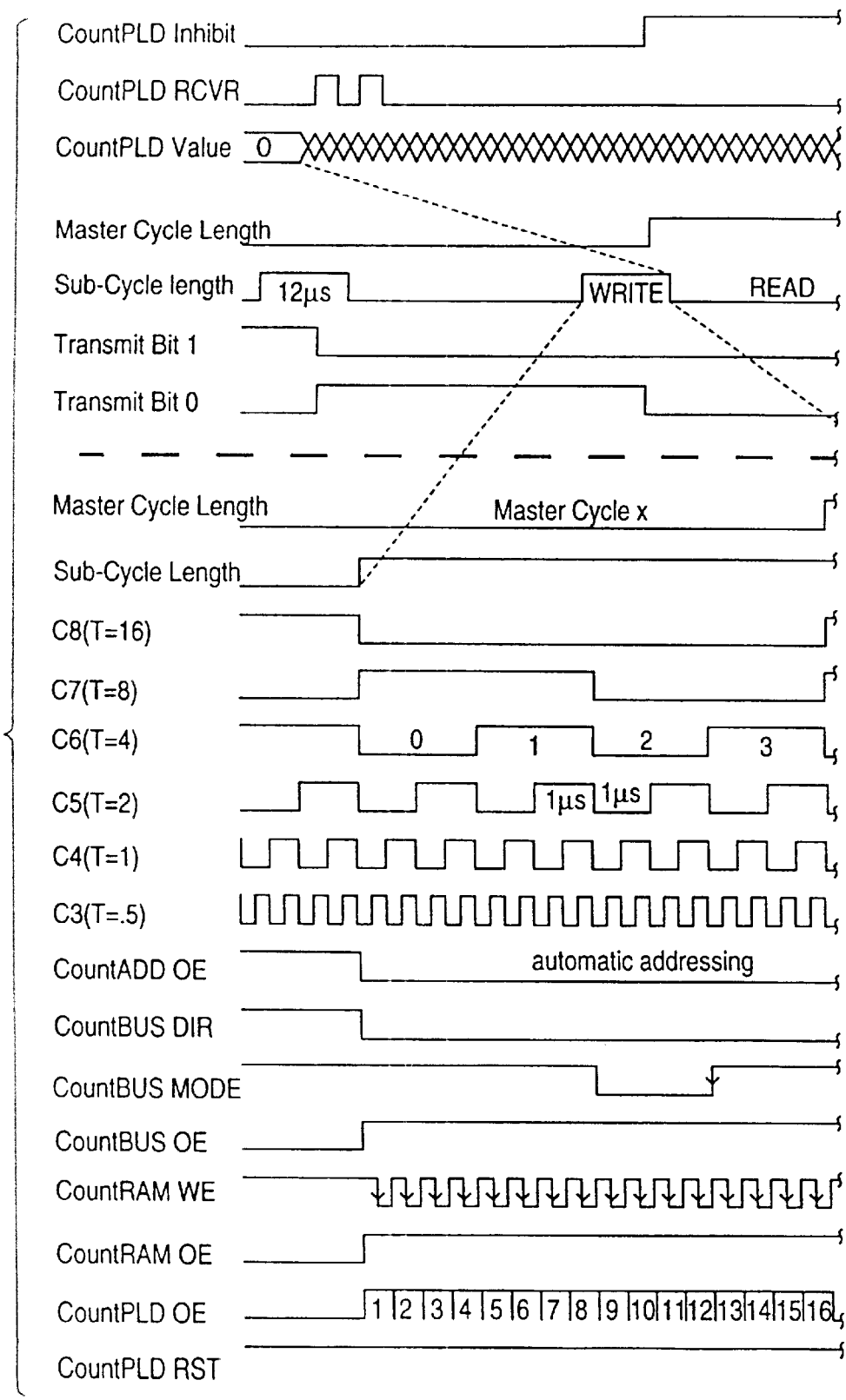
FIGS. 7A and 7B, is a timing diagram showing operation of the counter module according to the preferred embodiment.
Figure 7B:
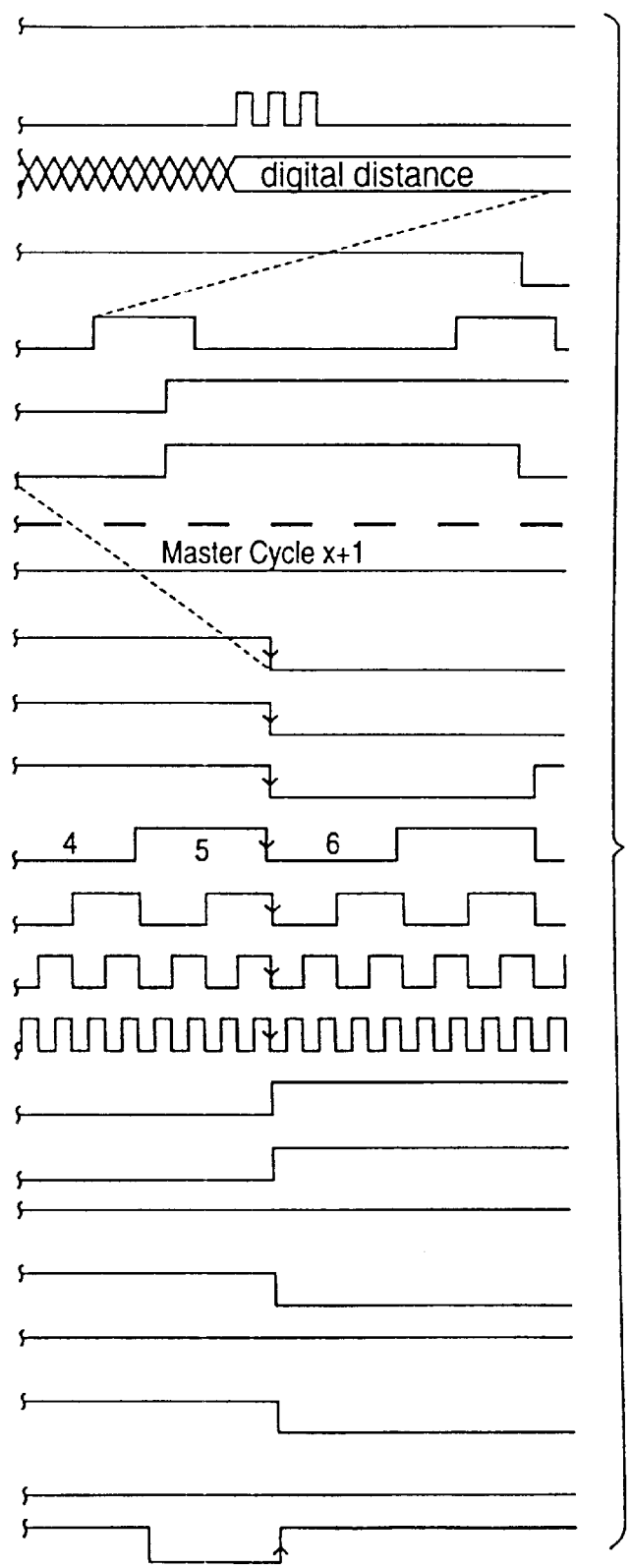
Figure 8A:
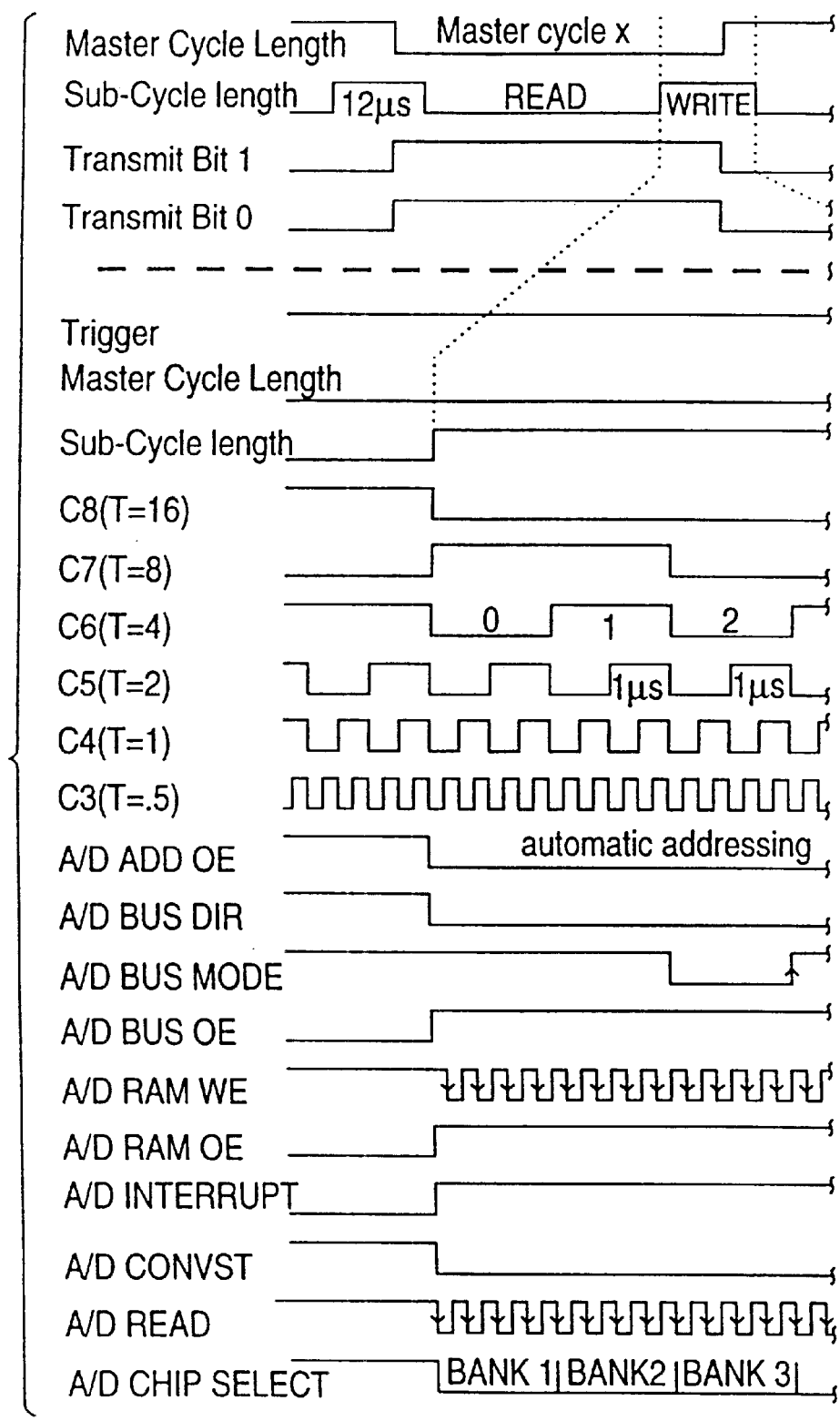
FIGS. 8A and 8B, is a timing diagram showing operation of the A/D module according to the preferred embodiment.
Figure 8B:
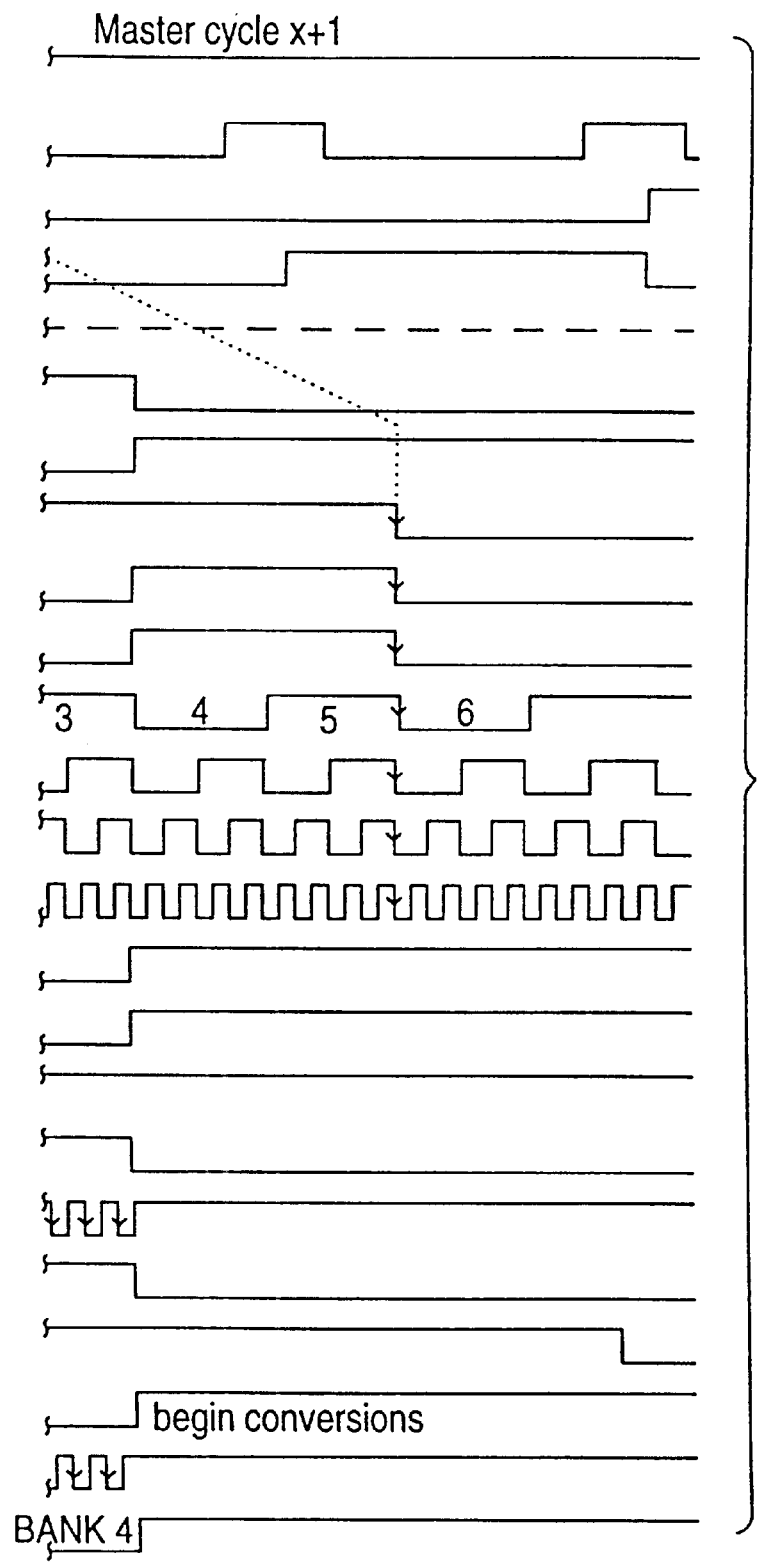

For a further understanding of the operation of the 3-D tracking system according to the present invention, a set of timing diagrams are provided in FIGS. 7 and 8. These figures illustrate the operation of the counter module (FIG. 4) and the A/D module (FIG. 5), respectively, during both the read and the write phases of operation. By default, the counter module actively acquires data for sixteen receivers during every Sub-Cycle Length. Conversely, the A/D data acquisition occurs only once during the same time interval, or once every Master Cycle Length. For simplicity, both timing diagrams are based on a transition from a transmitter "x" to a transmitter "x+1". Despite the apparent equal time-sharing between read and write cycles, in actual fact, the read cycle is significantly longer. More particularly, in the preferred embodiment the write cycle is limited to a 12 $\mu$s window per sub-cycle.

Referring to FIG. 7, the counter module (FIG. 4) operates as follows. At the beginning of the read cycle, an impulse signal is sent out to the VMS transistor (to in FIG. 6) to activate a transmit crystal (x1). At precisely the same time, the associated counter PLD (s10a–d, s13a–d) is released from its count of zero and begins counting up at a clock speed of 32 MHz. As discussed above, assertion of the CountPLD Inhibit signal prohibits electromagnetic interference between crystal leads by remaining at a logic low level. After a user-adjustable delay, the CountPLD signal changes state, thereby permitting the reception of a valid signal on the associated CountPLD RCVR line (RCVR0-3).

Once the first valid ultrasonic signal is detected and processed, the digital counter value is held on the PLD's output registers. The period of time for this distance count to occur is also variable in duration according to the user's specification. During this time, the transceivers which govern the read/write state of the system permit the downloading of the previously acquired digital distance values from the system RAM (s8,s9) (CountADD OE in a high state). By constantly monitoring the RAM addressing values using s2–s4 (FIG. 4) the computer is able to keep track of the RAM status. As the RAM (s8, s9, FIG. 4) approaches its capacity, a downloading is carried out during this read window.

The write window of operating the counter module is delimited by the 12 $\mu$s active high Sub-cycle length signal. At the moment this signal is asserted, the following conditions occur: the CountADD OE signal changes state, indicating that the automatic addressing mode has been invoked, the CountBUS DIR signal changes states to allow the opposite flow of data through the transceivers, the CountBUS OE signal is invoked to activate the output registers of the addressing PLD (s1) the CountRAM OE signal is disabled to prepare the RAM (s8, s9) for data storage, the CountPLD OE signal enables cycling through each of the sixteen individual counters, and the CountRAM WE signal toggles to store each digital count value in RAM (s8,s9). The signals used to control these functions are generated by various Boolean combinations of the control module counter (C.). As the default 4-bit receiver values are cycled through to produce the automatic RAM addressing, the CountBUS MODE signal is toggled to sample the current addressing value generated by the addressing PLD (s1, FIG. 4). This value is stored in memory for proper downloading of data during the next write window. These functions are carried out during the first 84 $\mu$s of the 12 $\mu$s sub-cycle window.

Once all sixteen receivers (FIG. 6) have downloaded their distance data to the RAM (s8, s9), the Master Cycle length value is incremented to indicate the next major cycle. At the same moment, the CountRAM WE signal is disabled along with the polling of the receiver distance values.

Finally the remaining 4 $\mu$s expire putting the counter module back into its read mode, while resetting the receiver chips (COUNTPLD RST), and each of the incrementing counter bits from the controller card (FIG. 3).

Using FIG. 8 as a guide, the A/D module of the ultrasonic 3-D tracking system works in an identical fashion as the counter module, with one major exception. Write modes occur only during transition of the Master Cycle Length signal. When such occur, the default sixteen converted analog channels are cycled through and written to their respective RAM locations. The same A/D BUS MODE sampling occurs to ensure individual RAM chips are provided in banks of four channels, each chip is given a 2 $\mu$s window in which the AID CHIP SELECT signal is toggled low for data throughput. At the end of 8 $\mu$s, the A/D parameters are reset to their write state while sampling of the analog channels begins once again. once the transition has occurred to activate the next array of transmitters, the AD INTERRUPT signal drops to a logic low value to indicate that the conversions of the active channels are complete.

The machine language codes that carry proper collection and processing of data acquired by the peripheral unit (FIG. 6) are all preferably based around a x86 processor. The transfer of information through the system is both quick and seamless. Given a typical system with sixteen transmitters and sixteen receivers, or sixteen transceivers, 256 2-byte distance data saves are carried out every cycle of the Master Cycle length signal. Since the on-board RAM (s8, s9) in a typical unit is 128 kB, the RAM has the capacity to save 512 Master Cycles before overwriting occurs. Since most clinical experiments typically demand a 200 Hz data saving rate to sufficiently track biological motion, only 2.56 seconds of data saving can be correctly obtained.

Since this is clearly unsatisfactory for a typical data run, software routines have been written for the system of the present invention to periodically download the RAM modules during the read cycles of the system.

The transfer of information out of the system is as follows: each time the digital boards (FIGS. 3–5) are accessed, a total of 1024 bytes of data are secured. This 1 kB is written to a dedicated 64 kB buffer in the mother board RAM of the resident PC. Provided that the computer is not responsible for carrying out any additional tasks, the machine language code implemented thereon, also shunts this information to the display. This function can be performed 64 times before the RAM buffer of the mother board RAM is full. Once this happens, the system software performs a binary save of the data held by the 64 kB buffer. At this stage, a standard disk-cache such as DOS's smartdrv.exe is activated to accept all of the 64 kB binary files and commit them to the hard disk drive of the PC at the end of a data save command. Under this scenario, the only limit to the duration of a data save is the capacity of the disk cache. In this manner, the ultrasonic 3-D tracking system of the present invention can be tailored to meet the specific needs of customers simply by providing additional memory to the base PC computer.

In addition to data saving and display software, the units according to the present invention preferably also utilize post-processing software routines to manipulate and visualize the saved binary data files.

Figure 16:
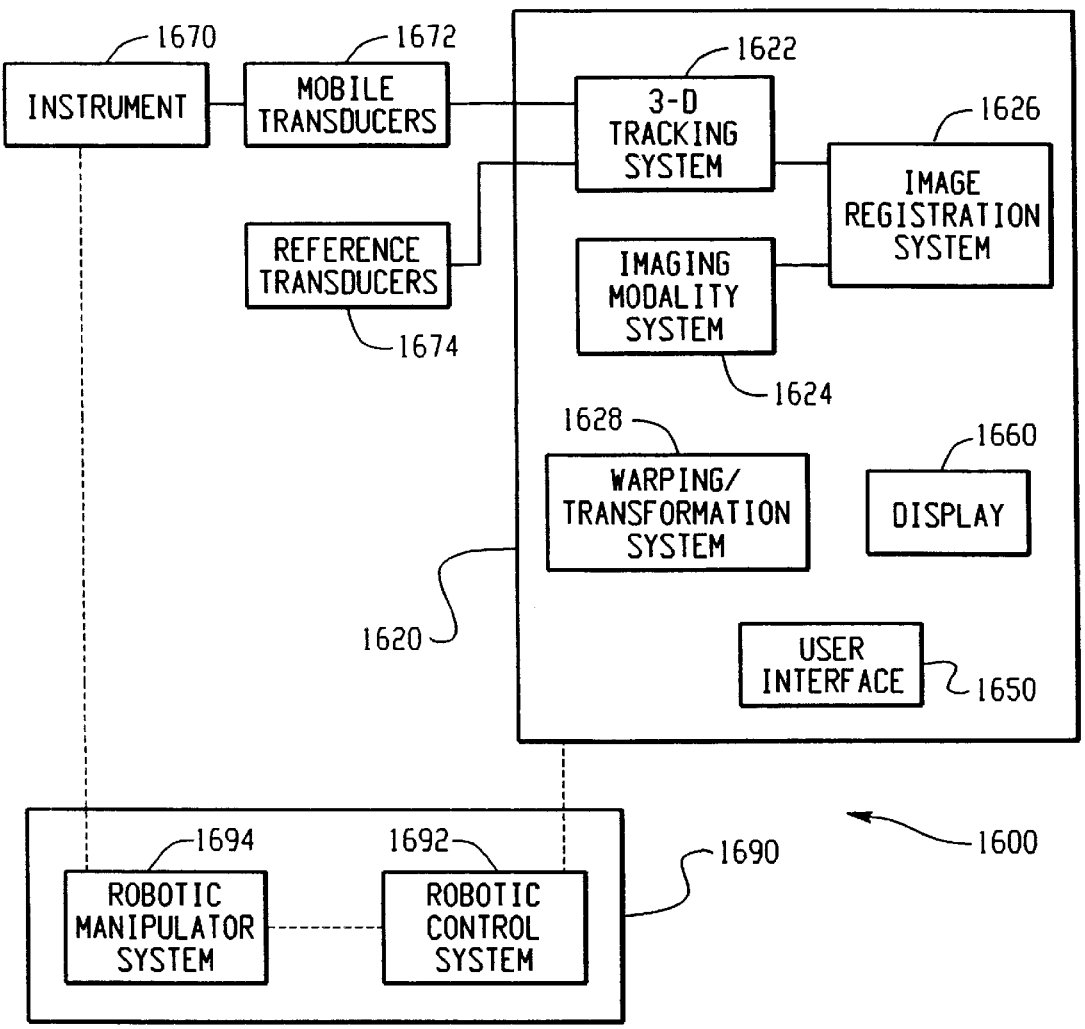
FIG. 16 is a block diagram of the 3-D tracking and imaging system according to a preferred embodiment of the present invention.

A three-dimensional (3-D) tracking and imaging system applicable for use in connection with a variety of procedures, including those described in detail below, will now be described with reference to FIG. 16. 3-D tracking and imaging system 1600 is generally comprised of a computer system 1620, mobile transducers 1672, reference transducers 1674, an instrument 1670 and an optional robotics subsystem 1690.

Computer system 1620 is generally comprised of a 3-D tracking system 1622, an imaging modality system 1624, an image registration system 1626, an image warping and geometry transformation system 1628 ("warp system"), a user interface 1650 and a display 1660. It should be appreciated that 3-D tracking system 1622 may take the form of a sound-based system or an electromagnetic-based system. Both time of flight and phase relationships may be used to determine distance.

Instrument 1670 may take the form of a catheter (e.g., see FIG. 10), a probe, a sensor, a needle, a scalpel, a forcep or other device used in a surgical or diagnostic procedure. Mobile transducers 1672 and reference transducers 1674 may take the form of an ultrasonic transducer or an electronic transducer. However, for purpose of illustrating a preferred embodiment of the present invention, transducers 1672 and 1674 will take the form of ultrasonic transducers (i.e., piezoelectric crystals) described above.

A plurality of mobile transducers 1672 are fitted to instrument 1670. One or more reference transducers 1674 provide a reference position relative to mobile transducers 1672. In this respect, reference transducers 1674 may be located to provide an internal reference frame inside a patient's body or on the surface of a patient body to provide an external reference frame.

As indicated above, reference transducers 1674 may be transmitters, transceivers or receivers that can generate ultrasound or electromagnetic radiation, that can be detected by mobile transducers 1672.

For the purpose of illustrating a preferred embodiment of the present invention, 3-D tracking system 1622 will take the form of the ultrasonic 3-D tracking system described in detail above. 3-D tracking system 1622 transforms the multiple distance measurements between all of the transducers 1672, 1674 into XYZ coordinates relative to a referenced axis, as described in detail above. It should be appreciated that the reference frame provided by reference transducers 1674 must be self-determining, that is, if the reference frame becomes distorted, this distortion needs to be detected by reference transducers 1674. Detection is typically done by using transceivers that can determine the distance between any combination of two transducers, and hence their relative spacial coordinates in 3-D space. In this regard, the position of the transducers is obtained in 3-D from the images acquired of the bodily structure (e.g., tissue/organ) that show "dots" where the transducers are located, and also from the transducers themselves when they are in the bodily structure. If there is some discrepancy in the distances between all combinations of transducers, then the bodily structure must have deformed (i.e., "warped") after the images were acquired. A mathematical coordinate transformation can be used to specify exactly how to correct the image set and account for the warping. The distance between any combination of two transducers is determined by having each transducer send a signal to all other transducers. In this way, all the distances between the transducers is known. From these distances, XYZ coordinates can be calculated, in reference to some transducer as the origin.

Imaging modality system 1624 acquires 2-D, 3-D or 4-D image data sets from an imaging source, such as fluoroscopy, an MRI (magnetic resonance imaging), CT (computerized tomography) or 2-D or 3-D ultrasound device, to provide a "template" through or against which the shape, position and movement of instrument 1670 being tracked can be displayed. The template typically takes the form of an image of the environment surrounding the instrument (e.g., a bodily structure). It should be noted that if multiple (3-D) volumes are acquired at different time intervals, a 4-D image is obtained (i.e., 3-D image changing over time).

Image registration system 1626 registers the position of instrument 1570 within the spatial coordinates of the image data set provided by imaging modality system 1624. The position of instrument 1670 is provided by the 3-D tracking system 1622. Image registration system 1626 will provide a display of instrument 1670 at its proper 3-D location inside the bodily structure and orientation relative to the bodily structure itself. It should be appreciated that registration system 1626 may be user assisted, or completely automated if image processing algorithms are implemented to automatically detect the spacial locations of the transducers (typically the reference transducers) in the image data set.

Warp system 1628 is a software-based system that transforms or "warps" the image data sets by the appropriate values to correspond to a deformation that has occurred in the reference frame between the time that the image data set were acquired and the time that the procedure is to be implemented during surgery. Accordingly, warp system 1628 is typically comprised of a matrix transformation routine that maps the deformed geometry onto the original image data set, and distorts it appropriately.

User interface 1650 enables a user to interact with computer system 1620, including programming computer system 1620 to perform a desired function. For example, a particular view for display can be selected. Instruments 1670 (e.g., probes or catheters) can be activated using user interface 1650. Display 1660 displays to the user registered images provided by image registration system 1626.

Optional robotics system 1690 is generally comprised of a robotics control system 1692 and a robotic manipulator system 1694. Robotics control system 1692 controls robotic manipulator system 1694 to follow a programmed path that can be appropriately changed, based on shifting, warping or changes in the shape of a bodily structure at the time of surgery. Robotic manipulator system 1694 physically moves instrument 1670 as instructed by robotic control system 1692.

As discussed above, 3-D tracking and imaging system 1600 can display existing or user acquired image data sets as a template through which, or against which the position, shape or motion of an instrument can be referenced inside the body or organ. The algorithm for carrying out this feature will now be described with reference to FIG. 11. It should be appreciated that portions of the "Path 1" algorithm can run both on the PC that houses the circuit boards embodying FIGS. 2–6 ("PC"), and/or in a separate computer (not shown) or workstation ("WS") with additional processing power and 3-D visualization capability.

The process begins with the PC that houses the digital circuit boards. The PC completes a data acquisition cycle and has many numbers in memory, each corresponding to a time that the ultrasound pulse took to travel the distance between all combinations of transducers within the measuring volume (module 1100). Within this volume, there exist a number of mobile transducers mounted on the instruments being tracked(see FIG. 9), as well as reference transducers located on the patient in strategic reference locations (see FIG. 15). The reference transducers may be mounted internal to the patient to provide an internal reference frame, or mounted external to provide an external reference frame. This propagation delay measure, or "signal", can be corrupted with noise, accordingly some signal processing may be need to be performed to recover the likely values of the original signal (module 1102). This can be done by testing for the range of the signal, and by smoothing or predictive fitting to previous trajectories of the data signal.

Following signal processing, the improved "signal" is converted in the PC, according to the methodology discussed in detail above with reference to FIGS. 2–8, into "data" that correspond to real measurements of distance between pairs of transducers. This is done by converting the propagation delay into a distance measurement by taking into account the speed of sound in the particular medium. This conversion can be a simple linear process, or can be scaled non-linearly, depending on the likely medium through which the sound is propagating. The output of this conversion is distance measurement "data" (module 1104).

It should be appreciated that the distance measurement data may be corrupted due to signal dropouts resulting from poor signal propagation throughout the measurement volume. However, there usually are more than enough individual distance measurements available to reconstruct the 3-D location of the transducers, since many extra distances between transducer pairs are obtained. A process of "data filling" can be performed to fill in the missing data, based on the many combinations of other distance measurements that are available. "Data filling" can be done using a 'multidimensional scaling algorithm, or variants of it. "Data filling" is an iterative process and is typically done on the computer workstation ("WS"). The output of the "data filling" preprocessing step is more complete data.

The data output from module 1106 is then converted (in a well known manner using geometric algorithms) into 3-D coordinates of the points that are being tracked (module 1108). These 3-D coordinates are passed to a 3-D scene relationship and evaluation module that takes the 3-D coordinates, and based on previously obtained information from user input or a library database, arranges the coordinates in the correct sequence to construct 3-D structures (module 1110). For example, it would be known in advance that, for example, transducers numbered 3, 5, 6 and 9 are mounted on a predetermined one of the instruments (e.g., a catheter), so the coordinates of the transducers mounted to the instrument would be connected together. The scene relationship and evaluation module would then construct a 3-D image that would represent the position, size and shape of the instrument, based on the 3-D coordinates of the individual transducers mounted to the instrument body.

In a similar manner, the transducers mounted to the instrument can be located in such a way as to build up a 3-D surface patch image of a bodily structure, such as an organ. For example, transducers mounted to a catheter can be located in such a way as to build up a 3-D surface patch image of the inside of a beating ventricle, by simply dragging the catheter along the wall of the ventricle in the area of interest.

Figure 15:
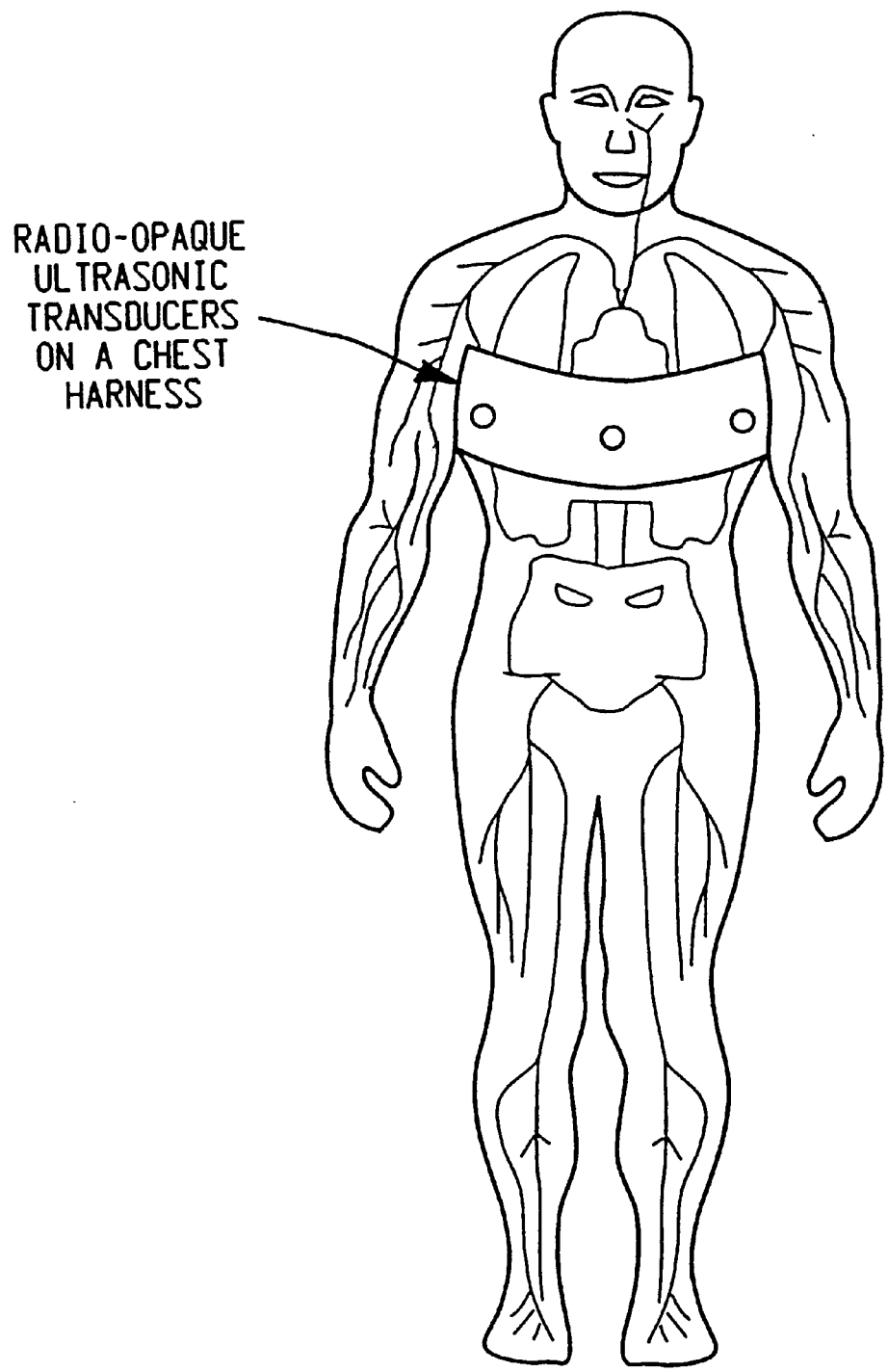
FIG. 15 is a schematic illustration of the external reference frame of the catheter guidance system according to the implementation of FIG. 9.

The output of module 1110 is a '3-D scene' that contains many of the elements being processed, some of which represent the instrument and the individual transducers affixed to the patient (FIG. 15). The 3-D scene is then rendered by a 3-D graphics subsystem rendering/display (module 1112) and output to a display.

If the instrument is stationary, the 3-D scene does not need to be re-rendered or updated in any way. Therefore, a module 1114 is provided that detects any changes in the stream of incoming data. If there are changes, this module signals another module 1116 that determines whether the new 3-D coordinates that have been acquired and processed by the WS have changed significantly from the previously rendered objects or scene. If they have, then this updated information is incorporated into the existing model of the 2-D scene and passed onto the rendering/display module 1112.

The display of the instruments is only one component of the scene relationship and visualization module 1110. In this regard, the instruments need to be displayed in reference to some recognizable features, such as a 2-D or 3-D image showing the environment surrounding the instrument. The algorithm for carrying out external image acquisition is shown schematically in FIG. 11 as "Path 2", and begins with the input of an image from an external image modality (module 1118). As discussed above, system 1600 includes an imagining modality system 1624 providing externally acquired image data sets in 2-D or 3-D form. It should be appreciated that these 2-D or 3-D images may already be in digital form, or may be analog data input directly from a live video source using a frame grabber.

The acquired image data sets must first be converted into a format that is suitable for processing and manipulation inside the WS (module 1120). Accordingly, any analog data is converted to digit data. Therefore, the image data sets that are output from module 1120 are "digital images" that can be manipulated further inside the WS.

The image data sets may need to be preprocessed in some way to make them fit appropriately into the 3-D scene. For instance, if they are to be shown along with the instruments, the image data sets may need to be scaled appropriately. If the images are to be moving, they will need to be updated or reformatted in memory so that they can be output to the 3-D scene rendering/display module 1112 in the correct sequence. Any such manipulation is performed by the preprocessing module 1122. Moreover, for video information, an appropriate sync signal is required for appropriate sequencing (module 1124).

One of the most critical aspects of the 3-D scene relationship and evaluation module 1110 is the placement of the 3-D image of the instrument in the correct spatial relationship with the underlying images showing the environment surrounding the instrument. This is done by registering features in the images, such as the reference transducers, with their position in the measuring coordinate system. This process uses standard coordinate transformation operations, and only requires for input information as to which feature in the image space corresponds to the same feature (i.e., transducer) in the measurement space. This information can be input by the user during initial set up (module 1126), or can be automatically detected using image processing algorithms. Once the instrument image is registered with the underlying images, the information describing the image set that is to be displayed at a given instant is sent to the 3-D scene relationship evaluator module 1110. Additionally, to test whether new image information has arrived and needs to be used, an appropriate signal is sent to module 1114 that detects changes and instructs the system to update the scene.

Figure 11:
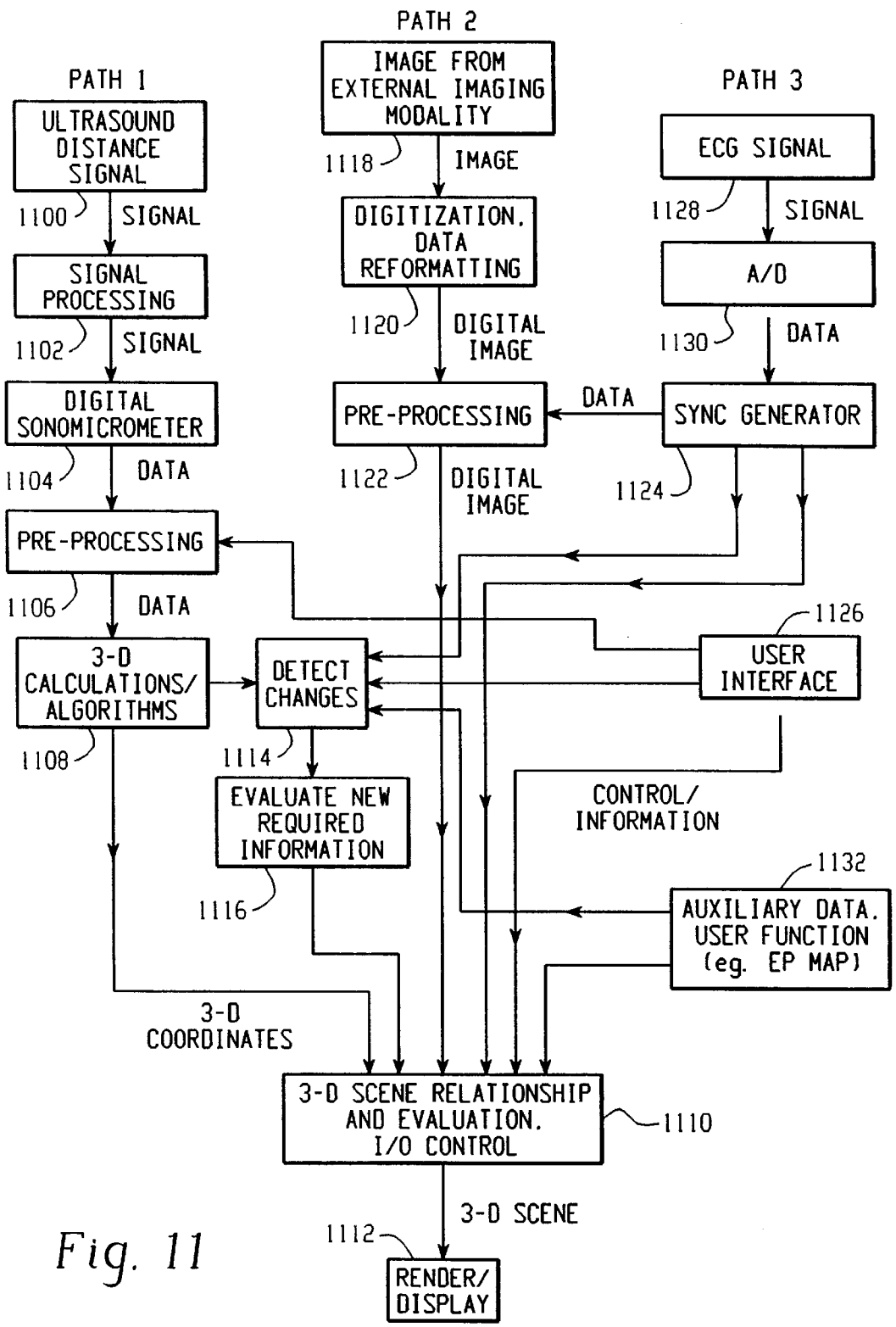
FIG. 11 is a flow chart of a 3-D visualization algorithm which uses the tracking system of the present invention.

For moving image sets, such as 2-D video loops, or 3-D ultrasound loops of the heart, the motion of the image data sets need to be output at a rate that continually matches that of the patient heart beat (see Path 3 in FIG. 11). If the image data set that is played back is not synchronized with the current state of the heart, then the 3-D scene will not be displayed in a recognizable format and abnormal motion of the catheters relative to the images, will result.

The first step in synchronizing "video loops" with a patient's heart beat is to input a raw ECG signal into the processing computer (module 1128). The ECG signal is converted into digital data using a standard A/D converter (module 1130). The digital data is then fed into sync generator module 1124, which includes an algorithm that produces a timing signal that corresponds to the current activity of the heart. For example, the sync generator module 1124 can activate a memory location or an input port, or generate an interrupt, at the precise time that a QRS complex is identified. The sync generator module 1124 does this by following the input signal and testing for large rates of change, combined with zero crossing and other information relevant to the expected morphology of the signal. The sync generator module 1124 can run in the PC, the WS, or an external device designed to identify QRS complexes and output a sync signal to the WS.

Control information is provided by the user interface (module 1126), discussed above. The user interface checks for user input from a keyboard and/or mouse and sends appropriate control information to the 3-D scene generator (module 1110), and to other modules that can be affected by the user input. Typically, user input would involve the modification of the type of information that is to be displayed on the display screen, and not the way the signals are processed. The user can also assist in registering the catheter location of the instrument with the underlying image set.

The system also has a provision for the merging of other auxiliary data information, such as the display of electric potential over any 3-D structures that are displayed (module 1132). This information is peripheral to this main system, and is assembled in a way that can be readily incorporated into the 3-D scene generator (module 1110).

Figure 12:
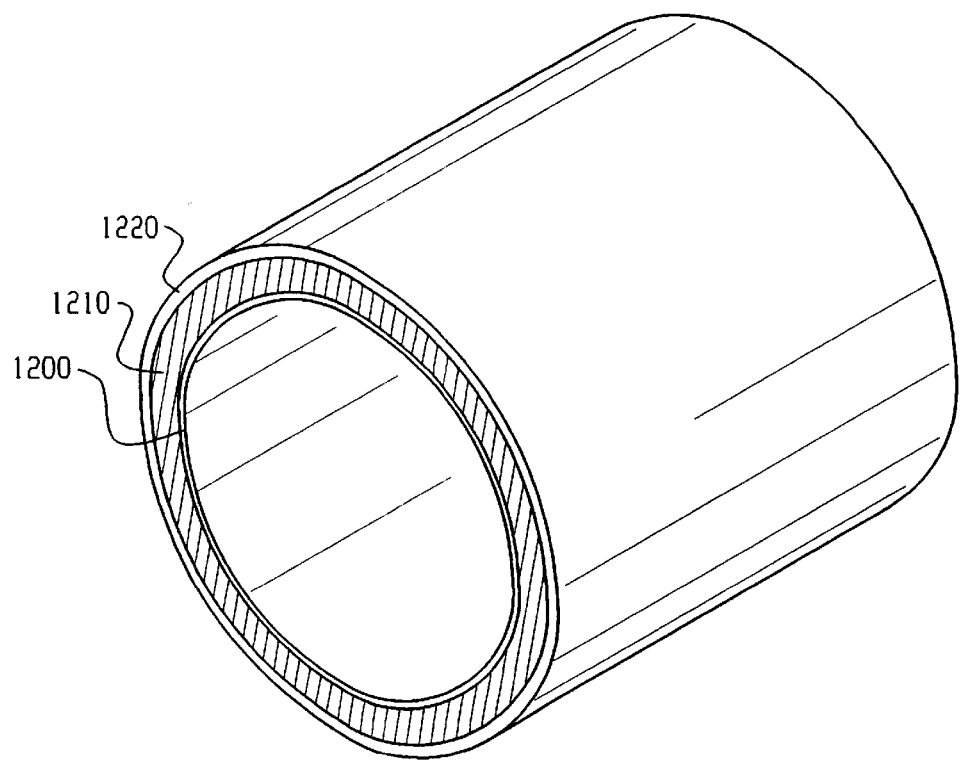
FIG. 12 is a perspective view of a cylindrical or ring-shaped transducer according to a first alternative.

As indicated above, the transducer of the present invention may take many forms. According to a first alternative embodiment, a cylindrical or ring shaped ultrasonic transducer is provided, as shown in FIG. 12, for attachment to an instrument (e.g., a catheter or other probe), for the purpose of tracking its position in three dimensions inside the body or organ. The transducers can be either rigid or flexible. If they are rigid, they are typically constructed from PZT material, and cast or milled into an appropriate shape. If the transducers are made flexible, they are typically constructed from PVDF material that is laminated onto the surface of an instrument. This material is flexible and can be applied to rounded surfaces. As a result of the relatively low transmit efficiency of PVDF material, it is likely to be used for a transducer used in receive mode only. The geometry of the crystal preferably has principal mode of vibration in the 100 kilohertz to 4 megahertz range, or in the range referred to as "low frequency ultrasound". The transducers are polarized along a principal axis (i.e., either through the wall thickness, or along the cylindrical axis) and the appropriate surfaces are coated with a conductive material to facilitate connection to leads. If the material is poled through the wall thickness, then the inner and outer surfaces of the cylinder are plated and conductors are affixed thereto. While the size of the transducer will depend on the application of the tracking technology, the inner diameter of the cylinder is typically 5 millimeters or less for catheters and 5 millimeters or more for larger endoscopic probes. It should also be appreciated that several sections of a cylinder may be placed around the instrument of interest, thus making each individual transducer small for ease of manufacture, mounting or to control resonant frequency.

As shown in FIG. 12, the cylindrical crystal or transducer may incorporate a lossy backing 1200 on which the piezoelectric material 1210 is disposed. The lossy backing prevents excessive ringing of the PZT material. As the crystal is energized, an ultrasound wave propagates both forward and backward. When the ultrasound wave reaches the interface between the crystal and the outside medium (e.g., water or air) it meets an impedance mismatch and most of the wave bounces back into the crystal. This is why the crystal rings for many cycles. The lossy backing enables the backwards traveling wave to exit the crystal (i.e., it has similar impedance) and dissipate with minimal reflection. The backing material is typically-epoxy with tungsten powder mixed in. Ideally, the backing material should be many times thicker than the crystal itself The piezoelectric material 1210 may be coated with a ¼ wavelength matching layer of ultrasound conductive material 1220 (e.g., polymer material). Electrically conductive wires (not shown) are connected to the piezoelectric material. As discussed above, the forward propagating wave of ultrasound typically bounces off of the crystal/water interface, unless some impedance matching material is provided. The purpose of this material is to provide an intermediate impedance between water and PZT so that at each material interface there is less mismatch, and more of the ultrasound wave propagates forward, rather than reflecting backward. Typically one or two layers are deposited on the crystal with intermediate impedances. The thickness of the layers must be ¼ of the wavelength of the ultrasound wave so that destructive interface occurs between the reflected waves, thus reducing the ringing of the crystal.

If PVDF is used for the piezoelectric material 1210, then the film or material can be wrapped around the instrument, or could be molded or cast directly upon it, essentially becoming a component of the instrument. It is also contemplated that an existing instrument (.e.g., catheter) can be retrofitted with PVDF material in accordance with the embodiment of FIG. 12, to facilitate tracking thereof inside the body. It is also contemplated that the piezoelectric film (e.g., PVDF) can be wrapped, cast or deposited over the instrument in several locations.

Figure 13B:
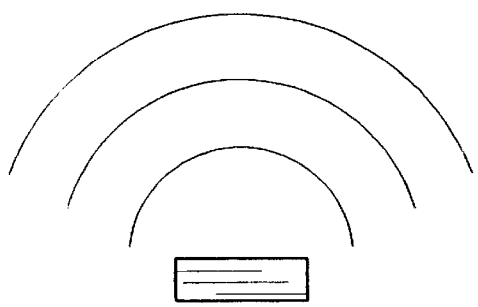
FIG. 13 is a perspective view of a ring-shaped array of crystals, according to a second alternative embodiment.
Figure 13C:
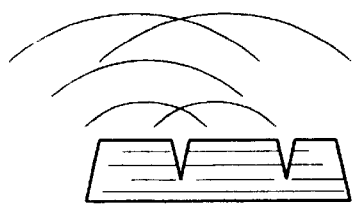
Figure 13A:
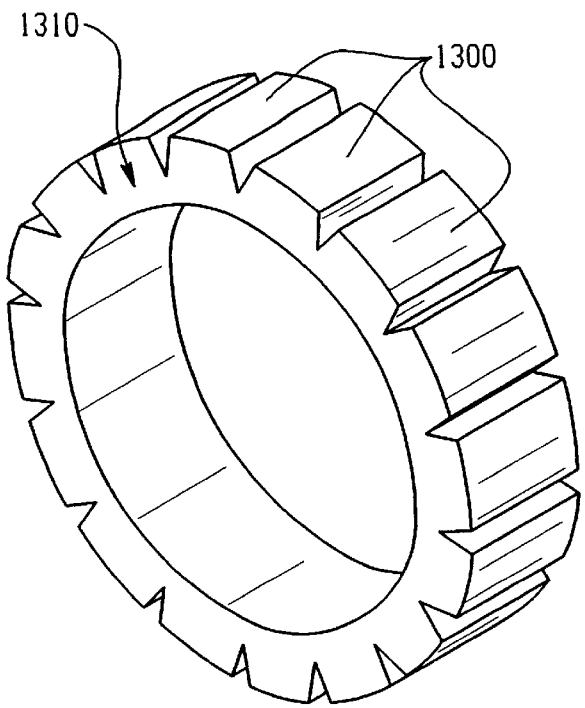

According to a second alternative embodiment for the ultrasonic transducer, a ring-shaped array of crystals, or a segmented single crystal can be provided, as shown in FIG. 13A, with a configuration that enables the ultrasound energy to radiate at a large angle away from perpendicular to the axis of the cylinder, such that the crystal array functions as a line source of ultrasound energy, or as a collection of point sources, each radiating ultrasound energy in a fan substantially away from the plane of the cylinder, as shown in FIGS. 13B and 13C.

The crystal is provided with a plurality of facets 1300, each being in the order of a millimeter in size, so as to resonate individually at a resonant frequency dictated by the size of the facet, rather than the size of the entire ring. The ring is plated with a conductor 1310 on both sides, as depicted in FIG. 13, rather than on the inner and outer surfaces thereof.

Figure 14:
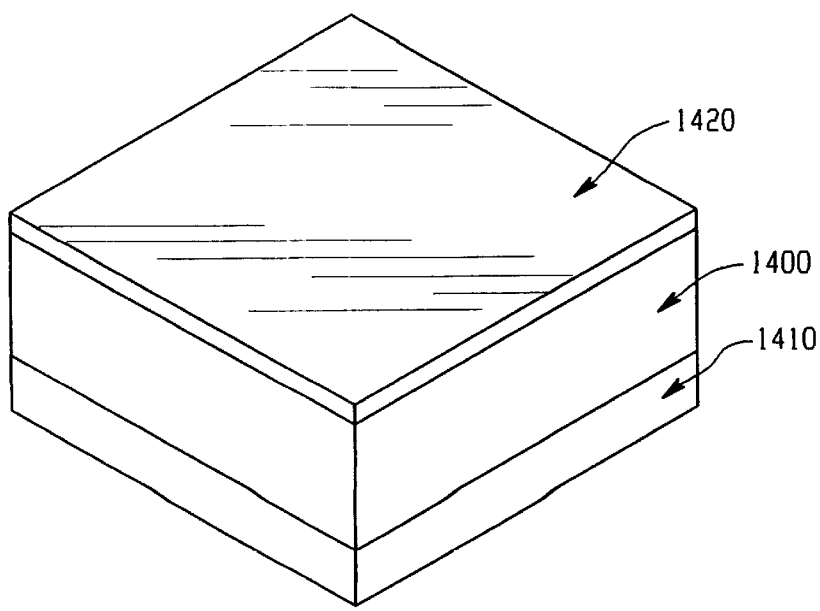
FIG. 14 is a perspective view of a composite transducer, according to a third alternative embodiment.

According to a third embodiment of the transducer, a composite ultrasonic transducer is provided comprising a PZT substrate 1400 on a lossy backing 1410. A PVDF film 1420 is bonded to the PZT substrate 1400. This embodiment offers the advantages of high transmitting efficiency of PZT (i.e., conversion of electrical energy into acoustical energy) and the high receiving efficiency of PVDF (i.e., conversion of acoustical energy into electrical energy). It is contemplated that the PVDF and PZT films 1420 and 1400 can be directly connected (as shown), or electrically isolated with appropriate layers of insulator or conductor therebetween. It is also contemplated that the PVDF or PZT structure can be in the form of a slab, as shown in FIG. 14, or can be cylindrical, as in the embodiments of FIGS. 9, 10, 12 or 13.

FIG. 15 illustrates the manner in which the external reference transducers are placed. The purpose of the external reference transducer is to provide an external reference frame (i.e., outside the body) to monitor the accuracy and movement of the transducers mounted on the instrument. As can be seen, the transducers are placed in a harness-type apparatus that is worn around the chest by the patient during a surgical procedure. A number of radio-opaque transducers are fastened to the harness in locations suitable for optimal signal reception through the chest cavity. Alternatively, the external reference transducer may be affixed directly to the patient at strategic locations, using self adhesive mounting film or adhesive tape.

Under the disclosed configuration, it is possible to monitor the position and direction of the instruments that are introduced into the body, (e.g., catheters introduced into the human circulatory system). This methodology significantly reduces both the risk and the procedural time associated with current electrophysiology and angiology operations, while providing improved positioning accuracy.

A detailed description of various exemplary medical procedures using the 3-D tracking and imaging system described above, are set forth below.

i) Tracking of Catheters Through the Human Circulatory System

Catheters are devices that are inserted into the veins or arteries of humans as part of a procedure in which qualified hospital personnel, remove blockages and obstructions from the circulatory system, or correct other related problems. The 3-D tracking and imaging system of the present invention may be configured to operate as a catheter guidance system (CGS) that can be used to track various types of instruments, including catheters, probes and needles.

The current method of tracking catheters involves frequent exposure of the patient to an x-ray source. Each successive x-ray provides information on the movement of the catheters within the patient. In addition, contrast agents are frequently injected into patients during catheter procedures. These injections can provide further information on the actual location of the catheter and help physicians to plan subsequent catheter movements.

X-ray radiation and contrast agent injections are each potentially harmful to the health of the patient. Further, these methods of tracking are also time consuming, often introducing additional stress and patient complications.

Three primary advantages result from the present invention when used to track catheters:

1) The need for using harmful x-rays and contrast agents are virtually eliminated while determining the location of catheters) within the patient;
2) Procedure times are substantially reduced with benefits in both safety and cost; and
3) Extremely exact positioning of the catheter is obtained as a result of the theoretical resolution of 19 $\mu$m, according to the present embodiment of the system.

The basic principle of the catheter guidance system (CGS) of the present invention involves the establishment of an internal reference frame and an (optional) external reference frame in three dimensions from which the catheter can be tracked. Using the transceiver hardware and the triangulation algorithm discussed above, the crystal positioning data can be captured and processed to resolve the location of the catheter of interest.

To further facilitate visualization of the catheter location by the administering hospital staff, the transducer position information may be overlaid onto a recorded video loop of the region of interest. This video loop can be generated from an imaging modality such as x-ray or scanning ultrasound and is meant to illustrate the natural movement of the biological structures during one or more cardiac cycles. In addition to this, the video loop can also depict the position of the opaque piezoelectric crystals (X1) used by the CGS to track the catheters. These piezoelectric crystals serve as "landmarks" (whether they are internal or external). By identifing these "landmarks" in the video, the positions of the guiding piezoelectric crystals can be correlated with the captured video information. In this fashion, the imaging process and the ultrasound positioning process can be linked for one or more complete cardiac cycles. Once the imaging modalities are linked, the graphic video loop can be substituted for the potentially harmful imaging (and contrast agent injections) throughout the rest of the procedure.

Typically, the catheters used in these procedures are introduced into the body through the femoral vein or artery, or through the carotid. From the point of entry, the catheters are pushed and steered, sometimes using internal guide wires to the region of interest, usually the human heart. Physically, the catheters are constructed with a biocompatible plastic and feature such options as electrode sensors and actuators for detecting the cardiac activity in electrophysical operations to inflatable balloons for arterial expansion in angiology procedures.

A concept that is of importance in implementing the CGS application of the present invention is the merging of piezoelectric crystals and the imaged catheters. Since the design of catheters used for these procedures are well established, consideration has been given to the design of the ultrasonic sensor, including the following aspects:

1. The type of piezoelectric material used.
2. The encapsulation procedure.
3. The shape of the transducer.
4. The operating frequency.
5. The activation procedure.

The material selected for use in both the internal and external reference frames must possess superior transmission and reception characteristics in order to properly communicate with each other. Since operating temperatures inside the human body are not a major concern, a higher dielectric material with lower Curie temperature can be employed. Essentially, this provides for an increased ultrasonic output per input volt. The preferred material for this purpose is PZT (lead zirconate titanate).

Since these materials are non-biocompatible, an appropriate encapsulation material is used. The encapsulant must not only be biocompatible, but must also possess an acoustic impedance that does not hinder the ultrasonic wave propagation. This is of key importance for the internal reference frame transducers.

The external reference transducer crystals require an acoustic coupling gel similar to that used for standard B-type ultrasound scans. Omni-directional ultrasound transmission, cylindrical crystals (X1) are used for the internal reference frame. The cylindrical crystals maintain omni-directional radiation patterns while demonstrating excellent transmission and reception characteristics. Externally, larger disktype or hemispherical crystals are employed for the reference transducers.

Due to the variable software controls of the 3-D tracking and imaging system according to the present invention, the activation frequency can be optimized for maximum performance and efficiency. In the case of the internal reference frame, smaller distances are monitored, therefore higher activation cycle frequencies can be used. The opposite is true of the external reference frame.

Figure 9:
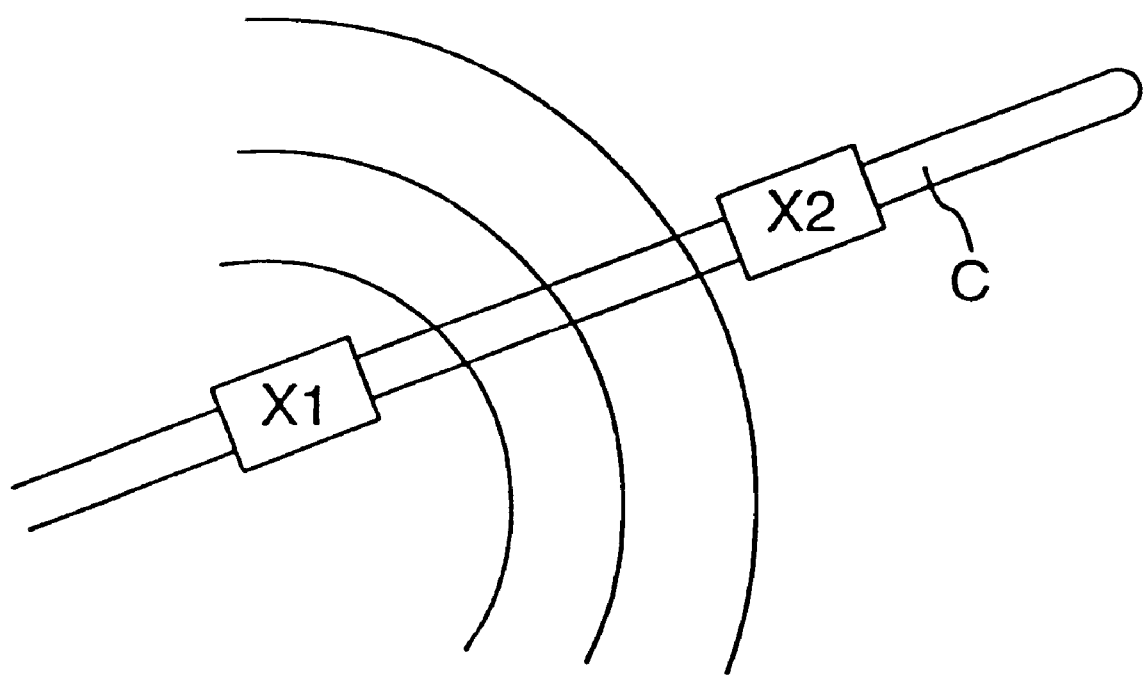
FIG. 9 is a schematic illustration of a catheter guidance system according to a specific implementation of the present invention.

For both reference frames, the method of transducer activation is identical. This process in discussed in detail above with reference to FIG. 6. An insulated conducting wire is used to carry the activation impulse from the control unit to the transducers. In the case of the transducers mounted to the catheter, the signal wires are internally routed through the same sheath as the steering guide wires. Finally, placement of the transducers is contingent upon which reference frame is employed. FIG. 9 illustrates the placement of the cylindrical transducers with respect to the catheter tip, according to the proposed catheter guidance application of the present invention. As can be seen, two ultrasonic crystals (X1, X2) are used on each catheter. This permits the transducers to communicate with each other, as well as to every other internally placed transducer in the region, and also the external reference transducers. By using the information from two colinear transducers mounted on a catheter, vector data can be acquired to illustrate not only the position of the tip, but also the direction. By using three or more transducers, the curvature and 3-D shape of the catheter can be reconstructed.

As can be seen, the two (or more) crystals (X1, X2) are permanently positioned along the axis of the catheter (C) at an appropriate separation distance for indicating catheter location, orientation and curvature. The piezoelectric material can bet affixed to the catheter with a variety of means, such as a pressfit, bonding, casting or vapor deposition.

Figure 10:
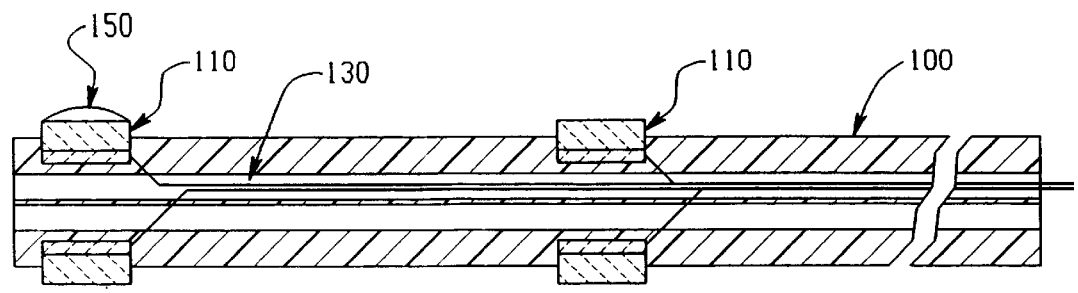
FIG. 10 is a schematic diagram of a multiple transducer catheter according to the preferred embodiment.

One embodiment of the transducer arrangement of FIG. 9, is illustrated in cross-section in FIG. 10. A multi-lumen catheter 100 (or any other suitable probe) is inserted into the body, such that the 3-D shape or extent of the device can be measured or represented, as discussed in greater detail below. As an alternative to using piezoelectric crystals 110, film patches may be used, such as PVDF (polyvinyldifluoride). PVDF is not a crystalline material, but a polymer. It is therefore made in sheets or strips and can be affixed to the catheter as a thin, rectangular patch of film. Its principle of operation is similar to that of PZT. PVDF is essentially a piezoelectric material that can be easily molded into different shapes and configurations.

The catheter 100 can be fabricated from any suitable polymer. A wire or wires (not shown) can pass through one of the lumens of catheter 100, or can be incorporated into the polymer during manufacture. The piezoelectric crystals 110 can be partially or completely embedded into the wall of the catheter 100 or can be affixed to the surface thereof. The crystals are preferably mounted on a suitable lossy backing 130 to which electrical conductors 140 are connected. The crystals 110 can also be provided with a dome-shaped polymer lens 150 affixed thereto.

ii) Tracking of Intravascular Ultrasound Imaging Catheters, Balloon Catheters, and Stent Deployment Catheters Through Coronary Arteries and Through Peripheral Vasculature The tracking of catheters can be extended into the field of intravascular ultrasound. Intravascular ultrasound imaging is gaining increased acceptance as a means of diagnosing the severity and spatial distribution of atherosclerotic plaque. Intravascular ultrasound imaging involves the placement of ultrasound imaging transducers (e.g. PZT or PVDF transducers) on the tip of a catheter. The ultrasound imaging transducers rotate to provide a 2-dimensional circular picture of a cross-section of a coronary artery and the local pathology at the level of the artery where the tip of the catheter is located. The ultrasound frequency of commercially available intravascular ultrasound imaging systems is typically 30 MHz. An intravascular ultrasound imaging system can detect whether the plaque is calcified or just fibrosed, as well as the overall shape of the blockage and the remaining lumen of the coronary artery. In this regard, calcified plaque procues a shadow behind it, and it can be identified by a trained physician, and sometimes through image processing. A fibrous plaque is often a bump in the wall of the vessels and both proximal and distal edges are visible on an ultrasound image, as the plaque is somewhat transparent to ultrasound, just like the vessel itself. This information is often used as a diagnostic technique to plan interventions such as angioplasty (a balloon dilation of the artery) or intravascular stenting a metallic tube that keeps the artery distended and patent.

It has recently become clear that simple 2-D imaging of the artery generated by the ultrasound imaging transducers is not sufficient. Very often, contrast angiography under continuous fluoroscopy is used to determine where the catheter is sitting relative to the branches of the coronary arteries. Often, it is important to determine if the blockage and lesion is near a bend or not, and also what is the 3-D topography of the lesion. Often, if the lesion is near a bend, a different therapeutic plan may be implemented. For example, if the lesion is at the bend, an intravascular stent may not be deployed in that region. It should be noted that a lesion is visible on across-section of the artery using intervascular ultrasound imaging, and during contrast angiography, is also visible a narrowing of the artery. It should be appreciated that the precise shape of a vent of an artery may determine the way stents are placed.

Three-dimensional reconstruction of the intravascular ultrasound images adds diagnostic value to the procedure. Typically, the intravascular ultrasound images generated by the ultrasound imaging transducers are saved continuously as the ultrasound imaging catheter is slowly pulled back along the coronary artery. These images are then stacked beside each other, and displayed as a 3-D reconstruction of the artery. The problem is that as the ultrasound imaging catheter is pulled back to acquire a series of slices, only the position along the length of the vessel can be measured. The result is that a vessel is always reconstructed as if it were a straight tube. Even a highly tortuous vessel will be reconstructed as a straight tube, since the pull-back distance is measured at the point of entry into the patient, not at the imaging site. Furthermore, the pull-back position is not very indicative of the true distance along the artery. Between the entry point and the imaging tip of the ultrasound imaging catheter, there are considerable bends. A small pull-back of the ultrasound imaging catheter at the entry point is seldom reflected by a similar motion at the imaging tip. Very often the imaging tip moves as a series of jumps, rather than a smooth continuous motion.

The position of the intravascular ultrasound imaging catheter can be easily tracked by mounting a low frequency transmitter near the imaging tip of the ultrasound imaging catheter. By having a dual display showing the view inside the vessel with the ultrasound, and the position of the imaging area relative to the gross morphology of the vessel on the angiogram, the angiologist can better treat the lesions and reduce the procedural risks to the patient.

The procedure for tracking the ultrasound imaging catheter will now be described in detail. By mounting PZT or PVDF transducers on the imaging tip of the ultrasound imaging catheter and mounting additional reference transducers internal or external to the patient to provide one or more reference frames, the catheter guidance system (CGS) can be used to track the 3-D position of the imaging tip, and the spatial location of the multiple slices can be recorded. The spacing of the slices can be adjusted to reflect non-uniform motion at the imaging tip, and the angulation of slices is also determined from the orientation of the imaging tip. It should be appreciated that the transducers should be placed close enough to the imaging tip of the ultrasound imaging catheter such that its motion can be referenced to the transducers. If the imaging tip is rigid, then two transducers can be placed along the rigid section to obtain a vector perpendicular to the imaging plane. Typically, the imaging transducers are not located at the imaging tip, but a little further down, since the imaging tip often has a little rubber flexible section to enable easier insertion into an artery. It will be appreciated that reference transducers may be advantageously positioned at the right ventricle, pulmonary artery or coronary sinus.

Tracking the imaging tip enables the reconstruction of the true 3-D shape of the artery with all its twists and bends. Such information is very valuable for the planning of dilation or coronary stenting procedures. During such a procedure, the computer system will typically record the 3-D position of the imaging tip, as well as its angular orientation, and save the data to a file as the same instant that the ultrasound image is saved. During image processing and 3-D reconstruction, this information will be used to reformat and spatially locate the sequential images, such that an accurate shape of the reconstructed artery can be obtained. It should be appreciated that the x,y,z, coordinates of the catheter imaging tip, referenced to time or image number, are saved to enable the reformatting and reconstruction of a 3-D image data set. The same 3-D data set can be used to advance the therapeutic catheters to the appropriate position, using the 3-D tracking procedures described above.

iii) Tracking of Biopsy Catheters or Biopsy Needles

Biopsies are typically performed to diagnose organ diseases, (e.g., cancer) or organ rejection. The tracking of biopsy catheters is of particular importance, because occasionally the biopsy "bites" are taken from the wrong part of the heart, liver, breast or other tissue or organ to be sampled. This is particularly significant in biopsies that are supposed to be diagnostic of cancer. In breast, liver and other internal organs, the tissues are highly deformable and catheter-based or stereotactic biopsies are typically not successful. In the case of the heart, sometimes a piece of the coronary artery is cut off, or the cardiac valve is damaged, with obvious complications to the patient. By following the path of the biopsy device, using single or multiple angiograms, x-ray images, or ultrasound image sets and real time overlay of the tracked biopsy catheter, the biopsy procedure itself can be made more precise and safe.

Biopsy needles can also be tracked with ultrasound, such as when cannulating the carotid artery or the femoral artery. Prior art systems rely on having the needle cast a faint shadow in the B-mode ultrasound image. This shadow is not readily visible to the untrained eye, and has obvious limitations in precision. A true 3-D tracking of the needle under real time ultrasound using the principles of the present invention greatly simplifies such procedures.

These procedures for tracking biopsy catheters and biopsy needles can be improved significantly by using an internal reference frame. In this regard, reference transducers are inserted into the surrounding area (internal reference frame) using large gauge needles, or affixed to the surface of the patient (external reference frame), such as in the case of the breast procedures. The transducers mounted to the needle are preferably thin PVDF film, or very small slivers of PVT, embedded in the metal shaft of the needle. Importantly, the transducers must be located such that they surround the area of interest. The bodily structure (e.g., organ or tissue) is imaged as usual, the 3-D image set is registered with the reference transducers, and the procedure performed as described above. The visualization system may provide 3-D images or a collection of 2-D images, in which the progression of the biopsy catheter or needle can be viewed in real time.

iv) Tracking of Amniocentesis Needles

Another application of the real time tracking system of the present invention in the tracking of needles for use in the procedure of amniocentesis. A 3-D or 2-D image set of the fetus with the motion of the needle displayed, can increase the precision and speed of the procedure and can prevent injury to the fetus. In the case of amniocentesis, the reference transducers are placed on the sides and top of the patient's belly.

v) Guiding of Probes During Stereotactic Surgery

During some delicate surgeries, particularly in the brain, it is important to know precisely the 3-D position of the probe inserted into the head. Typical brain conditions that require the guidance of a probe during stereotactic surgery are removal of brain tumors, the surgical correction of aneurysms, and electrical abnormalities like epilepsy (ablation, destruction of neural tissue).

The conventional method for guiding probes involves rigidly fastening the patient's head to a stereotactic frame by placing screws and pins into the patient's skull. The patient, with the frame attached, is then imaged using MRI or CAT, and a 3-D reconstruction of the patient's head is created. Pathologic tissue or lesions, such as tumors, are then precisely located relative to the frame. The patient is then taken to the operating room and the required instruments, such as electrodes or ablators, are affixed to guides that allow the instruments to be moved along the specific paths into the patient's head. Once the surgical instrument is in place, the lesion can be corrected, destroyed or treated in some way. The foregoing approach is tedious, costly and subject to measurement error in translating the 3-D coordinates from the images to the actual position of the probes within the stereotactic frame.

An alternative approach involves the use of a 3-D wand. This instrument consists of an articulating metallic arm that is rigidly affixed to a surgical table. Each of the joints in the arm has an angular position sensor so that the 3-D coordinates of the probe tip can be calculated from the joint sensors. By matching visual landmarks on the patient's head to the same landmarks on the 3-D image using the probe, the head and the 3-D image can be registered with each other. The probe is then used during surgery to hold instruments and guide them into the brain in a manner similar to the stereotactic frame. The advantage of the wand is that it has many more degrees of freedom, and can be held by the surgeon. The disadvantage is that it is very expensive, and very bulky. Also, the position of the probe tip is always only as precise as the original calibration against the patient's head. The patient's head must remain rigidly affixed to the table to which the articulating arm is fixed.

An existing alternative to the 3-D wand is an air-based 3-D locator system, which is the subject of U.S. Pat. No. 5,517,990. In this system, the position of a freely held wand is determined using triangulation of audible sound pulses in air. One major disadvantage to this approach is that the air-based 3-D locator system requires microphones to be placed at fixed sites in the operating scene. The patient's head must still be rigidly affixed to the table and the surgeons must take care not to get in the way of the sound path. This severely limits the freedom to perform the surgery.

A further application of the 3-D tracking and imaging system according to the present invention involves affixing reference transducers anywhere on the patient's head, and several transducers on the tip and shaft of the probe. The transducers can be conventional PZT material, or PVDF. Typically, a minimum of four reference transducers would be placed against the patient's skull, in order to generate an external reference frame. Other reference transducers would be inserted into the brain to provide an internal reference frame.

As the probe is inserted into the head, its movement relative to the reference transducers can be tracked in real time 3-D. The probe will be inserted into the brain, toward the lesion which is visible on a 3-D data set that was previously acquired through CT or MRI. Accordingly, the path of the probe is followed on a computer screen toward the lesion, rather than actually looking at the brain. The lesion itself is located by the position using MRI or CT imaging. The reference transducers affixed to the patient's head can be imaged along with the patient, simplifying the registration process, and since they are affixed to the head, movements of the head relative to the operating table do not pose a problem with respect to tracking. Since the sound path is inside the patient's head, surgeons have complete freedom to move about the patient. As in the catheter guidance system (CGS) described above, the location of the probes is tracked with respect to a reference system. For the head and brain, the most appropriate reference system are 3-D MRI images.

Patients with electrical disturbances of the brain, such as epilepsy, need to have the location of the epilepsy mapped properly prior to surgical intervention. This is done by placing surface electrodes subdurally over the brain. These electrodes are pushed along the brain through small access holes drilled into the skull. However, the location of the electrodes is often difficult to know precisely. Transmitter or receiver transducers are arranged on an electrode pad and on complementary electrode pad located on the outside of the skull. Accordingly, the motion of the electrodes can be tracked in real time, or can be verified with images of the brain taken previously. This greatly simplifies the mapping of brain wave activity anomalies.

The system for carrying out the foregoing procedure would preferably be comprised of the 3-D locating and imaging system described in detail above. Several transducers (PZT or PVDF) are mounted on the surgical probe to be inserted into the brain. Reference transducers are mounted either on the outside of the skull, or slid inside the head, between the brain and the skull. The reference transducers placed on the outside of the patient's head may be taped on or include adhesive backing tape. The reference transducers inserted into the brain will be anchored by sutures, hooks, or simply by friction alone. The patient may be imaged using MRI, CT, or any other multidimensional imaging modality, with the reference transducers in place. Accordingly, a volume reconstruction of the patient's head would be obtained. The reference transducer may be fitted with components that would enable them to be clearly seen on the 3-D image sets. A physician could then locate the lesion, or plan the surgical approach with respect to these referenced transducers. For example, the physician could draw a path in 3-D space that would be optimal to follow during the procedures. This path, as well as the intended location of the end point of the procedure, would be recorded by the computer system. The physician could also mark the location of the multiple transducers on the 3-D images, so that the computer system could register the physical location of the transducers to a location in the 3-D image space. It should be appreciated that depending on where the lesion is located in the brain, the surgical probe will be inserted from a different direction. Moreover, it is often necessary to go around critical areas so that minimal damage is done to the brain during insertion of the surgical probe.

The patient would be taken to the operating room with the reference transducers still affixed to the head, and connected to the 3-D locating and imaging system. The surgical probe would then be inserted into the brain, and its location in 3-D space would be instantly displayed within the 3-D volume of the brain, properly registered with the location of the reference transducers. By watching the progression of the surgical probe through the brain, the surgeon would be able to follow a predetermined path towards an intended target.

If the reference transducers are placed on the brain, or implanted within the brain, the path towards a lesion could be tracked even more precisely, since some deformation of the brain is expected upon manipulation of the patient and the insertion of the surgical probes into the brain. Therefore, if the reference transducers detect that their mutual spatial relationship has changed significantly, a coordinate transformation may be implemented, such that the 3-D image set of the brain is warped to the new geometry, as provided by the reference transducers. The required path towards the lesion can be altered according to this spatial transformation and the surgeon can be confident that the surgical probe is actually progressing towards its intended position. It is because of the expected motion or deformation of the reference transducers, that the internal reference frame is of significant benefit. If a rigid, external reference frame is used, deformation of the brain during surgery could not be detected and the stereotactic probe could very well miss its intended target.

It should be appreciated that the foregoing procedure can be easily integrated with robotic surgery. Therefore, rather than relying on a surgeon to slowly insert the probe, a much more precise robotic arm may be used. Again, the presence of the internal reference frame, and its ability to detect and correct for internal deformations can ensure that the probe is moving along its intended path through the brain, even though the brain tissue in its path may deform.

It should be appreciated that robotic surgery is particularly advantageous where a "steady hand" is required. In this regard, a robotic arm can precisely maneuver along a predetermined path determined by a physician in a 3-D image of the brain. In order to monitor the progress of the robotic arm, a feedback signal may be sent to a control system to make sure that the robotic arm is actually following the intended path.

vi) Embolization of Leaking Vessels

The 3-D tracking and imaging system described above is also useful during catheter based brain surgery to seal leaking cerebral arteries, or scirrhotic liver veins. Presently, when a patient has a burst cerebral artery, the vessel needs to be sealed up surgically through open brain surgery, or by plugging it up internally with microcatheters. Microcatheters are generally 0.3 mm I.D., 0.5 mm O.D., with a guide wire inside. Typically microcatheters take the form of very small plastic tubes that are flexible in bending, but rigid in torsion so that they can be twisted and manipulated. The microcatheters are threaded into the brain under fluoroscopy until they are near the site of the lesion. The catheter is then used to inject a sealant, such as glue (e.g., n-butylcyanoacrylate) mixed with a contrast agent, that hardens and embolizes, and then plugs up the micro artery down stream. Other sealants that may be deposited are PVAC sponge (100–300 mm dia.), and platinum micro coils (0.010" dia.). The problem with the foregoing procedure is that physicians do not know exactly where the released materials go, and can only track their path using multiple views on fluoroscopy. For heppatic veins, thrombin glue may be used.

The 3-D tracking and imaging system described above dramatically improves the precision for the foregoing procedures. As in the case of brain surgery, a 3-D image set of the cerebral vasculature is obtained and the progression through the vasculature may be monitored by projecting the position of the catheter within the 3-D scene of the vasculature. This may be done by mounting appropriate PZT or PVDF transducers on the catheters and tracking them as described above. The 3-D scene of the cerebral vasculature may be obtained through a CT scan with contrast agent injected into the patient, or with MRI tuned to show moving blood. Similar to the brain surgery procedure described above, transducers are arranged on the catheter and reference transducers are arranged on the patient's head. It should be noted that the placement of the external reference transducers is dictated by the location of "ultrasound" windows that enable signals to be sent into the skull. Accordingly, the preferred position for the reference transducers are the base of the head near the back, the eye sockets, or under the chin. For the liver and other internal organs, transducers can be placed on the skin or on catheters inserted inside the patient.

The catheters are inserted into the brain initially through an artery near the head, such as the carotid, and maneuvered into the brain. Leaking vessels are located in the brain using contrast and angiography. A contrast agent is injected into the blood stream, and the patient's head is imaged under x-ray fluoroscopy. The presence of the contrast agent makes the arteries into the head visible and the leaks in the brain appear as fuzzy areas of fluid leakage. The 3-D scene of the vasculature is registered with the position of the reference transducers attached to the patient's head. The location and shape of the microcatheter will then be displayed on a computer screen. Accordingly, the physician can interactively steer and advance the catheter through the many branches until it reaches the intended site. The specific sealant used in the procedure can then be released at just the right spot. The principal advantage of the foregoing approach is that the potentially harmful, long-term exposure to X-rays required when using fluoroscopy, can be eliminated. The tracking catheter can also be used to reconstruct the 3-D curvature of the vessels, augmenting conventional fluoroscopy.

vii) Measurement of Cervical Dilation

The onset of labor can be a well controlled process. During the first set of contractions, nurses periodically track the dilation of the cervix. At present this is done by checking the width of the cervix manually. More specifically, one or two fingers are inserted to feel for the head of the fetus, and estimate the degree of cervical dilation. These dilation measurements are done at regular intervals and a time/ dilation curve may be plotted. As a result, the obstetrician can plan the delivery, since the major contractions will come once the rate of cervical dilation increases.

The plotting of such dilation curves can be automated and managed for many mothers in the delivery room by measuring the dilation of the cervix with ultrasonic transducers according to the principles of the present invention. Therefore, a maternity ward can be networked so that progress of many mothers going through labor can be monitored remotely by a few nurses at a central station. The obstetrician is thus able to predict which patient is due to deliver at what time, and can plan his or her activities more precisely. A further advantage of this system is that the frequency of the digital exams is reduced and hence the rate of infection is reduced as well.

viii) Evaluation of Knee Stability

In some orthopaedic procedures, the stability of the knee needs to be evaluated quantitatively during walking. Knee stability can be assessed through manual manipulation; however, only by using a complex imaging technique can the motion of the knee during walking be mapped. By implanting the transducers of the present invention in the knee, the relative motion of the joints can be measured quantitatively during normal gait, and any surgery to augment ligaments can be better planned.

ix) Assessment of Myocardial Contractility Following Surgery

Following open heart surgery to repair the myocardium or the coronary arteries, the patient has to be monitored to adjust the levels of drugs that are administered. This is referred to as "titration" of drugs. The myocardial contractility is measured with a Swan-Ganz catheter and the drug level adjusted to obtain optimal cardiac function. Unfortunately, the Swan-Ganz catheter measures pressure, which is an indirect measure of contractility and can produce inadequate data.

However, a pair of transducer according to the present invention provide direct measure of myocardial contractility if attached to the beating ventricle. The transducers can be attached to the myocardium, attached to the myocardium directly, or to inserted pacemaker leads, during open chest surgery and can measure the contractility of the heart directly while the chest is open. The leads can then be strung out through the chest wall, and monitoring of myocardial contractility can continue for a few hours or days post operatively. This approach replaces the less precise Swan-Ganz catheter, and can be used to titrate the drugs given to the patient. If the transducers are properly positioned, they can be removed post operatively by pulling on them, in much the same way that pacing electrodes are removed.

x) Eye Surgery

Recently, ultrasonic microscopic imaging has made tremendous progress. Accordingly, it is now possible to obtain 3-D images of the eye using high resolution 3-D ultrasound. For highly precise eye surgery, stereotactic tracking of surgical probes can be done using the 3-D tracking and imaging system of the present invention. Like the brain surgery procedures described above, the movement of the probes can be tracked in real time, and their position displayed within a 3-D image of the organ. In the case of the eye, a high quality 3-D image of the eye may be used to provide the template through which the probes are to be moved. It should be appreciated that this application is highly suitable for robotic microsurgery.

xi) Prostate Surgery

Prostate surgery may be required when a prostate has become enlarged. This condition can cause such problems as incontinence and impotence. In many cases, the enlarged prostate is caused by a tumor. The tumor will need to be destroyed or removed, otherwise it may spread and kill the patient.

As in the case of eye surgery, 3-D ultrasound is useful in the diagnosis of prostate tumors. 3-D ultrasound may be used to visualize the size and shape of the prostate and may also be used to aid in stereotactic surgery of the prostate. However, it should be noted that 3-D ultrasound typically gives poor quality images and does not provide real time position feedback. Accordingly, there is a need to track the position of the surgical probes in real time using some other modality. The approach used in connection with the prostate and other internal organs would be essentially the same as the approach used in connection with the eye. In this respect, the organ of interest would be imaged using 3-D ultrasound, and the probes visualized with the 3-D tracking and imaging system of the present invention, as the probes are manipulated through the organ. The region to be treated is initially determined using an x-ray or ultrasound.

The probes are inserted through the urethra, or through skin between the penis and the rectum. Since it takes several minutes to obtain a new 3-D image, the 3-D scene can be periodically updated to show the progress of the surgery. Transducers are placed at several sections along the length of the probe, to provide accurate tracking of the probe location. Reference transducers are placed on the patient's body at locations that enable them to communicate with the transducers mounted to the probe. Therefore, the reference transducers need to be in locations that surround the area of interest, and also have appropriate ultrasound "windows" through which the sound can pass. Accordingly, bones and air pockets may not be in the way.

xii) Tracking of TMR Catheters

TMR is an acronym for Trans-Myocardial Revascularization. This procedure involves the "drilling" of holes through th e myocardium wall to improve circulation through the tissue. When coronary arteries become blocked with atherosclerotic plaque, the heart muscle downstream receive less blood than necessary and becomes ischemic. The traditional surgical approach to this problem is coronary artery bypass. A novel approach to revascularizing ischemic myocardium, without the lengthy and potentially complicated coronary bypass procedure, is to use TMR. The conventional approach to TMR is to expose the heart through a chest incision and drill holes through the muscle from the outside in, all the way into the ventricular chamber. This is done using a fiber optic light guide, (about 1 millimeters in diameter) that carries laser light energy. The fiber guide is placed against the heart, perpendicular to the surface and pushed into the heart as the laser is fired. The laser drills a channel ahead of it as the light guide is pushed through the muscle. Once the hole has been drilled, blood very briefly squirts out through the hole, but the outer portion of the hole quickly seals with clot and physically contracts as the heart muscle beats. During a typical procedure, the surgeon would drill a dozen or more holes through the myocardium in the ischemic area. The benefit to the patient is almost immediate, and continues for many months afterwards.

While it is not clear exactly how and why the procedure works, it is speculated that in the short term, the holes created allow blood to percolate through the muscle in some way, while in the long term, the injury created stimulates angiogenesis, or the growing of new collateral capillaries and arterioles.

The obvious disadvantage of the conventional approach to TMR is the need to expose the heart. A preferred method would be to use a catheter based approach that would drill the holes from the inside out. Such a procedure, however, requires proper guidance and visualization of the catheter within the heart. The 3-D tracking and imaging system of the present invention is well suited to this medical procedure. The TMR catheters may be fitted with ultrasonic transducers in much the same way as electrophysiology catheters.

Since the laser energy must be applied to the tissue directly, and cannot be passed through the blood, the light guide must be in contact with the tissue before the laser is fired. The required TMR catheter can therefore be fitted with a solid state (MEMS) force transducers that can measure the applied tip force against the catheter in 3 axes. The tip of the catheter may also be fitted with an ultrasonic transducer to look forward and determine to what depth the catheter has been passed through the muscle, and if it is about to come out the other side of the ventricle.

xiii) A 3-D Environment with 2-D Echo Planes Presented Within

A large number of diagnostic and surgical procedures are performed with the assistance of conventional 2-D echo imaging techniques. In this respect, the physician manipulates a surgical instrument (e.g., a probe or catheter) inside the patient's body, and at the same time tilts the imaging head of the echo machine until the ultrasound beam transects the instrument and the instrument becomes visible on a display monitor. Very often, the instruments are located after considerable "hunting", and the process itself is quite cumbersome. This procedure is often used in the case of amniocentesis and biopsies. In each case, needle or "biting" tools are inserted under ultrasound imaging guidance. In the case of amniocentesis, a physician inserts a needle through the abdomen into the uterus, while at the same time an assistant holds the ultrasound probe steady, making sure that it transects the amniocentesis needle, so that the needle can be visualized.

It would be advantageous to use a virtual 3-D environment that can be visualized on the display monitor of a suitable 3-D graphics computer, according to the present invention. In this regard, several reference transducers are placed on the back and abdomen of the patient, and a simple coordinate system is generated on the computer monitor, showing the direction towards the head and feet, the left and right sides of the patient, and the front and back. Initially, this would appear as an empty box with simple graphics or arrows, as well as the surface transducers shown graphically. When an amniocentesis needle is inserted into the abdomen, one or more ultrasonic transducers mounted along the needle shaft are tracked and displayed within the 3-D environment as simple graphical elements. This 3-D scene can be visualized from any viewpoint by simply moving the mouse and rotating the visual scene on the computer.

Figure 17A:
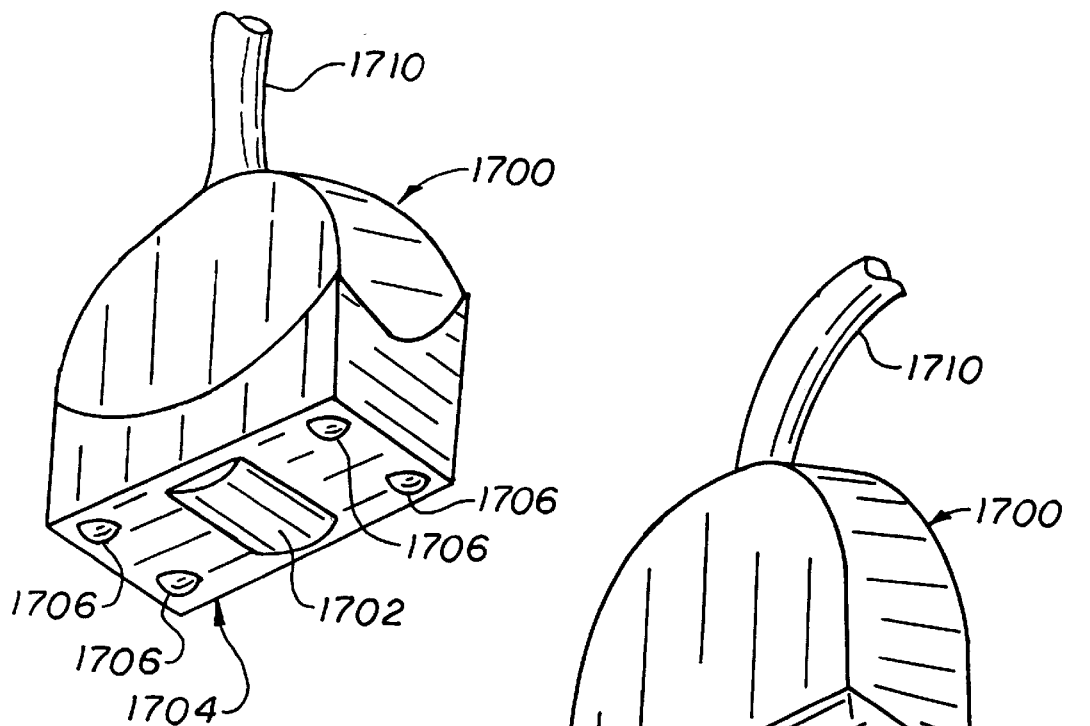
FIG. 17A is a perspective view of an ultrasound imaging head with a tracking clip attached thereto.
Figure 17B:
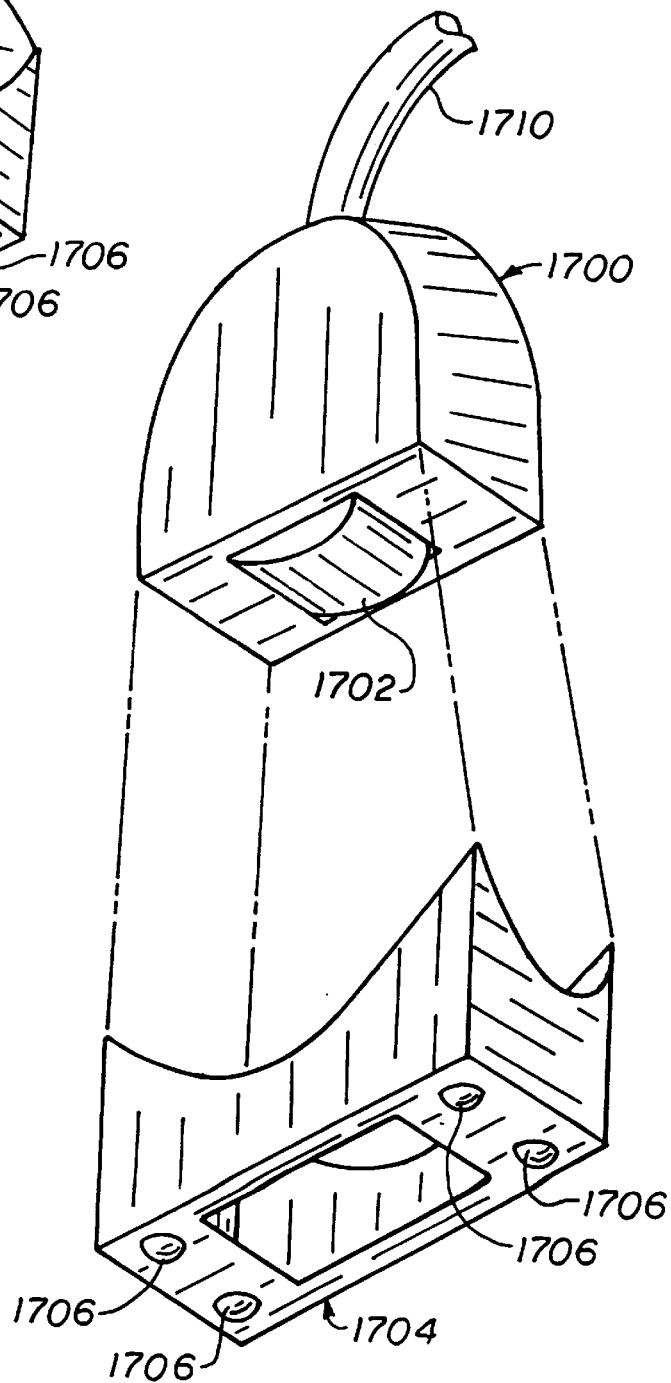
FIG. 17B is an exploded view of the ultrasound imaging head with tracking clip.

A preferred embodiment of an echo imaging system according to the present invention will now be described with reference to FIGS. 17A, 17B and 18. A typical echo machine ultrasound imaging head 1700 has a plastic hand held component with a cable 1710 that connects to a main unit (not shown). Imaging heading 1700 has a window through which ultrasound is transmitted and received by an image transducer 1702. The ultrasound imaging head 1700 is fitted with a transducer housing 1704 which clips to imaging head 1700. An exploded view is shown in FIG. 17B.

Transducer housing 1704 holds three or more position transducers 1706 that form a plane perpendicular to the imaging beam. Thus, position transducers 1706 reside between the imaging head 1700 and the skin that imaging head 1700 contacts. It should be appreciated that while four position transducers 1706 are shown in FIGS. 17A and 17B, only three position transducers 1706 are need to measure all angles. Reference transducers (not shown) are mounted to the patient's skin (e.g., back and abdomen). As the imaging head 1700 is tilted and angulated while pressed against the abdomen, the coordinates of position transducers 1706 define a plane that is perpendicular to the ultrasound imaging beam. It should be noted that transducer housing 1704 makes contact with the abdomen. Once the position and orientation of the imaging plane is known in 3-D space relative to the coordinate system of the patient, the typical pie-shaped sector scan produced by the ultrasound imaging head can be inserted into the 3-D scene of the patient. The 3-D scene will therefore contain a perspective rendering of the patient frame of reference, the location and direction of the surgical instrument (e.g., amniocentesis needle), and the pie-shaped, ultrasound sector image, properly oriented within this scene, as shown in FIG. 18.

The ultrasound image may be shown in real time in perspective by texture-mapping the video signal onto a pie-shaped polygon drawn in the 3-D scene. Current generation graphics computers enable this type of real-time image transformation. It should be noted that the location of all of the transducers with respect to each other can be determined, in the manner described above. Accordingly, one of the transducer locations is chosen as the origin, another as the x axis, and a third as the y axis, and a fourth as the z axis. The coordinates system may be defined by the user. The orientation of the imaging plane is calculated from the angle of the four imaging head transducers 1706, and the coordinate system defined by the reference transducers mounted to the patient's body.

By visualizing the location of the imaging plane relative to the inserted surgical instrument, the imaging head 1700 can be more quickly manipulated and angled until it transects the surgical instrument (e.g., amniocentesis needle). The shadow of the surgical instrument then becomes visible in the texture mapped, real time ultrasound image, and the surgical instrument graphic can be shown piercing the ultrasound image where its shadow is visible. Accordingly, a physician can immediately determine in which direction to angulate imaging head 1700 or move the surgical instrument to get proper orientation within the visual scene. Accordingly, the foregoing procedure is thus safer, faster and more precise than prior art procedures.

xiv) Tracking of Permanent and Temporary Pacemaker Leads and Catheters

The era of cardiac pacing began with direct epicardial implantation of electrodes. Epicardial placement of leads was subsequently replaced by endocardial introduction of leads through venous access. Fluoroscopic guidance has been used to provide accurate and reliable positioning of transvenous leads whether for a permanent pacemaker system or a temporary pacemaker system. Rapid deployment and positioning of the pacing lead to the pacing site within the heart is critical during emergency situations, while selecting the best anatomic site in a permanent system is critical for long-term stability and effectiveness. These objectives are best met with a direct visual guidance system. X-ray fluoroscopy is currently the only clinically available visual guidance system. This approach must therefore be done in an angiography suite, or some other facility equipped with a fluoroscopy system.

However, intracardiac pacemaker leads can also be positioned in a blinded way or facilitated by a flow directed, balloon tipped catheter. The ultimate position of these leads must be assessed by recording the electrogram and examining the morphology of the traces, and by determining the pacing threshold. Neither of these techniques, however, is considered to be as efficient as direct visual guidance of the catheter. Cardiac pacing can also be achieved by high output, direct stimulation of the chest wall or by cardiac pacing through the esophagus. These techniques are limited by patient discomfort and are intended only for relatively short term usage. The procedure of choice, therefore, is direct visualization of the pacing catheter.

Fluoroscopic guidance provides accurate and direct means of guiding a temporary or permanent pacing lead to its intended active pacing site. Fluoroscopy, however, has many disadvantages. These disadvantages include: (i) requirement of a specialized lead shielded facility to provide protection for passers by; (ii) accumulative radiation hazard to the operator and ancillary staff; (iii) radiation hazard to the patient; and (iv) the need for expensive and relatively bulky equipment which limits its ready availability in all areas of the hospital where it may be needed.

The 3-D tracking and imaging system of the present invention may be utilized to position pacemaker leads. As discussed in detail above, the 3-D tracking and imaging system makes use of numerous piezoelectric (PZT or PVDF) ultrasonic transducers affixed to stable or moving locations on the patient or on devices inserted into the patient, and tracks their position hundreds of times per second relative to a reference frame. The tracking of these ultrasonic transducers is accomplished by sequentially firing these transducers so that they produce waves of ultrasound that propagate through the tissue until they are detected by the other transducers. A matrix of distances between all combinations of transducers implanted in the body is thus acquired, and converted into x-y-z coordinates using suitable software and algorithms (triangulation), as discussed above. It will be appreciated that temporary or permanent leads may be placed in the heart for cardiac monitoring, pacing cardioverting (pacing catheter) or defibrillating (defibrillating catheter).

Figure 19A:
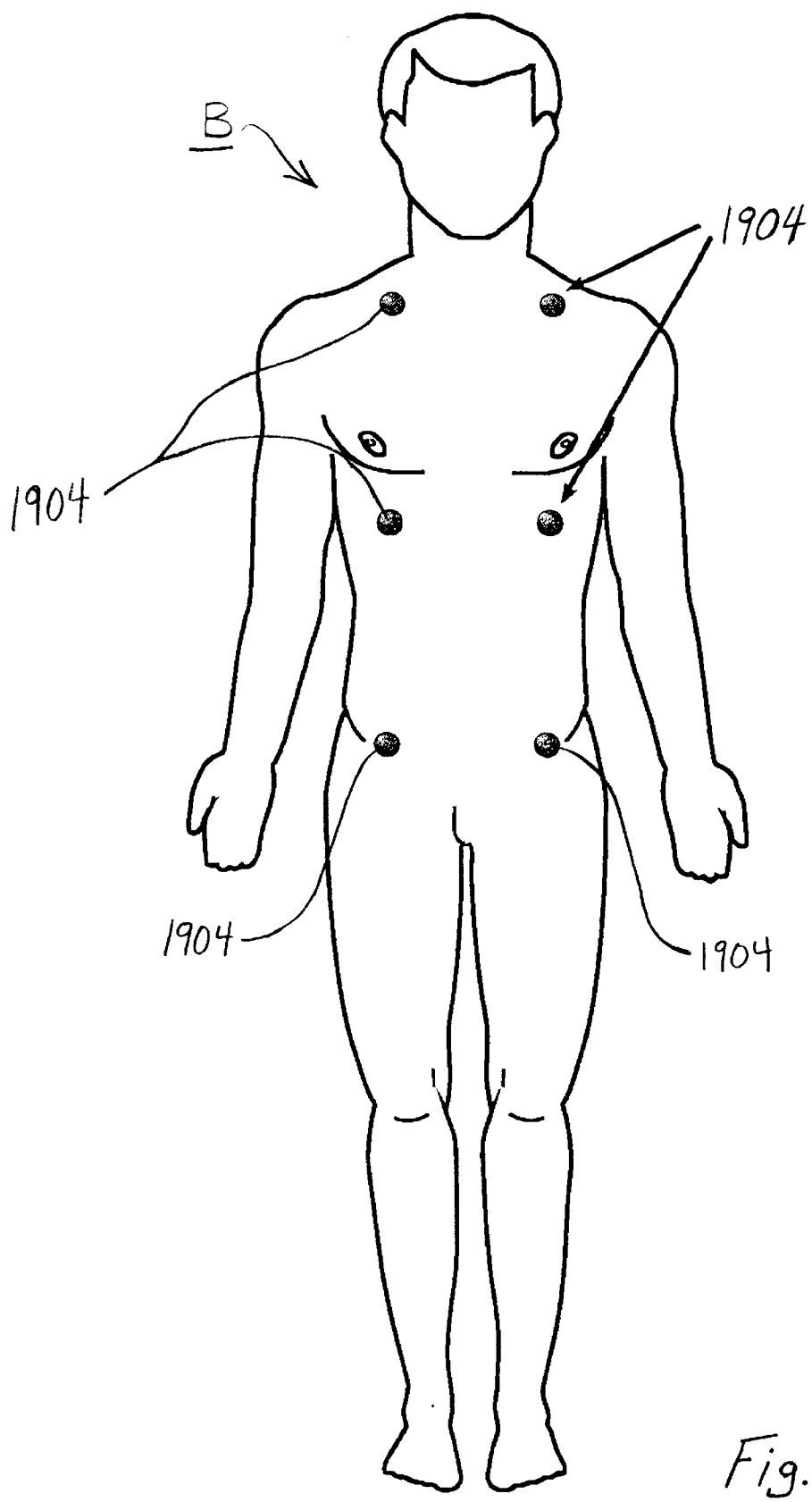
FIGS. 19A–19D illustrate the use of the 3-D tracking and imaging system to track pacemaker leads and catheters.
Figure 19B:
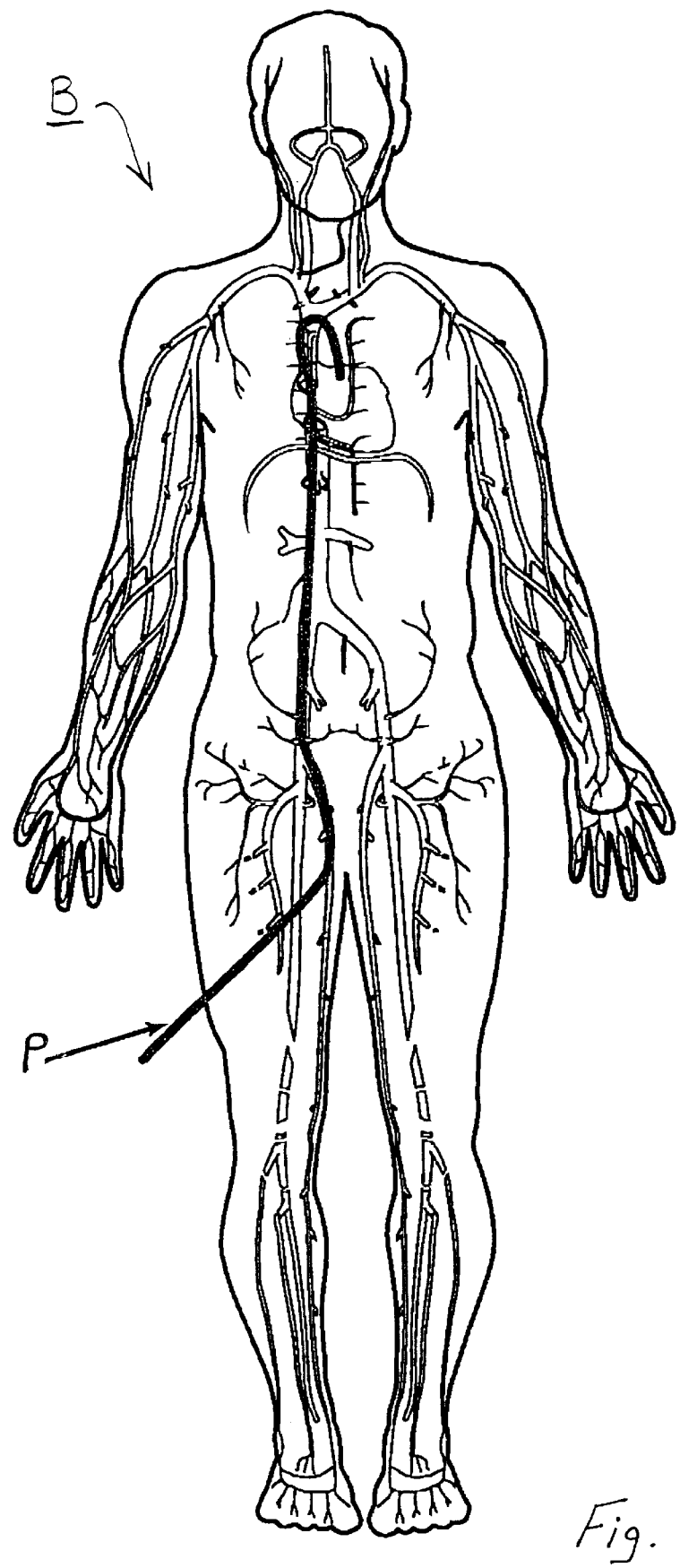

FIG. 19A shows a plurality of reference transducers 1904 placed at various positions on the external surface of a body B, while FIG. 19B shows a path P for a catheter which is to be inserted through the venous system. The catheter guides pacemaker leads which have mobile transducers incorporated within. By incorporating the mobile transducers on the pacemaker leads, and placing reference transducers on the chest or back of the patient, the progression of the pacemaker lead can be tracked in real time, with respect to the markers placed on the patient.

Since reference transducers 1904 communicate with all the others transducers connected to the 3-D tracking system, a mobile transducer can be moved relative to reference transducers 1904 to "draw" features in 3-D space as the mobile transducer is moved. As a result, portions of the anatomy of the patient can be generated and used as templates against which to track the position and motion of the inserted pacemaker leads or other catheters. The features can thus be placed within a 3-D or 2-D viewing environment.

Figure 19C:
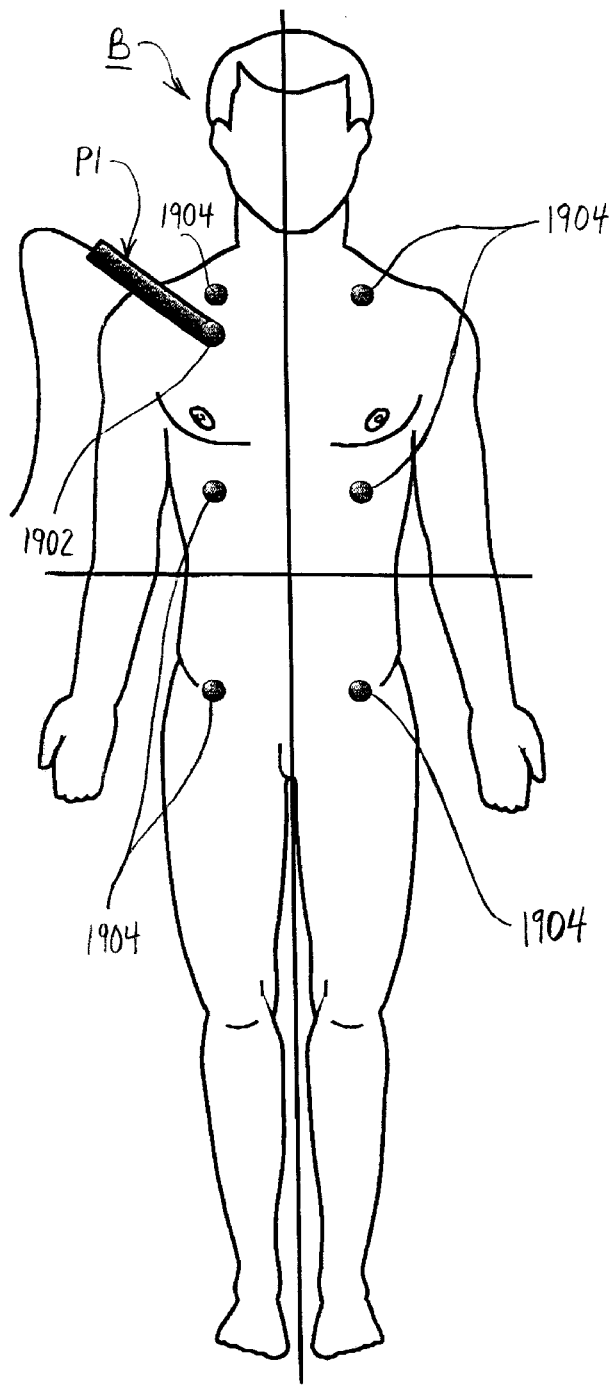
Figure 19D:
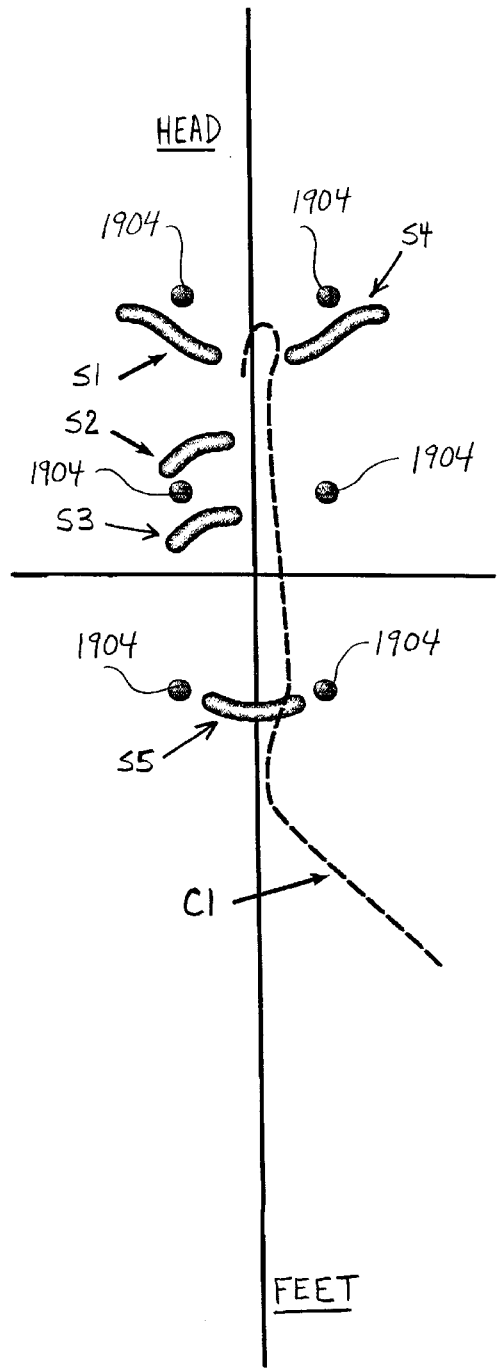

As shown in FIG. 19C, a hand-held probe P1 is configured to incorporate a mobile transducer 1902 at its tip. As probe P1 is placed against the skin of the patient, the tip of the probe can be tracked (e.g., as it is dragged along the surface of the patient's skin) with respect to other ultrasonic transducers that are part of an array of transducers (e.g., reference transducers 1904). As a result, lines may be drawn in 3-D space, following the paths that are traced by the probe. In this regard, FIG. 19D shows anatomical structures S1–S5, which are drawn using probe P1. Anatomical structures S1–S5 act as "helper marks" within the viewing environment to help in visualizing the position of a catheter C1 and any pacemaker leads associated therewith. This procedure, along with the plotting of the path of the catheter, will produce a sophisticated and accurate template, or pseudo-fluorogram against which catheters can be tracked. The principal advantage of this pseud-fluoroscopy is that it eliminates the reliance on an angiography suite for routine catheterizations.

xv) Virtual Stillness for Robotic Surgery on Beating Hearts

Coronary bypass surgery involves the insertion of a new vessel into an existing coronary artery, such that the length of the new vessel bypasses a blockage in the existing coronary artery. Traditionally, this type of procedure has been done during open heart surgery with the heart arrested and the patient on "cardiac bypass". Having the patient on bypass is a procedure that involves significant complications, particularly for the very sick individuals with sever coronary disease. There is always the risk that the patient cannot be weaned off bypass and will die on the operating table.

There has been a trend towards performing coronary bypass procedures with the heart beating. Delicate suturing of coronary arteries, however, cannot be done readily on the beating heart. A number of technologies exist for holding a portion of the heart stable so that the delicate suturing can take place. One such device employs multiple suction cups to hold onto the heart near the coronary vessels and reduce the degree of motion of the area being worked on.

In recent years, there has also been a trend towards robotic surgery. Robots, directed by human operators, are used to sew sutures. This approach has several advantages over surgeons directly sewing sutures, namely, (i) the surgeon can sit comfortably at a table, rather than bent over a patient for hours during difficult procedures, and (ii) for very fine suturing, the motion of the robotic actuators can be scaled down. The surgeon operates a robotic subsystem 1690 by using conventional hand movements, while a robotic control system 1694 (e.g., robotic actuators) scale the movements by a factor of 10 or more, to enable micro-surgery to take place using a robotic manipulator system 1694. A further advantage of this approach is the tremor inherent in all fine hand work, can be essentially filtered away by the robotic subsystem. Several such robotic subsystems exist, such as that being sold by Computer Motion, Inc., and disclosed in U.S. Pat. No. 5,515,478.

A further benefit of using a robot is its implementation in the beating heart approach to coronary artery bypass. Rather than holding down the heart with suction cups, the heart can be left to beat freely, while robotic manipulators follow the hearts repetitive motion. This can be accomplished by the using the 3-D tracking and imaging system of the present invention. By locating a mobile transducer on the vessel of interest, and tracking its motion with respect to several stationary reference transducers located elsewhere in the chest of the patient, the motion of the heart can be followed by the robotic subsystem. The motion of the sewing actuators can be modulated by the 3-D motion of the tracked vessel on the heart, so that the robot manipulator system can sew on the beating heart while the operator maneuvers robotic subsystem controls as if he is sewing on a stationary object.

To give the impression that the field of view is stationary or "virtually still," (1) the video camera viewing the scene can move along the same trajectory as the tracking transducer, or (2) the image obtained by a still video camera can be processed in real time and a central portion of it can be moved around the display screen such that the target of interest appears to be still. With regard to the latter, the position of a sub-image within the image plane (provided by the video camera) is translated in accordance with the three-dimensional coordinates generated by the 3-D tracking and imaging system. As a result, the motion of the sub-image is altered, which can make the sub-image appear to be still.

To the operator, the images provided by the video camera appear still, and the robotic actuators are manipulated as if the target was still. The robotics subsystem, however, moves in a cyclical manner, following the moving heart as it beats. This complex movement of robotic actuators, as well as the video processing, is enabled by the use of the 3-D tracking and imaging system of the present invention.

xvi) Tracking of Telephone Antennae

The radiation dosage that is being delivered to the head and body of the user of a cellular telephone is beginning to be of concern to the general public. For the purpose of studying the amount and distribution of radiation dose, it would be beneficial to have a device that can measure the location and orientation of a cellular telephone antenna with respect to the head of the user. The data that can be collected with this device can be used in estimating the radio frequency (RF) dosage to the head, based on established models of RF propagation. The ideal system could be used by test subjects in an ideally unrestricted manner for extended periods of time, during normal telephone usage.

Figure 20:
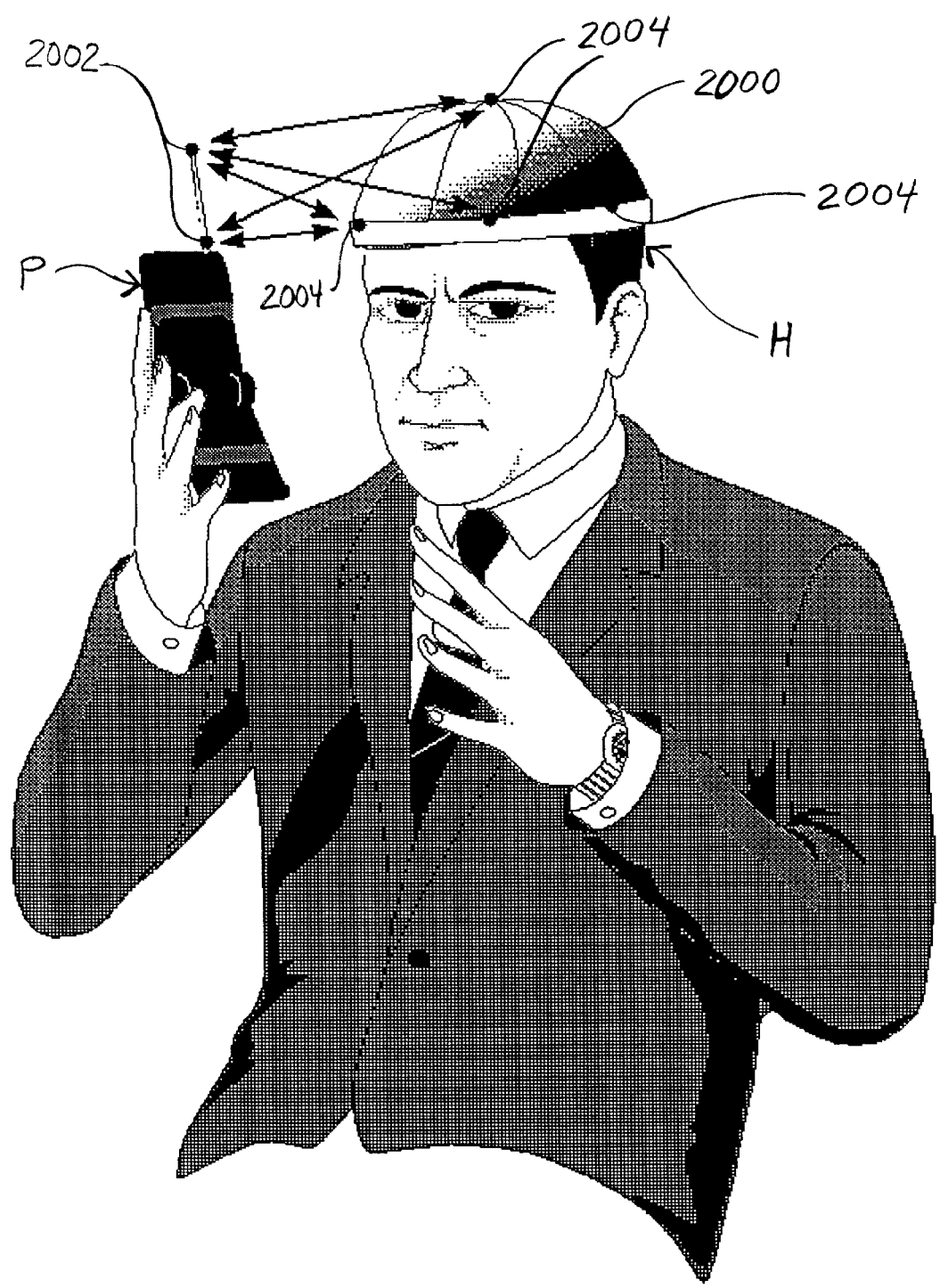
FIG. 20 illustrates the use of the 3-D tracking and imaging system to track the position of a cellular telephone antennae relative to a user's head.

FIG. 20 illustrates a cap 2000 mounted to the head H of an individual. A plurality of acoustic reference transducers 2004 are mounted at various positions on cap 2000. A plurality of acoustic mobile transducers 2002 are mounted to the antennae of a cellular phone P. A cellular phone antenna can be modeled as a linear element defined by its base and end point. The spatial relationship between these antenna end-points and N locations on the surface of the user's head can be measured by sonic ranging. The acoustic transducers 2002 and 2004, located at relevant points on the antenna and the user, emit short pulses of acoustic energy of approximately 40 kHz. The distance between transducers is calculated by first measuring the transit-time of these pulses and then applying the known speed-of-sound (i.e., using the equation Distance=Velocity×Time).

It is anticipated that the acoustic reference transducers 2004 mounted to the head of the user, could be worn as a hat or cap (as shown in FIG. 20), or be placed on glasses. The points on the head of the user need to be at relatively fixed locations so that the true 3-D relationship between the antenna and the head of the patient is determined.

Multiple distances between reference transducers 2004, arranged on the user's head, and mobile transducers 2002, mounted on the antenna, is measured using the technology embodied in 3-D tracking and imaging system of the present invention. The 3-D relationship between the antenna and the head mounted transducers is computed using established triangulation algorithms. Rather than use the ultrasonic transducers suitable for use in an aqueous environment, this embodiment of the present invention uses the more appropriate air-based ultrasonic transceivers that emit acoustic energy at about 40 kHz. These transducers are approximately 10 mm in diameter or smaller. The transducers are connected to an instrumentation module that performs all functions necessary to measure all relevant distances between transducers. This module therefore contains control, signal transmission, signal reception and measurement circuits. The size of the module would range from a belt-mounted housing several inches in size to as small as being totally incorporated into the cellular telephone itself.

xvii) Targeted Drug Delivery, Thrombolytic Factors, Angiogenic Factors

It is becoming increasingly effective to treat circulatory dysfunction by targeted therapy. For example, in coronary artery disease, restenosis after balloon dilatation or arthrectomy is being reduced by locally affecting the vascular smooth muscle cells in the lesion itself. "Gene therapy", using genetically engineered viruses, is being used to suppress the proliferative nature of smooth muscle cells in diseased artery segments. These biologic agents, as well as chemical agents, such as radioactive isotopes, and toxic drugs, are being delivered by means of conventional contrast fluoroscopy.

As mentioned above, fluoroscopy has some serious disadvantages: (i) it subjects the patient, the doctor and the catheterization lab assistants to high significant dosages of harmful X-rays, (ii) it requires the injection of contrast agent to identify the location of catheters inside ventricular and vascular structures, and (iii) it provides a 2-D projection of 3-D geometry, and hence does not offer a complete visual representation of the location and trajectory of the therapeutic catheters.

The 3-D tracking and imaging system of the present invention may be used in such applications to more fully localize the delivery tip of the catheter within the coronary artery tree and deliver the appropriate drugs or biologic agents to locally reduce the proliferative nature of injured or diseased vascular smooth muscle cells. Moreover, the present invention can be used to deliver potent thrombolytic agents to a site of coronary artery blockage. This would be done when there is a suspicion plaque rupture that causes blood to locally clot and occlude the coronary artery. A further use of this technique would be in the delivery of angiogenic factors to the heart or other organs to stimulate the growth of new capillaries in previously infarcted heart muscle. Local deliver of angiogenic factors would be an alternative to invasive revascularization as is done currently using lasers, in a technique known as percutaneous TMR (Trans-Myocardial Revascularization, or PMR).

The 3-D tracking and imaging system can be use for a whole range of procedures where local delivery of drugs and other bioactive substances is desired. Local delivery is always preferred over systemic administration of these substances, because it minimizes side effects, and enables the use of much more potent substances that otherwise could not be used.

Intramyocardial delivery of growth factors, be they for the purpose of inducing vascular growth or for treating intrinsic myocyte disease (such as cardiomyopathy) are presently under study by a number of investigators. The delivery of such factors via a percutaneous catheter system may be accomplished most effectively if the catheter tip position can be tracked in real time, if contact of the catheter tip can be confirmed, if the depth of injection can be controlled, if the sites of injection can be tracked so that desired inter-injection site distances can be ensured, if the viability of the myocardium at a potential injection site can be ascertained, and (potentially) if a small Intramyocardial void can be created into which the substance (especially a viscous substance) can be delivered and sealed.

The catheter system to achieve the foregoing includes the following components: (1) a steerable catheter with lumen which can be modified to include a catheter tip position system; (2) a catheter tip position system (i.e., the 3-D tracking and imaging system described above); (3) a needle which can be passed down the lumen of the catheter (the needle should be constructed of a flexible material which is electrically conductive, such as Nitinol); (4) a device which interfaces with the catheter hub and controls and indicates the distance of excursion of the needle past the catheter tip and also controls the amount and timing of drug injection; (5) electronic hardware and software to record and analyze the electrocardiogram recorded from the tip of the catheter and from the needle; and (6) a radio frequency (RF) energy source for creating an intramyocardial void by ablating muscle in which injections can be made.

Figure 21:
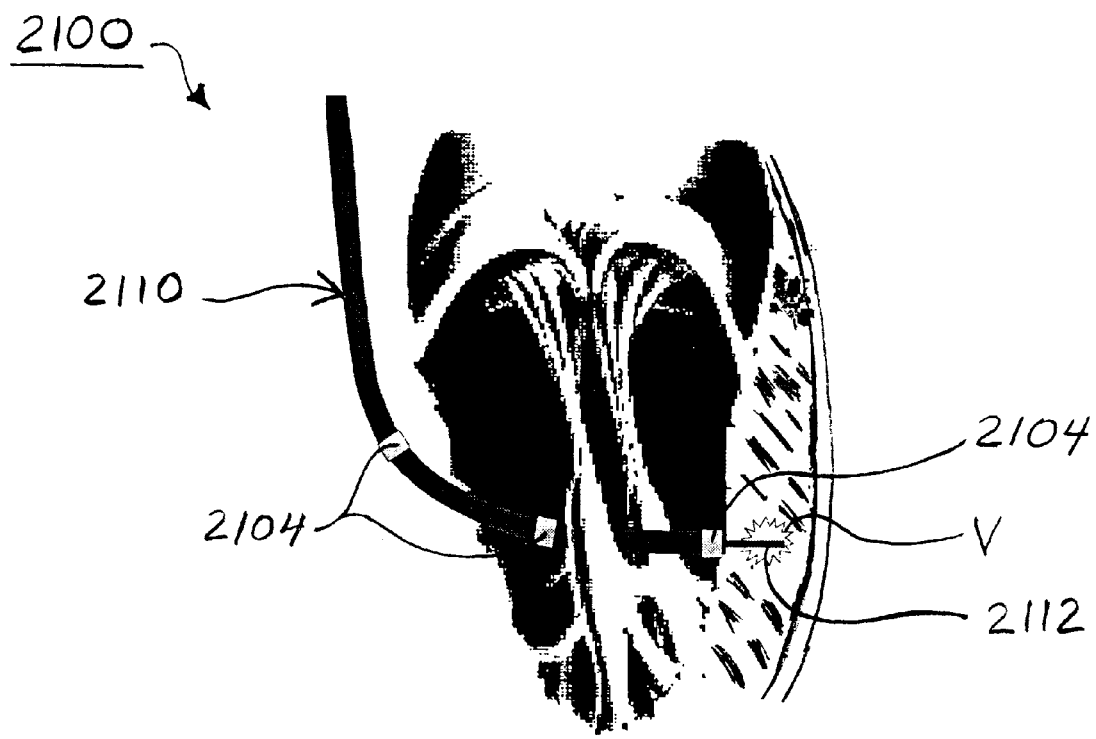
FIG. 21 illustrates a catheter tip position system, according to a preferred embodiment of the present invention.

FIG. 21 illustrates an exemplary catheter tip position system 2100 including a minimum of three piezoelectric transducers 2104 fixed at the distal end of a catheter 2110. Transducers 2104 allow accurate tracking of tip shape and position in real time. The most distal transducer is positioned at the very end of catheter 2104 so that when the catheter tip makes contact with the myocardial wall, the transducer itself will be in contact with the wall. This is important for several reasons. First, this allows a electrogram to be recorded from this electrode. By analyzing the amplitude of this signal, information pertaining to the viability of the myocardium can be inferred. An infarcted region provides a very low amplitude signal, whereas a viable region provides a relatively high amplitude signal. Second, if the electrode is in contact with the myocardial wall, it can serve as the reference point for a needle advanced into the myocardium. The 3-D tracking and imaging system also provides means for displaying the catheter tip, displaying wall motion at sites of injection and for keeping track of previous injection sites by graphically tagging points in 3-D space. In addition, a readout of the distance of the catheter tip from all previous injection sites may be provided. Moreover, the 3-D tracking and imaging system may be programmed to allow axis rotation so that a user can change the perspective from which the treatment target field is viewed.

It should be understood that a needle 2112 needs to pass down the lumen of catheter 2110 but not interfere with its flexibility. If the needle is electrically conductive then two features can be incorporated: 1) As with the catheter tip electrode, electrocardiogram can be recorded from the needle. This will provide confirmation that the needle is embedded in the myocardium. This is very important for ensuring that injections are not being made in the blood of the ventricular chamber. 2) A conducting needle will allow administration of radio frequency (RF) energy (if desired) for ablating a small amount of myocardium to create a void V (see FIG. 21) in which substances (particularly viscous substances) can be injected and sealed, as will be discussed in further detail below. While Nitinol is one appropriate material for this purpose, other conductive alloys are also suitable.

With further regard to the needle design, the needle itself should be blind, and numerous exit holes should be placed along its shaft for the length of its penetration into the myocardium. By allowing the fluid to escape from the needle laterally, instead of from the end, axial reaction forces that could otherwise dislodge the catheter tip during the injection are reduced or eliminated.

A device is provided to hold the needle and provide the user with a simple, rapid and accurate way of extending the needle from the catheter tip by the desired amount and allow the user to administer the desired amount of material. A pistol type hand controller which independently holds the catheter hub and the needle with two stops for the trigger is one suitable approach. When the user trips the trigger to the first position, the needle is advanced; the depth of penetration is adjustable by a calibrated micrometer screw. When the user applies further pressure to trip the tripper to the second position, the drug is delivered; the injection volume may also be controlled by a calibrated micrometer screw.

As discussed above, the electrocardiograms recorded from the tip of the catheter and from the needle can be used to ensure contact of the catheter tip with the myocardial wall and to provide an indication of whether the region of contact is infarcted or viable (i.e., not infarcted). The electrocardiogram recorded from the needle will provide critical information which confirms that the injection is being made into myocardium, and not into blood within the ventricular chamber.

Many growth factors are dissolved in viscous carriers. In this case, direct intramyocardial injections require substantial force in order to inject the desired volume. This force is mainly due to the resistance provided by the myocardium which is a densely packed material of tightly coupled muscle cells which do not easily separate. In order to create a small void in which to inject the volume, radio frequency energy can be used to ablate a small hole in the center of the myocardium. The needle is preferably electrically insulated in all but the final 1–2 mm. If this is the case, the ablation region will be limited to the mid-myocardial region. As the needle is withdrawn, the myocardium will seal on itself, thus containing the injected volume. If this is insufficient, it may also be possible to use radio frequency (RF) energy (likely of a different frequency) to seal the myocardium as the catheter is withdrawn.

The foregoing description provides specific embodiments of the present invention. It should be appreciated that these embodiments are described for purposes of illustration only, and that numerous alterations and modifications may be practiced by those skilled in the art without departing from the spirit and scope of the invention. For instance, it should be appreciated that the transducers may use the time of flight, or phase differences as a means of determining position. Moreover, the transducers may take the form of ultrasonic transducers or electromagnetic transducers. It is intended that all such modifications and alterations be included insofar as they come within the scope of the invention as claimed or the equivalents thereof.

Having thus described the invention, it is now claimed:

1. A method of performing an in vivo medical procedure on an associated body using a 3-D tracking and imaging system, said method comprising:

mounting at least one mobile transducer to a medical instrument;

mounting a plurality of reference transducers to locations on the body, the plurality of reference transducers being distributed at positions substantially surrounding the body;

energizing the at least one mobile transducer and the plurality of reference transducers such that at least one respective transducer generates a positional signal and at least another respective transducer detects the positional signal, to measure time-of-flight of the positional signal;

sequentially varying the energizing of each of the at least one mobile transducer and the plurality of reference transducers according to a duty cycle such that each transducer alternates between transmit and receive modes over the course of the duty cycle;

generating three-dimensional coordinates of the mobile transducer relative to a reference frame established by the reference transducers; and generating a display indicative of a positional path followed by said medical instrument.

2. A method according to claim 1, wherein said path is along the surface of the associated body.

3. A method according to claim 1, wherein said medical instrument is a probe.

4. An apparatus for performing an in vivo medical procedure on an associated body, said apparatus comprising:

at least one mobile transducer mounted to a catheter including a lumen;

a plurality of reference transducers mounted to locations on the body, the plurality of reference transducers being distributed at positions substantially surrounding the body;

means for energizing the at least one mobile transducer and the plurality of reference transducers such that at least one respective transducer generates a positional signal and at least another respective transducer detects the positional signal, to measure time-of-flight of the positional signal;

means for sequentially varying the energizing of each of the at least one mobile transducer and the plurality of reference transducers according to a duty cycle such that each transducer alternates between transmit and receive modes over the course of the duty cycle;

3-D generating means for generating three-dimensional coordinates of the at least one mobile transducer relating to a reference frame established by the plurality of reference transducers;

display means for generating a display indicative of a positional path followed by said catheter;

a needle extendible from a tip of the catheter; and control means for extending the needle from the tip of the catheter and initiating a flow of fluid from the needle.

5. An apparatus according to claim 4, the apparatus further comprising radio frequency (RF) generation means for generating RF energy to ablate at least a portion of a bodily structure.

6. An apparatus according to claim 4, wherein said needle includes exit holes along its length to dispense fluid.

* * * * *